(12) United States Patent
Bender

(10) Patent No.: US 10,888,618 B2
(45) Date of Patent: *Jan. 12, 2021

(54) METHOD OF TREATING CANCER

(71) Applicant: Intensity Therapeutics, Inc., Westport, CT (US)

(72) Inventor: Lewis H. Bender, Redding, CT (US)

(73) Assignee: Intensity Therapeutics, Inc., Westport, CT (US)

( * ) Notice: Subject to any disclaimer, the term of this patent is extended or adjusted under 35 U.S.C. 154(b) by 98 days.

This patent is subject to a terminal disclaimer.

(21) Appl. No.: 15/441,907

(22) Filed: Feb. 24, 2017

(65) Prior Publication Data

US 2017/0165369 A1 Jun. 15, 2017

Related U.S. Application Data

(63) Continuation of application No. 15/052,326, filed on Feb. 24, 2016, now Pat. No. 9,636,406, which is a continuation of application No. 14/280,036, filed on May 16, 2014, now Pat. No. 9,351,997, which is a continuation of application No. PCT/US2013/059841, filed on Sep. 15, 2013.

(60) Provisional application No. 61/779,509, filed on Mar. 13, 2013, provisional application No. 61/707,733, filed on Sep. 28, 2012, provisional application No. 61/703,890, filed on Sep. 21, 2012.

(51) Int. Cl.

| | | |
|---|---|---|
| *A61K 31/192* | (2006.01) | |
| *A61K 31/20* | (2006.01) | |
| *A61K 31/216* | (2006.01) | |
| *A61K 31/282* | (2006.01) | |
| *A61K 31/555* | (2006.01) | |
| *A61K 31/7032* | (2006.01) | |
| *A61K 31/7105* | (2006.01) | |
| *A61K 31/475* | (2006.01) | |
| *A61K 33/243* | (2019.01) | |
| *A61K 33/24* | (2019.01) | |
| *A61K 47/12* | (2006.01) | |
| *A61K 9/00* | (2006.01) | |
| *A61K 9/08* | (2006.01) | |
| *A61K 47/18* | (2017.01) | |
| *A61K 47/14* | (2017.01) | |
| *A61K 45/06* | (2006.01) | |

(52) U.S. Cl.
CPC ............ *A61K 47/14* (2013.01); *A61K 9/006* (2013.01); *A61K 9/08* (2013.01); *A61K 31/192* (2013.01); *A61K 31/20* (2013.01); *A61K 31/216* (2013.01); *A61K 31/282* (2013.01); *A61K 31/475* (2013.01); *A61K 31/555* (2013.01); *A61K 31/7032* (2013.01); *A61K 31/7105* (2013.01); *A61K 33/24* (2013.01); *A61K 33/243* (2019.01); *A61K 45/06* (2013.01); *A61K 47/12* (2013.01); *A61K 47/18* (2013.01); *A61K 9/0019* (2013.01)

(58) Field of Classification Search
CPC ........ A61K 47/14; A61K 33/243; A61K 9/08; A61K 47/18; A61K 31/475; A61K 47/12; A61K 31/192; A61K 31/20; A61K 31/216; A61K 31/282; A61K 31/555; A61K 31/7032; A61K 31/7105; A61K 33/02; A61K 9/0019; A61K 31/517; A61K 31/58; A61P 35/04; A61P 35/02; A61P 35/00; A61P 1/18
See application file for complete search history.

(56) References Cited

U.S. PATENT DOCUMENTS

| 4,978,332 | A | * | 12/1990 | Luck | ............. | A61K 33/24 |
| | | | | | | 514/930 |
| 5,162,115 | A | * | 11/1992 | Pietronigro | .......... | A61K 9/0019 |
| | | | | | | 424/1.49 |
| 5,679,638 | A | | 10/1997 | Teicher et al. | | |
| RE35,748 | E | * | 3/1998 | Luck | ............. | A61K 47/42 |
| | | | | | | 424/425 |
| 5,866,536 | A | | 2/1999 | Leone-Bay et al. | | |
| 5,874,402 | A | | 2/1999 | Singh et al. | | |
| 6,110,492 | A | | 8/2000 | Alving et al. | | |
| 7,648,695 | B2 | | 1/2010 | Dees et al. | | |

(Continued)

FOREIGN PATENT DOCUMENTS

| CN | 101928234 A | 12/2010 |
| WO | WO 97/30705 | 8/1997 |

(Continued)

OTHER PUBLICATIONS

L. Hsu et al., "Determination of 5-fluorouracil in human plasma by high-pressure ion-exchange chromatography," Ann. Clin. Biochem. 1980; 11: 272-276.*

(Continued)

*Primary Examiner* — Monica A Shin
(74) *Attorney, Agent, or Firm* — Cooley LLP; Ivor R. Elrifi; Matthew Pavao

(57) ABSTRACT

The invention provides a method for treating cancer using a coadministration strategy that combines local codelivery of a therapeutic agent and an intracellular penetration enhancing agent, and optionally in further combination with local administration of an immunotherapeutic agent, such as a cancer vaccine or NKT agonist. The invention also provides a method for treating cancer using an intracellular penetration enhancing agent. The methods of the invention aim to substantially kill and/or destroy the target tumor cells, as well as those cancerous cells that have metastasized to other parts of the body.

22 Claims, 10 Drawing Sheets

(56) References Cited

U.S. PATENT DOCUMENTS

| | | | |
|---|---|---|---|
| 9,351,997 B2 | 5/2016 | Bender | |
| 9,636,406 B2 | 5/2017 | Bender | |
| 2003/0203033 A1* | 10/2003 | Dang | A61K 9/0024 424/486 |
| 2007/0049557 A1 | 3/2007 | Ahmed et al. | |
| 2007/0071677 A1* | 3/2007 | Park | A61K 38/168 424/1.69 |
| 2008/0167217 A1* | 7/2008 | Rath | A61K 31/192 424/85.4 |
| 2009/0123562 A1* | 5/2009 | Bender | A61P 17/00 424/617 |
| 2009/0143330 A1 | 6/2009 | Levchik et al. | |
| 2009/0186802 A1 | 7/2009 | Alluis et al. | |
| 2009/0275654 A1 | 11/2009 | Brown | |
| 2011/0008369 A1* | 1/2011 | Finnefrock | C07K 16/2896 424/172.1 |
| 2011/0077297 A1* | 3/2011 | Jansen | A61K 9/0014 514/510 |
| 2011/0300223 A1 | 12/2011 | Nishio et al. | |
| 2013/0156859 A1 | 6/2013 | Koshi et al. | |

FOREIGN PATENT DOCUMENTS

| | | |
|---|---|---|
| WO | WO 1998/53799 | 12/1998 |
| WO | WO 99/16427 | 4/1999 |
| WO | WO 2001/034130 | 5/2001 |
| WO | WO 2003/007869 | 1/2003 |
| WO | WO 2004/081196 | 9/2004 |
| WO | WO 2005/107462 | 11/2005 |
| WO | WO 2005/117854 | 12/2005 |
| WO | WO 2006/072070 | 7/2006 |
| WO | WO 2008/095144 | 8/2008 |
| WO | WO 2011/084061 | 7/2011 |
| WO | WO 2011/112889 | 9/2011 |
| WO | WO 2012/026508 | 3/2012 |
| WO | WO-2014/018932 A2 | 1/2014 |
| WO | WO-2014/018932 A3 | 1/2014 |
| WO | WO 2014/046983 | 3/2014 |

OTHER PUBLICATIONS

A. A. Stavrovskaya et al., "The Effect of Non-ionic Detergent Tween 80 on Colcemid-Resistant Transformed Mouse Cells In Vitro," Int. J. Cancer: 15, 665-672 (1975).*

M. R. Infante et al., "Amino acid-based surfactants," C.R. Chimie 7 (2004) 583-592.*

Cemazar et al. "Intratumoral cisplatin administration in electrochemotherapy: antitumor effectiveness, sequence dependence and platinum content" Anti-Cancer Drugs, vol. 9, (1998), pp. 525-530.

Supplementary European Search Report for European Application No. 13838639.6, dated Apr. 1, 2016, 11 pages.

International Search Report and Written Opinion for International Application No. PCT/US2013/059841, dated Dec. 17, 2013, 8 pages.

Ajima, K. et al., "Enhancement of in vivo anticancer effects of cisplatin by incorporation inside single-wall carbon nanohoms," ACS Nano., 2(10):2057-2064 (Oct. 2008).

American Cancer Society, "Filgrastim," WayBack Macine [Online], <http://www.cancer.org/Treatment/TreatmentsandSideEffects/GuidetoCancerDrugs/filgrastim>, Mar. 28, 2011, 3 pages.

Amiji, M. M. et al., "Intratumoral administration of paclitaxel in an in situ gelling poloxamer 407 formulation," Pharmaceutical Development and Technology, 7(2):195-202 (May 2002).

Bajaj, G. et al., "Drug delivery systems for intraperitoneal therapy," Pharm Res. May 2010; 27(5):735-738. Epub Mar. 3, 2010.

Barth, R. F. et al., "Neutron capture therapy of epidermal growth factor (+) gliomas using boronated cetuximab (IMC-C225) as a derivery agent," Aoplied Radiation and Isotopes, 61:899-903 (2004).

Benoit, L. et al., "Intraperitoneal cisplatin plus epinephrine and surgical debulking for the treatment of advanced peritoneal carcinomatosis in the rat," Gastroenterol Clin Biol. Jan. 2000; 24(1):26-30.

Bloom, N. D. et al., "Enhancement of tumor blood flow and tumoricidal effect of doxorubicin by intraportal epinephrine in experimental liver metastasis," Arch Surg. Nov. 1987; 122(11):1269-1272.

Braumann, C. et al., "Local and systemic chemotherapy with taurolidine and taurolidine/heparin in colon cancer-bearing rats undergoing laparotomy," Clin Exp Metastasis, 2003; 20(5):387-394.

Castro, D. J. et al., "Intratumoral cisplatin/epinephrine gel in advanced head and neck cancer: a multicenter, randomized, double-blind, phase III study in North America," Head & Neck, Sep. 2003; 25(9):717-731.

Celikoglu, F. et al., "Techniques for intratumoral chemotherapy of lung cancer by bronchoscopic drug delivery," Cancer Therapy, 6:545-552 (2008).

Cheng, Y. et al., "Dendrimers as drug carriers: applications in different routes of drug administration," Journal of Pharmaceutical Sciences, 97(1):123-143 (Jan. 2008).

Choi, J. et al., "Intraperitoneal immunotherapy for metastatic ovarian carcinoma: Resistance of intratumoral collagen to antibody penetration," Clin Cancer Res., Mar. 15, 2006; 12(6):1906-1912.

Davidson, B. S. et al., "Collagen matrix cisplatin prevents local tumor growth after margin-positive resection," J Surg Res., Jun. 1995; 58(6):618-624.

Dimeco, F. et al., "Local delivery of mitoxantrone for the treatment of malignant brain tumors in rats," J Neurosurg. Nov. 2002; 97(5):1173-1178.

Duvillard, C. et al., "EDTA enhances the antitumor efficacy of intratumoral cisplatin in s.c. grafted rat colon tumors," Anticancer Drugs. Mar. 2004; 15(3):295-299.

Duvillard, C. et al., "Epinephrine enhances penetration and anticancer activity of local cisplatin on rat sub-cutaneous and peritoneal tumors," Int J Cancer. May 31, 1999; 81(5):779-784.

Duvillard, C. et al., "Phase 2 study of intratumoral cisplatin and epinephrine treatment for locally recurrent head and neck tumors," Ann Otol Rhinol Laryngol. Mar. 2004; 113(3 Pt 1):229-233.

Elvin, P. et al., "Anti-tumour activity of novel adducts of ascorbic acid with aldehydes," Eur J Cancer Clin Oncol. Jul. 1981; 17(7):759-765.

Engelmann, K. et al., "CT-guided percutaneous intratumoral chemotherapy with a novel cisplatin/epinephrine injectable gel for the treatment of inoperable malignant liver tumors," Rofo. Dec. 2000; 172(12):1020-1027 (English Abstract).

Esquis, P. et al., "High intra-abdominal pressure enhances the penetration and antitumor effect of intraperitoneal cisplatin on experimental peritoneal carcinomatosis," Ann Surg. Jul. 2006; 244(1):106-112.

Ewend, M. G. et al., "Local delivery of chemotherapy prolongs survival in experimental brain metastases from breast carcinoma," Neurosurgery, Nov. 1998; 43(5):1185-1193.

Favoulet, P. et al., "Pre-clinical study of the epinephrine-cisplatin association for the treatment of intraperitoneal carcinomatosis," Eur J Surg Oncol. Feb. 2001; 27(1):59-64.

Flessner, M. F. et al., "Resistance of tumor interstitial pressure to the penetration of intraperitoneally delivered antibodies into metastatic ovarian tumors," Clin Cancer Res. Apr. 15, 2005; 11(8):3117-3125.

González-Moreno, S. et al., "Hyperthermic intraperitoneal chemotherapy: Rationale and technique," World J Gastrointest Oncol. Feb. 15, 2010; 2(2):68-75.

Gondal, J. A. et al., "Comparative pharmacological, toxicological and antitumoral evaluation of free and liposome-encapsulated cisplatin in rodents," Eur. J Cancer, 29A(11):1536-1542 (1993).

Grant, S. C. et al., "Long survival of patients with small cell lung cancer after adjuvant treatment with the anti-idiotypic antibody BEC2 plus bacillus calmette-guerin," Clin. Cancer Res., 5:1319-1323 (1999).

Gupta, V. et al., "Reduction in cisplatin genotoxicity (micronucleus formation) in non target cells of mice by protransfenome gel formulation used for management of cutaneous squamous cell carcinoma," Acta Pharmaceutica, 61(1):63-71 (Mar. 2011).

(56) References Cited

OTHER PUBLICATIONS

Hamstra, D. A. et al., "Intratumoral injection of BCNU in ethanol (DTI-015) results in enhanced delivery to tumor—a pharmacokinetic study," J Neuro-Oncol. Jul. 2005; 73(3):225-238.

Holback, H. et al., "Intratumoral drug delivery with nanoparticulate carriers," Pharm Res. Aug. 2011; 28(8):1819-1830.

Hu-Lieskovan, S. et al., "Sequence-specific knockdown of EWS-FLI1 by targeted, nonviral delivery of small interfering RNA inhibits tumor growth in a murine model of metastatic ewing's sarcoma," Cancer Res., 85:8984-8992 (2005).

Hwang, T. L. et al., "Permeation enhancer-containing water-in-oil nanoemulsions as carriers for intravesical cisplatin delivery," Pharmaceutical Research, 26(10):2314-2323 (Oct. 2009).

Iinuma, H. et al., "Intracellular targeting therapy of cisplatin-encapsulated transferrin-polyethylene glycol liposome on peritoneal dissemination of gastric cancer," Int J Cancer. May 1, 2002; 99(1):130-137.

Ikeguchi, M. et al., "Cisplatin combined with prostaglandin E1 chemotherapy in rat peritoneal carcinomatosis," Int J Cancer. Nov. 1, 2000; 88(3):474-478.

Javadzadeh, Y. et al., "Enhancing percutaneous delivery of methotrexate using different types of surfactants," Colloids and Surfaces B: Biointerfaces, Feb. 1, 2011; 82(2):422-426.

Koizumi, W. et al., "S-1 plus cisplatin versus S-1 alone for first-line treatment of advanced gastric cancer (SPIRIS trial): a phase III trial," Lancet Oncol. Mar. 2008; 9(3):215-221. Epub Feb. 20, 2008.

Kumagai, S. et al., "Improvement of intraperitoneal chemotherapy for rat ovarian cancer using cisplatin-containing microspheres," Japan J Cancer Res. Apr. 1996; 87(4):412-417.

Landrito, J. E. et al., "Effects of intralesional injection of cisplatin dissolved in urografin and lipiodol on Ehrlich ascites tumor and normal tissues of CD-1 mice," Cancer Chemother Pharmacol. 1994; 34(4):323-330.

Leonetti, C. et al., "Increase of cisplatin sensitivity by c-myc antisense oligodeoxynucleotides in a human metastatic melanoma inherently resistant to cisplatin," Clin Cancer Res. Sep. 1999; 5(9):2588-2595.

Leung, T. W. T. et al., "Phase II study of the efficacy and safety of cisplatin-epinephrine injectable gel administered to patients with unresectable hepatocellular carcinoma," J Clin Oncol. Feb. 15, 2003; 21(4):652-658.

Liu, Y. et al., "Differential cytostatic effect of sodium salicylate in human colorectal cancers using an individualized histoculture system," Cancer Chemother Pharmacol. Jun. 2002; 49(6):473-478. Epub Apr. 24, 2002.

Liu, Z. et al., "Delivery of an anticancer drug and a chemosensitizer to murine breast sarcoma by intratumoral injection of sulfopropyl dextran microspheres," Journal of Pharmacy and Pharmacology 2003, 55:1063-1073.

Los, G. et al., "Platinum distribution in intraperitoneal tumors after intraperitoneal cisplatin treatment," Cancer Chemother Pharmacol. 1990; 25(6):389-394.

Los, G. et al., "Anti-tumor effect of cisplatin, carboplatin, mitoxantrone, and doxorubicin on peritoneal tumor growth after intraperitoneal and intravenous chemotherapy: a comparative study," Sel Cancer Ther. 1990 Summer; 6(2):73-82.

Los, G. et al., "Antitumour response and nephrotoxicity following intraperitoneal administration of a slow release formulation of cisplatin to rats bearing cancers restricted to the peritoneal cavity," Br J Cancer. Jul. 1991; 64(1):90-92.

Los, G. et al., "Direct diffusion of cis-diamminedichloroplatinum(II) in intraperitoneal rat tumors after intraperitoneal chemotherapy: a comparison with systemic chemotherapy," Cancer Res. Jun. 15, 1989; 49(12):3380-3384.

Los, G. et al., "The use of oxaliplatn versus cisplatin in intraperitoneal chemotherapy in cancers restricted to the peritoneal cavity in the rat," Cancer Lett. May 30, 1990; 51(2):109-117.

Malik, N. et al., "Dendrimier-platinate: a novel approach to cancer chemotherapy," Anticancer Drugs, Sep. 1999; 10(8):767-776 (Abstract).

Menjoge, A. R. et al., "Transport and biodistribution of dendrimers across human fetal membranes: Implications for intravaginal administration of dendrimer-drug conjugates," Biomaterials, 31:5007-5021 (2010).

"Lesion," Definition of Lesion by Medical Dictionary, Miller-Keane Encyclopedia and Dictionary of Medicine, Nursing, and Allied Health, Seventh Edition (2003) by Saunders, an imprint of Elsevier, Inc., 5 pages.

Malhotra, H. et al., "Cisplatin/epinephrine injectable gel," Drugs & Aging, 18(10):787-793 (2001).

Markman, M., "Intraperitoneal antineoplastic agents for tumors principally confined to the peritoneal cavity," Cancer Treatment Reviews, Dec. 1986; 13(4):219-242.

Masunaga, S. et al., "Enhancement of cisplatin sensitivity of quiescent cells in solid tumors by combined treatment with tirapazamine and low-temperature hyperthermia," Radiat Med. Nov.-Dec. 1998; 16(6):441-448.

Mohan, P. et al., "Doxorubicin as a molecular nanotheranostic agent: effect of doxorubicin encapsulation in micelles or nanoemulsions on the ultrasound-mediated intracellular delivery and nuclear trafficking," Mol Pharm. Dec. 6, 2010; 7(6):1959-1973.

Mok, T. S. K. et al., "Pharmacokinetic study of intralesional cisplatin for the treatment of hepatocellular carcinoma," Cancer, Jun. 15, 2001; 91(12):2369-2377.

Molucon-Chabrot, C. et al., "Feasibility of using intraperitoneal epinephrine and cisplatin in patients with advanced peritoneal carcinomatosis," Anti-Cancer Drugs. Nov. 2006; 17(10):1211-1217.

Monga, S. P. et al., "Intratumoral therapy of cisplatin/epinephrine injectable gel for palliation in patients with obstructive esophageal cancer," Am J Clin Oncol. Aug. 2000; 23(4):386-392.

Motlekar, N. A. et al., "Evaluation of the Oral Bioavailability of Low Molecular Weight Heparin Formulated With Glycyrrhetinic Acid as Permeation Enhancer," Drug Dev Res. Feb. 2006; 67(2):166-174.

Namur, J. et al., "Embolization of hepatocellular carcinoma with drug-eluting beads: doxorubicin tissue concentration and distribution in patient liver explants," J Hepatol. Dec. 2011; 55(6):1332-1338.

National Cancer Institute, Understanding Cancer Series: Cancer, "Slide 9: Malignant versus Benign Tumors," WayBack Machine [Online], <http://www.cancer.gov/cancertopics/understandingcancer/cancer/page9>, Mar. 28, 2011, 2 pages.

National Cancer Institute, Dictionary of Cancer Terms, "Solid Tumor," WayBack Machine [Online], <http://www.cancer.gov/dictionary?CdrID=45301 >, Mar. 27, 2011, 1 page.

Newman, M. S. et al., "Comparative pharmacokinetics, tissue distibution, and therapeutic effectiveness of cisplatin encapsulated in long-circulating, pegylated liposomes (SPI-077) in tumor-bearing mice," Cancer Chemother Pharmacol., 43(1):1-7 (Jan. 1999).

Okamoto, H. et al., "Local and systemic delivery of high-molecular weight drugs by powder inhalation," The Pharmaceutical Society of Japan, Apr. 2007; 127(4):643-653.

Okuyama, S. et al., "Intratumoral doxycycline for skin metastases of human malignancies," Tohoku J Exp Med. Feb. 1987; 151(2):241-244.

Onier, N. et al., "Cure of colon cancer metastasis in rats with the new lipid A OM 174. Apoptosis of tumor cells and immunization of rats," Clin Exp Metastasis. Jun. 1999; 17(4):299-306.

Ozols, R. F. et al., "Chemotherapy for Murine Ovarian Cancer: A Rationale for IP Therapy With Adriamycin," Cancer Treat Rep. Feb. 1979; 63(2):269-273.

Peaston, A. et al., "Treatment of superficial tumours on horses with dimethyl sulfoxide and cisplatin," Aust Vet J. Feb. 1995; 72(2):76-77.

Poirson-Bichat, F. et al., "Methionine depletion enhances the antitumoral efficacy of cytotoxic agents in drug-resistant human tumor xenografts," Clin Cancer Res. Feb. 2000; 6(2):643-653.

Ramesh, G. et al., "Salicylate reduces cisplatin nephrotoxicity by inhibition of tumor necrosis factor-alpha," Kidney Int. Feb. 2004; 65(2):490-499.

Rossi, C. R. et al., "Pharmacokinetics of intraperitoneal cisplatin and doxorubicin," Surg Oncol Clin N Am. Jul. 2003; 12(3):781-794.

(56) References Cited

OTHER PUBLICATIONS

Saad, M. et al., "Co-delivery of siRNA and an anticancer drug for treatment of multidrug-resistant cancer," Nanomedicine (Lond)., 3(6):761-776 (Dec. 2008).

Sawyer, A. J. et al., "Convection-enhanced delivery of camptothecin-loaded polymer nanoparticles for treatment of intracranial tumors," Drug Deliv Transl Res., Feb. 1, 2011; 1(1):34-42.

Settelen, N. et al., "Controlled plasmid gene transfer to murine renal carcinoma by hexadecylphosphocholine," Journal of Controlled Release, 94(1):237-244 (Jan. 2004).

Shen, Z. et al., "Intravesicle treatments of bladder cancer: review," Pharmaceutical Research, 25(7):1500-1510 (Jul. 2008).

Soloway, A. H. et al., "Penetration of Brain and Brain Tumors by Intravascular Injection of Alkylating Agents," J Med Pharm Chem. Nov. 1962; 91:1371-1376.

Speyer, J. L. et al., "Intraperitoneal carboplatin: rationale and experience," Semin Oncol. Feb. 1992; 19(1 Suppl 2):107-113.

Suzuki, K. et al., "A new drug delivery system for local cancer chemotherapy using cisplatin and chitin," Anticancer Res. Mar.-Apr. 1995; 15(2):423-426.

Tamura, T. et al., "Anti-tumor effect of intraperitoneal administration of cisplatin-loaded microspheres to human tumor xenografted nude mice," J Control Release, Apr. 23, 2002; 80(1-3):295-307.

Tao, W. et al., "Distribution of 5-fluorouracil in plasma and pancreatic tissue of rats during the regional arterial infusion chemotherapy," Zhongguo Yi Xue Ke Xue Yuan Xue Bao. Oct. 1999; 21(5):390-394 (English Abstract).

Théon, A. P. et al., "Long-term outcome associated with intratumoral chemotherapy with cisplatin for cutaneous tumors in equidae," 573 cases (1995-2004). J Am Vet Med Assoc. May 15, 2007; 230(10):1506-1513.

Toomey, P. et al., "Intralesional injection of rose bengal induces a systemic tumor-specific immune response in murine models of melanoma and breast cancer," PLOSOne [Online at www.plosone.org], 8(7):e68561, 6 pages.

Tong, A. W. et al., "Intratumoral injection of INGN 241, a nonreplicating adenovector expressing the melanoma-differentiation associated gene-7 (mda-7/IL24): biologic outcome in advanced cancer patents," Mol Ther. Jan. 2005; 11(1):160-172.

Tyler, B. et al., "A thermal gel depot for local delivery of paclitaxel to treat experimental brain tumors in rats," J Neurosurg. Aug. 2010; 113(2):210-217.

Tyler, B. M. et al., "Delayed onset of paresis in rats with experimental intramedullary spinal cord gliosarcoma following intratumoral administration of the paclitaxel delivery system," OncoGel., J Neurosurg Spine, Jan. 2012; 16(1):93-101.

Tzafriri, A. R. et al., "Diffusion-limited binding explains binary dose response for local arterial and tumour drug delivery," Cell Prolif. Jun. 2009; 42(3):348-363.

Van Putte, B. P. et al., "Combination chemotherapy with gemcitabine with isolated lung perfusion for the treatment of pulmonary metastases," J Thorac Cardiovasc Surg. Jul. 2005; 130(1):125-130.

Vincent, L. et al., "Efficacy of dendrimer-mediated angiostatin and TIMP-2 gene delivery on inhibition of tumor growth and angiogenesis: in vitro and in vivo studies,"Int. J. Cancer, 105(3):419-429 (Jun. 2003).

Vogl, T. J. et al., "CT-guided intratumoural administration of cisplatin/epinephrine gel for treatment of malignant liver tumours," Br J Cancer. Feb. 12, 2002; 86(4):524-529.

Weinberg, B. D. et al., "Antitumor efficacy and local distribution of doxorubicin via intratumoral delivery from polymer millirods," J Biomed Mater Res A. Apr. 2007; 81(1):161-170.

Weinberg, B. D. et al., "Model simulation and experimental validation of intratumoral chemotherapy using multiple polymer implants," Med Biol Eng Comput. Oct. 2008; 46(10):1039-1049.

Werner, J. A. et al., "A phase III placebo-controlled study in advanced head and neck cancer using intratumoural cisplatin/epinephrine gel," Br J Cancer. Oct. 21, 2002;87(9):938-944.

Wolinsky, J. B. et al., "Local drug delivery strategies for cancer treatment: gels, nanoparticles, polymeric films, rods, and wafers," J Control Release. Apr. 10, 2012; 159(1):14-26. Epub Dec. 1, 2011.

Wong, S-F., "Cetuximab: An Epidermal Growth Factor Receptor Monoclonal Antibody for the Treatment of Colorectal Cancer," Clinical Therapeutics, 27(6):684-694 (2005).

Yoshida, D. et al., "Dermatopharmacokinetics of salicylate following topical injection in rats: effect of osmotic pressure and injection volume on salicylate disposition," Int J Pharm. Jun. 7, 2007; 337(1-2):142-147.

Zahedi, P. et al., "An injectable depot system for sustained intraperitoneal chemotherapy of ovarian cancer results in favorable drug distribution at the whole body, peritoneal and intratumoral levels," J Control Release, Mar. 28, 2012; 158(3):379-385.

Zamboni, W. C. et al., "Inter- and intratumoral disposition of platinum in solid tumors after administration of cisplatin," Clin Cancer Res. Sep. 2002; 8(9):2992-2999.

Zheng, J. L. et al., "Distribution or 5-FU in rat plasma and liver tissue after local 5-FU infusion," J South Med University, May 2008; 28(5):823-827 (English Abstract).

Zhong, H. et al., "Low-Dose Paclitaxel Prior to intratumoral Dendritic Cell Vaccine Modulates intratumoral Cytokine Network and Lung Cancer Growth," Clin. Cancer Res., 13(18):5455-5462 (Sep. 2007).

Li, X. et al., "Superior antitumor efficacy of cisplatin-loaded nanoparticles by intratumoral delivery with decreased tumor metabolism rate," European Journal of Pharmaceutics and Biopharmaceutics, 70 (2008) 726-734.

Huang et al., "Cisplatin pretreatment enhances anti-tumor activity of cytokine-induced killer cells" *World Journal of Gastroenterology* vol. 17, No. 25, (2011): 3002-3011.

Chissov, V.I., ed. et al. (2008). Oncology. National Guidebook, pp. 105-111 and 385-393, 38 total pages (with English translation).

Oratz et al., "Intratumoral cisplatin/adrenaline injectable gel for the treatment of patients with cutaneous and soft tissue metastases of malignant melanoma" *Melanoma Research*, vol. 13, No. 1, (2003): 59-66.

Alani and Robinson, "Mechanistic Understanding of Oral Drug Absorption Enhancement of Cromolyn Sodium by an Amino Acid Derivative" *Pharmaceutical Research*, vol. 25, No. 1 (2008): 48-54.

\* cited by examiner

METHOD OF TREATING CANCER

CROSS-REFERENCE TO RELATED APPLICATIONS

This application is a continuation of U.S. Ser. No. 15/052,326, filed Feb. 24, 2016, which is a continuation of U.S. Ser. No. 14/280,036, filed May 16, 2014, now U.S. Pat. No. 9,351,997, which is a continuation of PCT/US2013/05984, filed Sep. 15, 2013, which claims priority to, and the benefit of, U.S. Ser. No. 61/779,509, filed Mar. 13, 2013, U.S. Ser. No. 61/707,733, filed Sep. 28, 2012, and U.S. Ser. No. 61/703,890, filed Sep. 21, 2012. Each of these applications is hereby incorporated by reference in their entirety.

FIELD OF THE INVENTION

The present invention relates to novel methods for treating cancer. The methods involve treating a carcinoma or sarcoma using a coadministration strategy that combines local codelivery of a therapeutic agent and an intracellular penetration enhancing agent, optionally in combination with at least one additional therapeutic agent (e.g., local or systemic administration of an immunotherapeutic agent). The methods of the invention reduce the growth, shrink, and/or eradicate a target tumor, as well as those cancerous cells that have metastasized to other parts of the body.

BACKGROUND OF THE INVENTION

It is currently believed that cancer cells routinely arise in our bodies but are continuously destroyed by a healthy immune system. It is thought that cancer tumors form when the immune system fails to destroy these routinely formed diseased cells. The word "cancer" is used to describe a number of diseases in which there is uncontrolled division of abnormal cells. Cancer may initially arise in virtually any tissue or organ in the body and forms as a result of a complex interaction of both innate genetic factors and environmental factors, such as one's diet or exposure to radiation, toxins, and the like. Despite advances in medicine and the understanding of the molecular basis of cancer, the exact causes of any given type of cancer are largely unknown, especially in a particular individual. Given this lack of knowledge, it is not surprising that it remains highly difficult to find effective cancer treatments.

Finding effective treatments is also made challenging because cancer often develops resistance to various therapeutic strategies. In addition, effective means for treating cancer become an even greater challenge in view of the capacity for certain types of cancers to spread from their primary source. This process, called metastasis, enables cancer cells to spread to other vital parts of the body through the blood and lymph systems. Some experts estimate that only a single cell in a million can survive long enough to help form a metastatic tumor. These odds are thought to be attributable to the challenges metastasized cells face in the destination tissue, including lodging in the destination tissue, overcoming local immune defenses, and acquiring their own blood supply and nutrients through the process of angiogenesis. Nevertheless, metastasis remains a key reason why effective cancer treatments are difficult to develop.

Existing cancer therapies today include multiple different ablation techniques such as surgical procedures; cryogenic or heat methods on the tissue, ultrasound, radiofrequency, and radiation; chemical methods such as pharmaceuticals, cytotoxic agents, monoclonal antibodies; or transarterial chemo immobilization (TACE), and combinations thereof pursuant to specific regimens based on the specific type and stage of cancer under treatment. However, these therapies are associated with substantially high costs. In addition, current treatment options are highly invasive, are associated with significant toxicities, and result in an overall poor quality of life for patients.

Standard of care cancer therapies typically couple surgical removal of the affected tissue with chemotherapy or radiation treatments. Standard approaches for administering chemotherapeutics are through the blood, e.g., systemic delivery, which can be achieved by various routes such as intravenous and/or gastrointestinal delivery. However, toxicity is a major drawback associated with systemically delivered chemotherapeutic drugs. Standard of care surgical treatments also introduce problems, including dislodgement of cancer cells into the blood and/or lymph systems, which results in the opportunity for cancer cells to metastasize to other sites in the body and cause additional tumors to form.

When surgery is not possible, the accepted treatment for cancer is to use radiation or chemotherapy. But survival rates for inoperable cancer are low when compared to the survival rate for cancers that are surgically removed prior to chemotherapy or radiation.

Regional chemotherapy represents a recent advance in the chemotherapeutic treatment of cancer. This approach involves delivering the chemotherapeutic agent directly to the tumor, e.g., proximal to, adjacent to, or intratumorally, as opposed to introducing the toxic agent into the bloodstream. One goal of regional chemotherapy is to minimize the toxic side effects typically associated with systemic chemotherapeutic administration.

However, regional chemotherapeutic approaches generally have not been satisfactory. A general problem with chemotherapy—including regional chemotherapy—is that cancer cells are highly resistant to penetration by chemotherapeutic agents. For example, certain platinum compounds are mainly taken into cancer cells by an active transport process using the CTR1 pathway (see Holzer et al., *Molecular Pharmacology* 70:1390-1394 (2006)). In addition, chemotherapeutic agents generally are delivered by the blood, they should be soluble in the blood, making them generally water soluble. Water soluble materials such as chemotherapeutic agents do not effectively pass through lipid cell membranes passively, and thus, are not readily deliverable to the intracellular space of cancer cells especially at low concentrations. Further, once inside, tumor cells have mechanisms and various processes designed to excrete the chemotherapeutic agents. For example, tumor cells are able to rid themselves of chemical agents using glutathione and/or metallothioneins complexing and have innate DNA repair mechanisms to overcome chemotherapies.

Certain cancer tumors resemble the body's tissue and thus diminish the immune system's otherwise innate ability to identify and kill them. Several cancer-fighting technologies (e.g., cancer vaccines) aim to stimulate the immune system against cancerous cells. Although one such product is currently approved for use (PROVENGE® by Dendreon Corporation, which is used against prostate cancer), the success of cancer vaccines has been limited. As tumor cells are derived from the individual with cancer, tumor cells are very similar to a person's own cells. The immune system's ability to mount an attack on the tumor cell is hindered because the tumor cell displays few, if any, antigens that are foreign to that individual. In addition, a tumor can have many different types of cells in it. Each cell type has different cell-surface antigens, again thwarting attack by the immune system. Moreover, tumors can secrete cytokines that directly inhibit immune activity. Finally, depending on disease stage, the tumor may be too advanced (e.g., bulky) for the vaccine to be effective. These, as well as other factors, are why tumors may lack sufficient amounts of antigens (or targets) needed to stimulate a sufficient immune system.

That said, it is generally the case that if cancer is detected early, the standard treatments against cancer can be highly effective. However, even when the best results are obtained, such treatments are invasive, toxic and damaging to the body and mentally demanding on the patient. If cancer is detected in late stage, few treatments offer the patient much hope of long term survival.

Thus, there continues to be a need in the art to identify and develop new cancer-fighting strategies that are more effective at treating disease, and which present lower costs to individuals and society in general.

SUMMARY OF THE INVENTION

There is disclosed herein a method for treating cancer. In aspects, the invention provides methods for effectively treating a solid tumor by locally coadministering (e.g., proximally, locally, directly into, and the like) a combination of a therapeutic agent (e.g., a small molecule, pharmaceutical drug, antibody, and the like) together with an intracellular penetration enhancing agent. The therapeutic agent and the intracellular penetration enhancing agent are administered in amounts and/or in a regimen that results in substantial tumor shrinkage and/or destruction. The exact administration regimen may vary, including that the agents may be delivered at the same time or concomitant with one another (e.g., same injection), or at different times and in any order. In addition, the administration regimen may involve multiple repetitions or rounds of administration, wherein the agents are delivered in the same or different fashions multiple times in a single day or on separate days.

Administration of repetitive dosing for a defined period of time is often referred to as a drug cycle. The methods described may also involve multiple drug cycles. The methods may also vary depending on the tumor type. The method of the invention also involves enhancing the treatment effects of the therapeutic agent and intracellular penetration enhancing agent by coupling their local administration with the administration of an immune-stimulating agent, such as a cancer vaccine or T-cell agonist, which may be delivered prior to, at or about the same time, or subsequent to the therapeutic and intracellular penetration enhancing agents. In embodiments, the therapeutic agent may be a combination of two or more agents selected from the group consisting of a chemotherapeutic agent, an antibody, and a nucleic acid molecule.

In one embodiment, the method of the invention can also be thought of as a two-phase therapeutic approach. In the first phase, a subject is locally coadministered both a therapeutic agent and an intracellular penetration enhancing agent in accordance with an effective dosing regimen. For example, the agents may be delivered at the same time, or at approximately the same time, to a bodily location that is in the same region as the target tumor, or which is at the perimeter of the target tumor, or which is within (intratumoral) the tumor itself. The intracellular penetration enhancing agent surprisingly and unexpectedly results in a substantially high increase in drug permeability of the therapeutic agent into the tumor cells. In the second phase, which can overlap, precede, or succeed the first phase, an immune-stimulating agent, such as a cancer vaccine, CD4 or NKT cell stimulating agent or combination of agents, is administered locally to the subject. However, it was unexpectedly found that the intracellular penetration agent in combination with certain cytotoxic drug agents elicits an immune response when administered intratumorally, even in the absence of additional immune stimulating agents. The invention also provides formulations for use in treating cancer in accordance with the methods of the invention. The formulations combine, separately or together, a therapeutic agent and an intracellular penetration enhancing agent. Such formulations may be administered locally or regionally, or intratumorally to a tumor in a subject. In certain embodiments, the invention provides formulations that further combine, separately or together, a therapeutic agent, an intracellular penetration enhancing agent, and an immunotherapeutic agent, e.g., a cancer vaccine. Such formulations may be administered locally or regionally, or intratumorally to a tumor in a subject.

Accordingly, in aspects, the invention provides methods for treating a subject in need thereof (e.g., a subject with one or more tumors) with an effective amount of a therapeutic agent and an intracellular permeation enhancing agent. In embodiments, administration of the intracellular permeation agent increases the likelihood of effectiveness of the therapeutic agent. In related embodiments, administration of the intracellular permeation agent increases the likelihood of effectiveness of the therapeutic agent by at least 10%, 20%, 30%, 40%, 50%, 60%, 70%, 80%, 90%, 95%, 99% or more (or any number therebetween) as compared to treatment without the intracellular permeation agent.

In another aspect, the invention provides methods for reducing the side effects of a therapeutic agent. In embodiments, the methods involve administering an effective amount of the therapeutic agent and an intracellular permeation enhancing agent to a subject (e.g., a subject with a tumor).

In yet another aspect, the invention provides methods for destroying cancerous cells within a subject (e.g., a subject with one or more tumors). In embodiments, the methods involve administering an effective amount of a therapeutic agent and an intracellular permeation enhancing agent.

In a further aspect, the invention provides methods for treating a tumor in a subject. In embodiments, the methods involve administering an effective amount of a therapeutic agent and an intracellular permeation enhancing agent.

In other aspects, the invention provides methods for inhibiting growth of a tumor in a subject. In embodiments, the methods involve administering an effective amount of a therapeutic agent and an intracellular permeation enhancing agent.

In any of the above aspects and embodiments, the therapeutic agent can be locally, regionally, or systemically administered to the subject.

In any of the above aspects and embodiments, the intracellular permeation enhancing agent can be locally or regionally administered to the subject.

In embodiments, the methods involve locally or regionally coadministering to the subject a therapeutic agent and an intracellular permeation enhancing agent.

In embodiments, the tumor is a solid tumor. In some embodiments, the tumor has metastasized.

In embodiments, the tumor is a carcinoma or sarcoma. In related embodiments, the tumor is a carcinoma or sarcoma of the skin, bone, muscle, breast, oral cavity, colon, organ, kidney, liver, lung, gallbladder, pancreas, brain, esophagus, bladder, large intestine, small intestine, spleen, stomach, prostate, testes, ovaries, or uterus. In certain embodiments, the tumor is a carcinoma of the pancreas, colon, or liver.

In embodiments, the therapeutic agent is administered intratumorally and/or the intracellular permeation enhancing agent is administered intratumorally. In some embodiments, the therapeutic agent is administered systemically and the intracellular permeation enhancing agent is administered intratumorally.

In any of the above aspects and embodiments, the methods may reduce the growth of the one or more tumors, shrink the one or more tumors, or eradicate the one or more tumors. For example, the tumor mass does not increase. In certain embodiments, the tumor shrinks by 10%, 25%, 50%, 75%, 85%, 90%, 95%, or 99% or more (or any number therebetween) as compared to its original mass.

In any of the above aspects and embodiments, the methods may prevent tumor metastasis.

In any of the above aspects and embodiments, the effective amount of the therapeutic agent can be selected based on the volume and type of the tumor.

In any of the above aspects and embodiments, the effective amount of the intracellular permeation enhancing agent and/or drug agent can be selected based on the volume and type of the tumor.

In embodiments, the methods involve administering the therapeutic agent on a first day and repeating the administration on one or more subsequent days. In related embodiments, the first day and one or more subsequent days are separated by between 1 day and about 3 weeks.

In embodiments, the methods involve administering the intracellular permeation enhancing agent on a first day and repeating the administration on one or more subsequent days. In related embodiments, the first day and one or more subsequent days are separated by between 1 day and about 3 weeks. In another embodiment, the intracellular permeation enhancing agent may be administered between 3 and 5 days consecutively or with one day of rest within the period.

In certain embodiments, the methods involve coadministering the therapeutic agent and the intracellular permeation enhancing agent on the first day and repeating the administration on one or more subsequent days. In related embodiments, the first day and one or more subsequent days are separated by between 1 day and about 3 weeks.

In some embodiments, the therapeutic agent and the intracellular permeation enhancing agent are coadministered in a ratio of about 1:2, 1:4, 1:10, 1:20, 1:25, 1:50, 1:100, or 1:200 (weight ratio of therapeutic agent:intracellular permeation enhancing agent).

In some embodiments, the intracellular permeation enhancing agent is administered at a concentration of between about 0.5 mgs per ml and about 50 mgs per ml. In still other embodiments, the intracellular permeation enhancing agent is administered at a concentration of between about 10 mgs per ml and about 30 megs per ml.

In certain embodiments, the therapeutic agent and the intracellular permeation enhancing agent are delivered simultaneously in a single formulation or simultaneously in separate formulations. In other embodiments, the intracellular permeation enhancing agent is administered before the therapeutic agent.

In any of the above aspects and embodiments, the therapeutic agent can be an anticancer agent.

In some embodiments, the anticancer agent is a chemotherapeutic agent (e.g., Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, a salt thereof, or any combination of the foregoing.

In other embodiments, the therapeutic agent is a therapeutic antibody or a combination of two or more therapeutic antibodies (e.g., Abagovomab, Alacizumab pegol, Alemtuzumab, Altumomab pentetate (Hybri-ceaker), Amatuximab, Anatumomab mafenatox, anti-PD-1 antibodies, Apolizumab, Arcitumomab (CEA-Scan), Belimumab, Bevacizumab, Bivatuzumab mertansine, Blinatumomab, Brentuximab vedotin, Cantuzumab mertansine, Cantuzumab ravtansine, Capromab pendetide (Prostascint), Catumaxomab (Removab), Cetuximab (Erbitux), Citatuzumab bogatox, Cixutumumab, Clivatuzumab tetraxetan (hPAM4-Cide), Conatumumab, Dalotuzumab, Denosumab, Drozitumab, Edrecolomab (Panorex), Enavatuzumab, Gemtuzumab, Ibritumomab tiuxetan, Ipilimumab (MDX-101), Ofatumumab, Panitumumab, Rituximab, Tositumomab, Trastuzumab, or any combination thereof).

In yet another embodiment, the therapeutic agent is a nucleic acid molecule. For example, the nucleic acid molecule can be an interfering RNA (e.g., RNAi or shRNA), a gene therapy expression vector, or a gene silencing vector.

In certain embodiments, the therapeutic agent is a radioisotope.

In certain embodiments, the therapeutic agent is a thymidylate synthase inhibitor. In certain embodiments, the therapeutic agent is a platinum compound.

In certain embodiments, the therapeutic agent is a vinca alkaloid agent.

In any of the above aspects and embodiments, the intracellular permeation enhancing agent can be a chemical compound that enhances passive transport of the therapeutic compound into a cell.

In embodiments, the intracellular permeation enhancing agent is a functionalized ketoacid, 6-Oxo-6-phenylhexanoic acid, 8-Oxo-8-phenyloctanoic acid, 8-(2,5-Dichlorophenyl)-8-oxooctanoic acid, a functionalized ketoester or aldehyde, a modified amino acid, modified amino acids, N-[8-(2-hydroxybenzoyl)aminooctanoic acid, N-[8-(2-hydroxybenzoyl)aminodecanoic acid, N-(5-chlorosalicyloyl)-8-aminocaprylic acid, N-[4-(4-chloro-2hydroxybenzoyl)amino1 butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy]hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid, octisalate, a diketopiperazines, saponin, an acylcarnitine, an alkanoylcholine, a taurodihydrofusidate, a sulphoxide, an oxazolidinone, a pyrrolidone, an alcohol or alkanol, a benzoic acid, a glycol, a surfactant, a terpene, a functionally effective salt of any of the foregoing, a derivative of any of the foregoing, or combinations thereof.

In some embodiments, the intracellular permeation enhancing agent is 6-Oxo-6-phenylhexanoic acid, 8-Cyclohexyl-8-oxooctanoic acid, N-[8-(2-hydroxybenzoyl)aminooctanoic acid, a functionally effective salt of any of the foregoing, a derivative of any of the foregoing, or any combination thereof.

In certain embodiments, the therapeutic agent is cisplatin or other platinum agent (e.g., satraplatin, pcioplatin, nedaplatin, triplatin, carboplatin or oxaplatin), and wherein the intracellular permeation enhancing agent is 6-oxo-6 phenylhexanoic acid, N-[8-(2-hydroxybenzoyl)aminooctanoic acid, a salt or derivative of any of the foregoing, or any combination thereof.

In embodiments, the above methods further involve administering a therapeutically effective amount of an immunotherapeutic agent. In some embodiments, the immunotherapeutic agent is a cancer vaccine, hormone, epitope, cytokine, tumor antigen, CD4 cell stimulator, NKT cell agonist, or adjuvant. For example, the immunotherapeutic agent can be an interferon, interleukin, tumor necrosis factor, ovalbumin, Neuvenge®, Oncophage, CimaVax-EGF, Mobilan, α-Gal glycolipid, α-Galactosylceramide (α-GalCer), β-mannosylceramide (β-ManCer), adenovirus delivered vaccines, Celldex's CDX1307 and CDX1401; GRNVAC1, viral based vaccines, MVA-BN, PROSTVAC®, Advaxis'; ADXS11-001, ADXS31-001, ADXS31-164, BiovaxID, folate binding protein (E39), Granulocyte macrophage colony stimulating factor (GM-CSF) with and without E75 (NeuVax) or OncoVEX, trastuzumab, Ae-37, IMA901, SC1B1, Stimuvax, peptides that can elicit cytotoxic lymphocyte response, peptide vaccines including telomerase peptide vaccine (GV1001), survivin peptide, MUC1 peptide, ras peptide, TARP 29-37-9V Peptide epitope enhanced peptide, DNA Vector pPRA-PSM with synthetic peptides E-PRA and E-PSM; Ad.p53 DC vaccine, NY-ESO-1 Plasmid DNA (pPJV7611), genetically modified allogeneic (human) tumor cells for the expression of IL-1, IL-7, GM-CSF, CD80 or CD154, HyperAcute®-Pancreatic cancer vaccine (HAPa-1 and HAPa-2 components), Melaxin (autologous dendritoma vaccine) and BCG, GVAX (CG8123), CD40 ligand and IL-2 gene modified autologous skin fibroblasts and tumor cells, ALVAC-hB7.1, Vaximm Gmbh's VXM01, Immunovative Therapies' AlloStim-7, ProstAtak™, TG4023 (MVA-FCU1), Antigenic's HSPPC-96, Immunovaccine Technologies' DPX-0907 which consists of specific HLA-A2-restricted peptides, a universal T Helper peptide, a polynucleotide adjuvant, a liposome and Montanide (ISA51 VG), GSK2302032A, Memgen's ISF35, Avax's OVax: Autologous, DNP-Modified Ovarian vaccine, Theratope®, Ad100-gp96Ig-HLA A1, Bioven's recombinant Human rEGF-P64K/Montanide vaccine, TARP 29-37, or Dendreon's DN24-02.

In certain embodiments, the immunotherapeutic agent is an α-Gal glycolipid.

In certain embodiments, the immunotherapeutic agent is a β-ManCer comprising a sphingosine moiety and a fatty acid moiety comprising a linear or branched, saturated or unsaturated, aliphatic hydrocarbon group having from about 8 to about 49 carbon atoms. In related embodiments, the fatty acid moiety comprises a linear or branched, saturated or unsaturated, aliphatic hydrocarbon group having from about 8 to about 15 carbon atoms. In other related embodiments, the fatty acid moiety comprises a linear or branched, saturated or unsaturated, aliphatic hydrocarbon group having from about 18 to about 30 carbon atoms. The β-ManCer comprises the following structure:

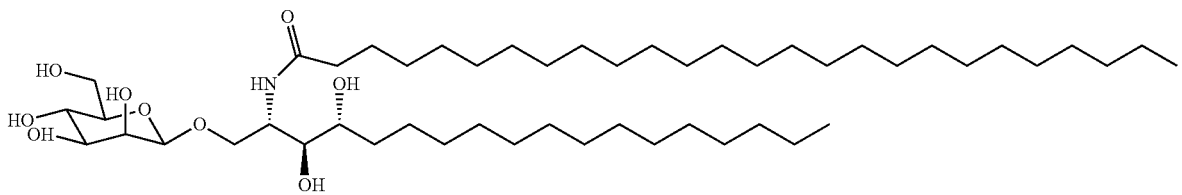 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

In the above embodiments, the immunotherapeutic agent enhances the therapeutic effects of the therapeutic agent. For example, the immunotherapeutic agent further reduces the growth of the tumor or further shrinks the tumor.

In some embodiments, the immunotherapeutic agent is administered after administration of the therapeutic agent and the intracellular permeation enhancing agent. In other embodiments, the immunotherapeutic agent is administered simultaneously with the first administration of the therapeutic agent and the intracellular permeation enhancing agent.

In embodiments, the immunotherapeutic agent is administered locally, regionally, or systemically. For example, the immunotherapeutic agent can be administered intraperitoneally. The immunotherapeutic agent can also be administered intratumorally.

In any of the above aspects and embodiments, the therapeutic agent and the intracellular permeation enhancing agent can be coupled.

In aspects, the above methods can further involve administering a standard of care therapy to the subject. In embodiments, the standard of care therapy is surgery, radiation, radio frequency, cryogenic, ultranoic ablation, systemic chemotherapy, or a combination thereof.

In any of the above aspects and embodiments, administration of the therapeutic agent, the intracellular permeation enhancing agent, or the immunotherapeutic agent can be conducted with the aid of an imaging system (e.g., X-ray computed tomography (CT), fluoroscopy, magnetic resonance imaging (MRI), ultrasound, or positron emission tomography (PET)/computed tomography (CT)).

In other aspects, the invention includes methods of imaging one or more tumors with an imaging system selected from the group consisting of X-ray computed tomography (CT), fluoroscopy, magnetic resonance imaging (MRI), ultrasound, and positron emission tomography (PET)/computed tomography (CT), determining the volume of the one or more tumors; and calculating, based on the determined tumor volume, a therapeutically effective tumor-specific dose amount of the therapeutic agent and the intracellular permeation enhancing agent. In certain embodiments, each or some of the one or more tumors may be intratumorally co-administered with the therapeutically effective tumor-specific dose of the therapeutic agent and the intracellular permeation enhancing agent calculated for that tumor.

In any of the above aspects and embodiments, the subject can be a mammal (e.g., human, dog, cat, horse, cow, sheep, goat, pig, mouse, rat, guinea pig, or monkey).

The invention also features methods of treating a subject in need thereof (e.g., a subject having a tumor) with an effective amount of an intracellular permeation enhancing agent.

In some aspects, the invention provides methods for destroying cancerous cells within a subject (e.g., a subject having a tumor). In embodiments, the methods involve administering an effective amount of an intracellular permeation enhancing agent.

In certain aspects, the invention provides methods for treating a tumor in a subject. In embodiments, the methods involve administering an effective amount of an intracellular permeation enhancing agent.

In certain aspects, the invention provides methods for inhibiting growth of a tumor in a subject. In embodiments, the methods involve administering an effective amount of an intracellular permeation enhancing agent.

In any of the above aspects and embodiments, the intracellular permeation enhancing agent can be locally or regionally administered to the subject.

In embodiments, the tumor is a solid tumor. In some embodiments, the tumor has metastasized.

In embodiments, the tumor is a carcinoma or sarcoma. In related embodiments, the tumor is a carcinoma or sarcoma of the skin, bone, muscle, breast, oral cavity, organ, kidney, liver, lung, gallbladder, pancreas, brain, esophagus, bladder, large intestine, small intestine, spleen, stomach, prostate, testes, ovaries, or uterus. In certain embodiments, the tumor is a carcinoma or sarcoma of the pancreas.

In embodiments, the intracellular permeation enhancing agent is administered intratumorally.

In the above aspects and embodiments, the methods may reduce the growth of the tumor, shrinks the tumor, or eradicates the tumor. For example, the tumor mass does not increase. In certain embodiments, the tumor shrinks by 10%, 25%, 50%, 75%, 85%, 90%, 95%, or 99% or more (or any number therebetween) as compared to its original mass.

In the above aspects and embodiments, the methods may prevent tumor metastasis. In any of the above aspects and embodiments, the effective amount of the intracellular permeation enhancing agent can be selected based on the volume and type of the tumor.

In embodiments, the methods involve administering the intracellular permeation enhancing agent on a first day and repeating the administration on one or more subsequent days. In related embodiments, the first day and one or more subsequent days are separated by between 1 day and about 3 weeks.

In the above aspects and embodiments, the intracellular permeation enhancing agent can be a chemical compound that enhances passive transport of the therapeutic compound into a cell.

In embodiments, the intracellular permeation enhancing agent is a functionalized ketoacid, 6-Oxo-6-phenylhexanoic acid, 8-Oxo-8-phenyloctanoic acid, 8-(2,5-Dichlorophenyl)-8-oxooctanoic acid, a functionalized ketoester or aldehyde, a modified amino acid, modified amino acids, N-[8-(2-hydroxybenzoyl)aminooctanoic acid, N-[8-(2-hydroxybenzoyl)aminodecanoic acid, N-(5-chlorosalicyloyl)-8-aminocaprylic acid, N-[4-(4-chloro-2hydroxybenzoyl)amino1 butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy]hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid, octisalate, a diketopiperazines, saponin, an acylcarnitine, an alkanoylcholine, a taurodihydrofusidate, a sulphoxide, an oxazolidinone, a pyrrolidone, an alcohol or alkanol, a benzoic acid, a glycol, a surfactant, a terpene or a functionally effective salt, derivative or combination thereof.

In some embodiments, the intracellular permeation enhancing agent is 6-Oxo-6-phenylhexanoic acid, 8-Cyclohexyl-8-oxooctanoic acid, N-[8-(2-hydroxybenzoyl)aminooctanoic acid, or a functionally effective salt or derivative thereof.

In the above aspects and embodiments, the subject can be a mammal (e.g., human, dog, cat, horse, cow, sheep, goat, pig, mouse, rat, guinea pig, or monkey).

The invention further features pharmaceutical compositions for conducting the method described herein. In embodiments, the composition is optimized for intratumoral administration. In other embodiments, the intracellular permeation enhancing agent and the therapeutic agent are coadministered intratumorally. These and other embodiments are disclosed or are obvious from and encompassed by, the following detailed description.

DEFINITIONS AND USE OF TERMS

The present invention may be understood more readily by reference to the following detailed description of the invention and the Examples included therein. Before the present methods and techniques are disclosed and described, it is to be understood that this invention is not limited to specific analytical or synthetic methods as such may, of course, vary.

It is also to be understood that the terminology used herein is for the purpose of describing particular embodiments only and is not intended to be limiting. Unless defined otherwise, all technical and scientific terms used herein have the meaning commonly understood by one of ordinary skill in the art to which this invention belongs.

By "agent" or "therapeutic agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease or a symptom thereof.

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

As used herein "an interfering RNA" refers to any double stranded or single stranded RNA sequence, capable—either directly or indirectly (i.e., upon conversion)—of inhibiting or down regulating gene expression by mediating RNA interference. Interfering RNA includes but is not limited to small interfering RNA ("siRNA") and small hairpin RNA ("shRNA"). "RNA interference" refers to the selective degradation of a sequence-compatible messenger RNA transcript.

As used herein "an shRNA" (small hairpin RNA) refers to an RNA molecule comprising an antisense region, a loop portion and a sense region, wherein the sense region has complementary nucleotides that base pair with the antisense region to form a duplex stem. Following post-transcriptional processing, the small hairpin RNA is converted into a small interfering RNA by a cleavage event mediated by the enzyme Dicer, which is a member of the RNase III family.

As used herein "an RNAi" (RNA interference) refers to a post-transcriptional silencing mechanism initiated by small double-stranded RNA molecules that suppress expression of genes with sequence homology.

As used herein "anti-tumor therapy" refers to any therapy to decrease tumor growth or metastasis, including surgery, radiation, and/or chemotherapy.

As used herein, "changed as compared to a control" sample or subject is understood as having a level of the analytic or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analytic substance can be a naturally occurring substance that is characteristically expressed or produced by the cell or organism (e.g., antibodies, pathogenic peptides or particles, and the like) or a substance produced by a reporter construct (e.g., β-galactosidase or luciferase). Depending on the method used for detection the amount and measurement of the change can vary. Determination of statistical significance is within the ability of those skilled in the art.

As used herein, the term "co-administering," or "co-administration," and the like refers to the act of administering two or more agents (e.g., a therapeutic agent with a penetration enhancer), compounds, therapies, or the like, at or about the same time. The order or sequence of administering the different agents of the invention, e.g., chemotherapeutics, intracellular permeation enhancing agents, or immunotherapeutic agents, may vary and is not confined to any particular sequence. Co-administering may also refer to the situation where two or more agents are administered to different regions of the body or via different delivery schemes, e.g., where a first agent is administered systemically and a second agent is administered intratumorally, or where a first agent is administered intratumorally and a second agent is administering systemically into the blood or proximally to the tumor. Co-administering may also refer to two or more agents administered via the same delivery scheme, e.g., where a first agent is administered intratumorally and a second agent is administered intratumorally.

As used herein, the terms "comprises," "comprising," "containing" and "having" and the like are open-ended as defined by U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Contacting a cell" is understood herein as providing an agent to a cell e.g., a cell to be treated in culture, ex vivo, or in an animal, such that the agent can interact with the cell (e.g., cell to be treated), potentially be taken up by the cell, and have an effect on the cell. The agent (e.g., an adjuvant) can be delivered to the cell directly (e.g., by addition of the agent to culture medium or by injection into the cell, tissue, or tumor of interest), or by delivery to the organism by a topical or parenteral route of administration for delivery to the cell by vascular, lymphatic, or other means. One of ordinary skill in the art will readily understand that administration of a therapeutic agent to a subject involves contacting the therapeutic agent with a cell, tumor, or tissue of the subject.

As used herein, the term "coupled," as in reference to two or more agents being "coupled" together, refers to a covalent or otherwise stable association between the two or more agents. For example, a therapeutic agent may be coupled with an intracellular permeation enhancing agent via a covalent bond, a covalently tethered linker moiety, or non-covalently through ionic interactions or hydrogen bonding. One or more agents that are coupled together retain substantial their same independent functions and characteristics. For example, the therapeutic agent when coupled to another agent may retain its same activity as if it were independent.

By "cycle" or "drug cycle" is meant the administration of repetitive dosing for a defined period of time, which may range from minute to hours to days to weeks to months or even years.

By "cytokine" is meant a hormone that acts locally and that modulates an individual's immune response.

As used herein, a "cytotoxic agent" refers to any agent capable of destroying cells, preferably dividing cells such as cancer cells.

As used herein, "detecting", "detection" and the like are understood that an assay performed to determine one or more characteristics of a sample, e.g. identifying the presence, absence or amount of the analyte to be detected. For example, detection can include identification of a specific analyte in a sample or an activity of an agent in a sample. Detection can include the determination of the presence of nucleic acid, protein (e.g., antibody, cytokine, and the like) by PCR, immunoassay (e.g., ELISA), microscopy, pathogen challenge, and the like. The amount of analyte or activity detected in the sample can be none or below the level of detection of the assay or method.

By "disease" is meant any condition or disorder that damages or interferes with the normal function of a cell, tissue, or organ. An exemplary disease is cancer.

The terms "effective amount", "therapeutically effective amount" or "pharmaceutically effective amount" as used herein, refer to an amount of an agent or compound that is sufficient to treat a disorder, e.g., a cancer. In some embodiments, the result is a reduction in and/or alleviation of the signs, symptoms, or causes of a disorder, or any other desired alteration of a biological system. For example, an "effective amount" for therapeutic uses is the amount of the composition comprising a compound as disclosed herein required to provide a clinically significant decrease in a disorder. An "effective amount" or therapeutically effective amount of an agent or combination of agents of the invention may also be that amount or dose that is effective to substantially shrink or destroy a tumor, or permit its surgical removal. An appropriate "effective" amount in any individual case is determined using any suitable technique, (e.g., a dose escalation study) and will depend on the judgment of the practitioner. However, suitable dosage ranges are readily determinable by one skilled in the art.

More than one dose may be required to provide an effective dose. It is understood that an effective dose in one population may or may not be sufficient in all populations. Thus, in connection with the administration of a therapeutic agent, the therapeutic agent is "effective against" a disease or condition when administration in a clinically appropriate manner results in a beneficial effect for at least a statistically significant fraction of subjects, such as a prevention of disease onset, improvement of symptoms, a cure, a reduction in disease signs or symptoms, extension of life, improvement in quality of life, or other effect generally recognized as positive by medical doctors familiar with treating the particular type of disease or condition.

By "enhances" is meant a positive alteration of at least 10%, 25%, 50%, 75%, 100%, or any number therebetween.

As used herein, the term "growth" refers to any tissue or organ that comprises a cellular mass considered to represent an abnormal proliferation. Such growths may be cancerous, non-cancerous, malignant, or non-malignant. If a growth comprises cancer, it may be a tumor. Such tumors may be solid or non-solid.

As used herein, an "immunoassay" is a detection method based on the specific binding of at least one antibody to an antigen, e.g., ELISA, RIA, western blot, and the like.

As used herein "immunogen", "immunogenic", and the like refer to substances that can promote an immune response, e.g., an antibody based or cell mediated immune response, in at least one organism.

By "immunogenic composition" is meant a composition comprising a molecule capable of inducing or modulating an immune response in a subject. Such an immune response may be a prophylactic or therapeutic immune response. In embodiments, the immunogenic composition is a vaccine or T-cell agonist.

As used herein, the term "immunotherapeutic agent" refers to any agent, compound, or biologic which is capable of modulating the host's immune system. For example, an immunotherapeutic agent is capable of causing a stimulation of the immune system against a tumor cell.

As used herein "inducing immunity" is meant to refer to any immune response generated against an antigen. In embodiments, immunity is mediated by antibodies against an infectious agent, which is exhibited by a vertebrate (e.g., a human), that prevents or ameliorates an infection or reduces at least one symptom thereof. The immunogenic compositions of the invention can stimulate the production of antibodies that, for example, neutralize infectious agents, block infectious agents from entering cells, block replication of infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates an infection or reduces at least one symptom thereof. The term "into", as used herein, refers to the successful penetration of a molecule through or within a cell membrane. For example, a viral vector may be introduced into a solid tumor cell under conditions such that the tumor cell is transfected. In another example, a glycolipid may be introduced into a solid tumor cell under conditions such that the glycolipid becomes inserted into the cell's phospholipid bilayer membrane. In yet another example, an antigen—or a vector encoding the antigen—may be introduced into a solid tumor cell under conditions such that the glycolipid becomes inserted into the cell's phospholipid bilayer membrane.

As used herein, the term "intracellular permeation enhancing agent" refers to a compound, molecule, substance, or the like that increases the passage of a therapeutic agent across a cell membrane, e.g., a cell of a solid tumor, and thus, enables the exposure of the contents (e.g., proteins, DNA, cellular machinery) of intracellular environment to the therapeutic agent.

The term "isolated", as used herein, refers to any composition, molecule, or mixture that has undergone a laboratory purification procedure including, but not limited to, extraction, centrifugation, chromatographic separation (i.e., for example, thin layer chromatography or high performance liquid chromatography). Usually such a purification procedure provides an isolated composition, molecule, or mixture based upon physical, chemical, or electrical potential properties. Depending upon the choice of procedure an isolated composition, molecule, or mixture may contain other compositions, compounds or mixtures having similar chemical properties. For example, an isolated composition, molecule, or mixture may contain between 1-20%, 1-10%, or 1-5% of compositions or mixtures having similar chemical properties. In one embodiment, an isolated composition or mixture comprises a mixture of glycolipids free of cholesterol and phospholipids. In one embodiment, an isolated composition or mixture comprises glycolipids having from between 5-15 glycosidic linkages.

As used herein, the term "local" or "locally," as in local administration or coadministration of one or more therapeutics, refers to the delivery of a therapeutic agent to a bodily site that is proximate or nearby the site of a tumor, adjacent or immediately nearby the site of the tumor, at the perimeter of or in contact with the tumor, or within or inside the tumor. Delivery of a therapeutic within the tumor may also be referred to as "intratumoral" administration. Local administration generally excludes systemic administration routes.

The term "nonresectable", as used herein, refers to any part of an organ or bodily structure that cannot be surgically removed. For example, a "nonresectable tumor" may be a tumor physically unreachable by conventional surgical techniques or a tumor where its removal does not improve the overall cancer disease of the patient.

As used herein, "nucleic acid" as in a nucleic acid for delivery to a cell is understood by its usual meaning in the art as a polynucleotide or oligonucleotide which refers to a string of at least two base-sugar-phosphate combinations. Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA, genetic material derived from a virus, and the like. Polynucleotides include nucleic acids of at least two monomers. Anti-sense polynucleotides are nucleic acids that interfere with the function of DNA or RNA. An siRNA or an shRNA is a double stranded RNA that inhibits or disrupts activity or translation, for example by promoting degradation of modifying splicing or processing of the cellular nucleic acid, e.g., mRNA, microRNA, and the like, to which it is targeted. As used herein, siRNA and shRNA include any double stranded RNA molecule that can modulate the stability, translation, or splicing of an RNA to which at least one strand of the double stranded nucleic acid hybridizes. RNAs are well known in the art, see e.g., patent publications WO02/44321, WO/2003/099298, US 20050277610, US 20050244858; and U.S. Pat. Nos. 7,297,786, 7,560,438 and 7,056,704, all of which are incorporated herein by reference. Nucleic acid as used herein is understood to include non-natural nucleotides (not occurring in nature), for example: a derivative of natural nucleotides such as phosphothionates or peptide nucleic acids (such as those described in the patents and applications cited immediately above). A nucleic acid can be delivered to a cell in order to produce a cellular change that is therapeutic. The delivery of a nucleic acid or other genetic material for therapeutic purposes is gene therapy. The nucleic acid may express a protein or polypeptide, e.g., a protein that is missing or non-functional in the cell or subject. The nucleic acid may be single or double stranded, may be sense or anti-sense, and can be delivered to a cell as naked DNA, in combination with agents to promote nucleic acid uptake into a cell (e.g., transfection reagents), in the context of a viral vector, and the like. The nucleic acid can be targeted to a nucleic acid that is endogenous to the cell (mRNA or microRNA), or a heterologous nucleic acid (e.g., nucleic acid from a pathogen, such as a viral gene). Delivery of a nucleic acid means to transfer a nucleic acid from outside a subject to within the outer cell membrane of a cell in the subject.

"Obtaining" is understood herein as manufacturing, purchasing, synthesizing, isolating, purifying, or otherwise coming into possession of.

The term "pharmaceutically acceptable" as used herein, refers to a material, (e.g., a carrier or diluent), which does not abrogate the biological activity or properties of the compounds described herein, and is relatively nontoxic (i.e., the material is administered to an individual without causing undesirable biological effects or interacting in a deleterious manner with any of the components of the composition in which it is contained).

The phrase "pharmaceutically acceptable carrier, excipient, or diluent" is art recognized and includes a pharmaceutically acceptable material, composition or vehicle, suitable for administering compounds of the present invention to mammals. As used herein, the term "pharmaceutically acceptable" means being approved by a regulatory agency of the Federal or a state government or listed in the U.S. Pharmacopia, European Pharmacopia or other generally recognized pharmacopia for use in mammals, e.g., humans.

As used herein, the term "pharmaceutically effective regimen" refers to a systematic plan for the administration of one or more therapeutic agents, which includes aspects such as type of therapeutic agent, therapeutic agent concentrations, intratumoral enhancer concentrations, amounts or levels based on the tumor type, location or size, timing, and repetition, and any changes therein made during the course of the drug administration, which when administered is effective in treating a tumor and/or its metastasis. Such considerations depend on the judgment of the practitioner and are readily determinable by one skilled in the art.

As used herein, the term "proliferative disorder" refers to a disorder wherein the growth of a population of cells exceeds, and is uncoordinated with, that of the surrounding cells. In certain instances, a proliferative disorder leads to the formation of a tumor. In some embodiments, the tumor is benign, pre-malignant, or malignant. In some embodiments, the proliferative disorder is a pancreatic cancer. In some embodiments, the proliferative disorder is a pre-malignant growth on the pancreas.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

By "reduces" is meant a negative alteration of at least 10%, 25%, 50%, 75%, 100%, or any number therebetween.

By "reference" is meant a standard or control condition.

As used herein, the term "regimen" refers to the various parameters that characterize how a drug or agent is administered, including, the dosage level, timing, and iterations, as well as the ratio of different drugs or agents to one another. The term "pharmaceutically effective regimen" refers to a particular regimen which provides a desired therapeutic result or effect, including substantial shrinkage and/or destruction of the tumor or cells that have metastasized therefrom. The term "iterations" refer to the general concept of repeating sets of administering one or more agents. For example, a combination of drug X and drug Y may be given (co-administered at or about at the same time and in any order) to a patient on a first day at dose Z. Drugs X and Y may then be administered (co-administered at or about at the same time and in any order) again at dose Z, or another dose, on a second day. The timing between the first and second days can be 1 day or anywhere up to several days, or a week, or several weeks, or months. The iterative administrations may also occur on the same day, separated by a specified number of minutes (e.g., 10 minutes, 20 minutes, 30 minutes or more) or hours (e.g., 1 hour, 2 hours, 4 hours, 6 hours, 12 hours). An effective dosing regimen may be determinable by those of ordinary skill in the art, e.g., prescribing physician, using standard practices.

A "sample" as used herein refers to a biological material that is isolated from its environment (e.g., blood or tissue from an animal, cells, or conditioned media from tissue culture). In embodiments, the sample is suspected of containing, or known to contain an analyte, such as an infectious agent or a protein of interest (e.g., antibody, cytokine, and the like). A sample can also be a partially purified fraction of a tissue or bodily fluid. A reference sample can be a "normal" sample, from a donor not having the disease or condition fluid, or from a normal tissue in a subject having the disease or condition, or an untreated subject (e.g., a subject not treated with the vaccine). A reference sample can also be taken at a "zero time point" prior to contacting the cell or subject with the agent or therapeutic intervention to be tested.

As used herein, the term "selectively" means tending to occur at a higher frequency in one population than in another population.

As used herein, a "solid tumor" refers to an abnormal mass of tissue that usually does not contain cysts or liquid areas. Solid tumors may be benign (not cancerous), or malignant (cancerous). Generally, a solid tumor connotes cancer of body tissues other than blood, bone marrow, or the lymphatic system.

By "specifically binds" is meant recognition and binding to a target (e.g., polypeptide, cell, and the like), but which does not substantially recognize and bind other molecules in a sample, for example, a biological sample.

The term "subject", as used herein, refers to any organism that is capable of developing a solid tumor. Such organisms include, but are not limited to, human, dog, cat, horse, cow, sheep, goat, mouse, rat, guinea pig, monkey, avian, reptiles etc.

As used herein, the term "substantially shrink or destroy" refers to where the size and/or mass of the tumor has been decreased or altogether eradicated or killed. In the case of tumor shrinkage, the tumor may shrink by at least about 10%, or about 25%, or about 50%, or about 75%, or about 85%, or about 90%, or about by 95%, or by 99%, or more, or any number therebetween. In embodiments, the shrinkage is such that an inoperable tumor is sufficient to permit resection if desired. The concept of substantial shrinkage may also be referred to as "regression," which refers to a diminution of a bodily growth, such as a tumor. Such a diminution may be determined by a reduction in measured parameters such as, but not limited to, diameter, mass (i.e., weight), or volume. This diminution by no means indicates that the size is completely reduced, only that a measured parameter is quantitatively less than a previous determination.

In the case of "substantially destroy" a tumor, this term may refer to either the substantial eradication of actual tumor cells or it may refer to substantially killing the tumor cells but where the cells are not removed or eradicated but remain in the body as dead cells and/or tissue. In the case of substantial eradication, the concept refers to the complete cellular breakdown of a bodily growth, such as, for example, a solid tumor. Such destruction may involve intracellular apoptosis and/or macrophage phagocytosis such that the bodily growth is completely digested and eliminated from the body.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from cancer is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the term "targeting moiety" is a moiety that is capable of enhancing the ability of a therapeutic agent, or other agent of the invention (e.g., an intracellular penetration enhancing agent or immunotherapeutic agent) to be targeted to, to bind with, or to enter, a target cell of the invention (e.g., a cancer tumor cell). In certain embodiments, targeting moieties are polypeptides, carbohydrates or lipids. Optionally, targeting moieties are antibodies, antibody fragments or nanobodies. Exemplary targeting moieties include tumor targeting moieties, such as somatostatin (sst2), bombesin/GRP, luteinizing hormone-releasing hormone (LHRH), neuropeptide Y (NPY/Y1), neurotensin (NT1), vasoactive intestinal polypeptide (VIP/VPAC1) and cholecystokinin (CCK/CCK2). In certain embodiments, a targeting moiety is non-covalently associated with an agent of the invention.

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "To treat a cancer or a tumor" or "Treating a cancer or a tumor" in a mammal means one or more of alleviating a symptom of, correcting an underlying molecular or physiological disorder of, or reducing the frequency or severity of a pathological or deleterious physiological consequence of a cancer or a tumor in a subject. By way of example, and not by limitation, the deleterious physiological consequences of a cancer or a tumor can include uncontrolled proliferation, metastasis and invasion of other tissues, and suppression of an immune response. Thus, treatment of a tumor includes, but is not limited to, inhibiting tumor growth, inhibiting tumor cell proliferation, reducing tumor volume, or inhibiting the spread of tumor cells to other parts of the body (metastasis).

The term "α-gal epitopes", as used herein, refers to any molecule, or part of a molecule, with a terminal structure comprising Galα 1-3Galβ 1-4GlcNAc-R, Gal α 1-3Galβ1-3 GlcNAc-R, or any carbohydrate chain with terminal Galα 1-3 Gal at the non-reducing end.

The term "glycolipids", as used herein, refers to any molecule with at least one carbohydrate chain linked to a ceramide, a fatty acid chain, or any other lipid. Alternatively, a glycolipid maybe referred to as a glycosphingolipid.

The term "α 1,3galactosyltransferase" as used herein, refers to any enzyme capable of synthesizing α-gal epitopes.

The term "anti-Gal binding epitope", as used herein, refers to any molecule or part of molecule that is capable of binding in vivo the natural anti-Gal antibody.

The term "β-ManCer" refers to a β-mannosylceramide containing a sphingosine moiety and a fatty acid moiety having a linear or branched, saturated or unsaturated, aliphatic hydrocarbon group having from about 8 to about 49 carbon atoms, from about 18 to about 49 carbon atoms, from about 8 to about 15 carbon atoms, or from about 18 to about 30 carbon atoms. In embodiments, β-ManCer has the following structure:

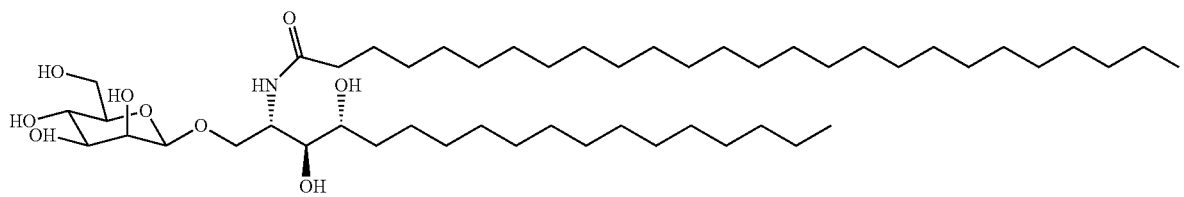 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

The term "sphingosine" as used herein means 2-amino-4-octadecene-1,3-diol, which is an 18-carbon amino alcohol with a hydrocarbon chain that forms a primary portion of ceramide molecules.

The term "ceramide" as used herein, means one of a number of a class of sphingolipids, N-acyl derivatives with long chains of saturated or unsaturated fatty acids. The fatty acid moiety of ceramides can have carbon chain lengths from at least about eight carbons. In embodiments, the fatty acid moiety of β-ManCer can have anywhere from at least about eight carbons in length. For example, it can have a fatty acid moiety of between about 8 carbons to about 49 carbons in length, or for example, it can have a fatty acid moiety of between about 8 carbons to about 15 carbons in length. In other embodiments, the β-ManCer can have a fatty acid moiety of between about 16 carbons and about 30 carbons in length.

As used herein and in the appended claims, the singular forms "a," "and," and "the" include plural reference unless the context clearly dictates otherwise. Thus, for example, reference to "a gene" is a reference to one or more genes and includes equivalents thereof known to those skilled in the art, and so forth.

Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Other definitions appear in context throughout this disclosure.

Any therapeutic agents, compositions, or methods provided herein can be combined with one or more of any of the other therapeutic agents, compositions, and methods provided herein.

BRIEF DESCRIPTION OF THE DRAWINGS

The following detailed description, given by way of example, but not intended to limit the invention solely to the specific embodiments described, may best be understood in conjunction with the accompanying drawings.

FIG. 11A shows progression of tumor growth over time for individual naïve animals. FIG. 11B shows progression of tumor growth over time for individual, complete response, and IT-dosed animals only. FIG. 11C depicts mean tumor growth over time for an age matched control, a complete response animal dosed IT, and a complete response animal IT no outlier.

DETAILED DESCRIPTION OF THE INVENTION

Figure 1:
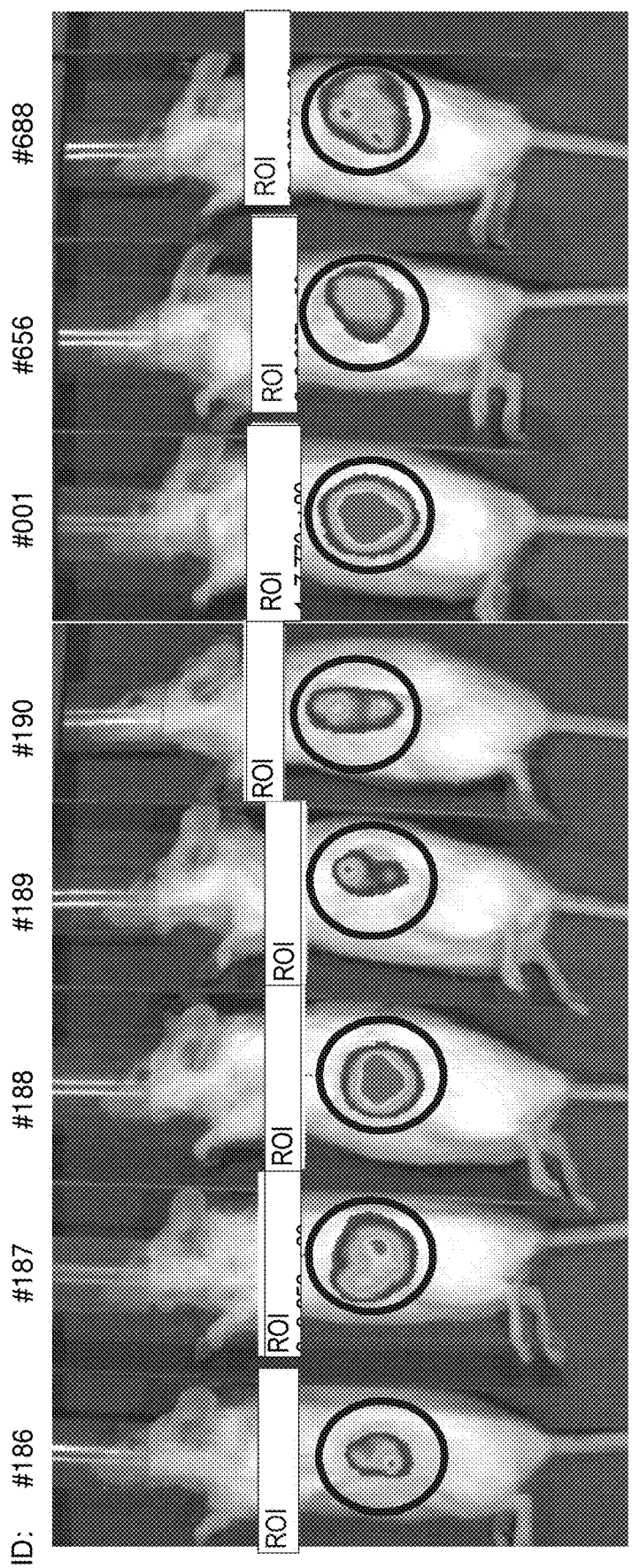
FIG. 1 provides photos of bioluminescent images of s.c.i.d. mice with pancreatic BxPc-3 luciferase treated tumors.

The present invention provides new regional approaches to treating cancer.

The invention is based, at least in part, on the discovery that traditional cancer therapeutic agents are surprisingly more effective when locally or regionally administered in combination with an intracellular penetration enhancing agent. The invention is also based on the discovery that administration of at least one immunotherapeutic agent further enhances the anti-cancer effects of the therapeutic agent and the intracellular penetration enhancing agent (e.g., reduced tumor growth and/or reduced tumor size).

Methods of Treatment

Surgery remains a most effective means of cancer treatment; however, many tumors are inoperable or have metastasized (e.g., only twenty percent of pancreatic cancers are resectable). In addition, despite ablation (i.e., removal of all surrounding healthy tissue), surgery itself often leaves residual tumor cells at the site or causes cells to escape into the systemic system. These free cells often lead to the formation of additional tumors either locally or distally to the original tumor site.

Additional methods for regional treatment of tumors include targeted delivery of chemotherapeutics to a cancerous region, without exposure to the rest of the body. See Collins, J. M., *J. Clin. Oncol.* 2:498-504 (1984); Markman, M., *Semin. Oncolo.* 12:38-42 (1985); and U.S. Patent Publication No. 2007/0196277; U.S. Pat. No. 4,619,913 October 1986; Jia, Y: Int J Nanomedicine. 2012; 7:1697-708, Kim J I: Biomaterials. 2012 June; 33(19):4836-42; Hamstra, D A: J Neurooncol. 2005 July; 73(3):225-38, McArdle Harwood Academic Publishers 2000 ISBN 90-5702-436-5). In this way the normal side effects of chemotherapy, such as nausea, vomiting, hair-loss, and infection can be reduced. Unfortunately, these regional chemotherapeutic approaches have had limited success, if any, in improving outcomes.

As described in detail herein, a novel regional cancer therapeutic and dosing methodology has been discovered that overcomes the limitations associated with current treatment methods. The novel therapeutic methods involve locally or regionally coadministering a therapeutic agent and an intracellular penetration enhancing agent to a subject, thereby achieving high concentrations of the therapeutic agent in the tumor cells. The delivery methods of the present invention minimize exposure of the rest of the body to the cytotoxic therapeutic agent. The novel therapeutic methods also involve administration of an immunotherapy agent. The immunotherapy agent, which is administered before, during, or after delivery of the therapeutic and intracellular penetration enhancing agents, stimulates the immune system and enhances the anti-cancer effects of the therapeutic agent and the intracellular penetration enhancing agent.

In aspects, the invention provides methods for inducing an immune response in a subject. The methods involve administering an effective amount of a therapeutic agent and an intracellular permeation enhancing agent. In embodiments, the subject has a tumor. In embodiments, the therapeutic agent and/or the intracellular permeation enhancing agent is locally or regionally administered to the subject.

In aspects, the invention provides methods for modulating an immune response in a subject. The methods involve administering an effective amount of a therapeutic agent and an intracellular permeation enhancing agent. In embodiments, the subject has a tumor. In embodiments, the therapeutic agent and/or the intracellular permeation enhancing agent is locally or regionally administered to the subject.

In aspects, the invention provides methods treating a tumor in a subject. The methods involve locally or regionally coadministering to the subject a therapeutic agent and an intracellular permeation enhancing agent.

In any of the above aspects or embodiments, the tumor can be a solid tumor. In yet other embodiments, the tumor has metastasized. In embodiments, the tumor is a carcinoma or sarcoma. In related embodiments, the tumor is a carcinoma or sarcoma of the skin, bone, muscle, breast, oral cavity, organ, kidney, liver, lung, gallbladder, pancreas, brain, esophagus, bladder, large intestine, small intestine, spleen, stomach, prostate, testes, ovaries, or uterus. In certain embodiments, the tumor is a carcinoma of the pancreas or colon.

In any of the above aspects or embodiments, the therapeutic agent and/or the intracellular permeation enhancing agent can be administered intratumorally.

In any of the above aspects or embodiments, the method can reduce the growth of the tumor, shrinks the tumor, or eradicates the tumor. In related embodiments, the tumor shrinks by 5%, 10%, 25%, 50%, 75%, 85%, 90%, 95%, or 99% or more as compared to its original size.

In any of the above aspects or embodiments, the methods can involve administering the therapeutic agent and/or the intracellular permeation enhancing agent on a first day and repeating the administration on one or more subsequent days. In related embodiments, the therapeutic agent and the intracellular permeation enhancing agent are coadministered on the first day and administered again on one or more subsequent days. In yet further related embodiments, the first day and one or more subsequent days are separated by between 1 day and about 3 weeks. In related embodiments, the therapeutic agent and the intracellular permeation enhancing agent are coadministered in a ratio of about 1:2, 1:4, 1:10, 1:20, 1:25, 1:50, 1:100, 1:200, or any ratio therebetween (weight ratio of therapeutic agent:intracellular permeation enhancing agent). It is further contemplated within the scope of the invention that the therapeutic agent and/or the intracellular permeation enhancing agent may be administered over the course of one or more cycles.

In any of the above aspects or embodiments, the therapeutic agent and the intracellular permeation enhancing agent can be delivered simultaneously. In any of the above aspects or embodiments, the intracellular permeation enhancing agent can be administered before the therapeutic agent.

In any of the above aspects or embodiments, the therapeutic agent is any anti-cancer therapeutic well known in the art. See, e.g., *Anticancer Drugs: Design, Delivery and Pharmacology (Cancer Etiology, Diagnosis and Treatments)* (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); *Chemotherapy and Biotherapy Guidelines and Recommendations for Practice* (eds. Polovich, M. et al.) (Oncology Nursing Society, 2009); *Physicians' Cancer Chemotherapy Drug Manual* 2012 (eds. Chu, E. & DeVita, Jr., V. T.) (Jones & Bartlett Learning, 2011); *DeVita, Hellman, and Rosenberg's Cancer: Principles and Practice of Oncology* (eds. DeVita, Jr., V. T. et al.) (Lippincott Williams & Wilkins, 2011); and *Clinical Radiation Oncology* (eds. Gunderson, L. L. & Tepper, J. E.) (Saunders) (2011), the contents of which are hereby incorporated by references in their entirety.

In certain embodiments, the therapeutic agent is an anti-cancer agent. The anticancer can be any anticancer agent well known in the art, including, but not limited to, the chemotherapeutic agents described herein.

In yet other embodiments, the therapeutic agent is a therapeutic antibody. The therapeutic antibody can be any therapeutic antibody well known in the art, including, but not limited to, those described herein.

In embodiments, the therapeutic agent is a therapeutic nucleic acid molecule. The therapeutic nucleic acid molecule can be any therapeutic nucleic acid molecule well known in the art.

In embodiments, the therapeutic agent is a radioisotope. The radioisotope can be any radioisotope well known in the art.

In embodiments, the therapeutic agent is a thymidylate synthase inhibitor.

In embodiments, the therapeutic agent is a platinum compound.

In embodiments, the therapeutic agent is a vinca drug.

In other embodiments, the therapeutic agent is a combination of two or more drug compounds.

In any of the above aspects or embodiments, the methods involve administering a therapeutically effective amount of an immunotherapeutic agent. The immunotherapeutic agent may be any suitable means by which to trigger a further immune response that targets destruction of the cells of the tumor. Such targeting by the immune system may also allow the immune system to target tumor cells that have metastasized to other regions of the body.

In embodiments, the immunotherapeutic agent enhances the immunomodulatory effects of the therapeutic agent and/or the intracellular permeation enhancing agent. In related embodiments, the immunotherapeutic agent further reduces the growth of the tumor or further shrinks the tumor.

The immunotherapeutic agent can be administered before, during, or after the therapeutic agent and intracellular penetration enhancing agent have been administered. In embodiments, the immunotherapeutic agent is administered before the first administration of the therapeutic agent and the intracellular permeation enhancing agent. In embodiments, the immunotherapeutic agent is administered simultaneously with the first administration of the therapeutic agent and the intracellular permeation enhancing agent.

In any of the above aspects or embodiments, the therapeutic agent and the immunotherapeutic agent can be administered in a ratio of about 1:2, 1:4, 1:10, 1:25, 1:50, 1:100, 1:200, or any ratio therebetween (weight ratio of therapeutic agent:immunotherapeutic agent).

In any of the above aspects or embodiments, the intracellular permeation enhancing agent and the immunotherapeutic agent can be administered in a ratio of about 1:2, 1:4, 1:10, 1:20, 1:25, 1:50, 1:100, 1:100, or any ratio therebetween (weight ratio of intracellular permeation enhancing agent:immunotherapeutic agent).

In any of the above aspects or embodiments, the immunotherapeutic agent can be administered intraperitoneally; locally or regionally; systemically (e.g. intravenously); or intratumorally.

In any of the above aspects or embodiments, the therapeutic agent and the intracellular permeation enhancing agent can be coupled.

In any of the above aspects or embodiments, the method can involve further administering a standard of care therapy to the subject. In embodiments, the standard of care therapy is surgery, radiation, systemic chemotherapy, or a combination thereof.

In any of the above aspects or embodiments, administration of the therapeutic agent, the intracellular permeation enhancing agent, or the immunotherapeutic agent can be conducted with the aid of an imaging system. For example, an imaging system may be used to calculate the volume of a given tumor so that a tumor volume-based dose of the agents of the invention may be calculated. Additionally, it is contemplated within the scope of the invention that such an imaging system may be used to guide a needle to a specific site of injection within the tumor. The imaging system can be any imaging system well known in the art (see, e.g., The MD Anderson Manual of Medical Oncology (eds. Kantarjian, H. M. et al.) (McGraw-Hill Professional, 2011), the contents of which are hereby incorporated by reference in their entirety), and methods for using an imaging system to aid in the administration of a therapeutic agent, an intracellular permeation enhancing agent, or an immunotherapeutic agent are also well known in the art (see, e.g., Majumder, S. et al., *Expert Rev. Gastroenterol Hepatol.* 6:95-103 (2012); Liu, F. et al., *J. Thorac. Oncol.* 5:879-84 (2010); Schmuecking, M. et al., *Int. J. Radiat. Biol.* 85:814-24 (2009); Zhao, B. et al., *Radiology* 252:263-72 (2009); Thrall, M. M. et al., *Gynecol. Oncol.* 105:17-22 (2007); Bogoni. L. et al., *Br. J. Radiol.* 1:557-62 (2005); Bluemke, D. A. et al., *Radiographics* 17:303-13 (1997); Arimoto, T., *Cancer* 72:2383-8 (1993); Feyerabend, T. et al., *Strahlenther Onkol.* 166:405-10 (1990); and Lee, N., *IEEE Reviews* 2:136-146 (2009), the contents of which are hereby incorporated by reference in their entirety). In embodiments, the imaging system is X-ray computed tomography (CT), fluoroscopy, magnetic resonance imaging (MRI), ultrasound, or positron emission tomography (PET)/computed tomography (CT).

Therapeutic Agents

The present invention contemplates any therapeutic agent suitable for use in the methods described herein (e.g., any type of anti-cancer agent to treat cancer). Suitable therapeutic agents include, but are not limited to, pharmaceutical drugs or compounds (i.e., small molecule drugs), therapeutic antibodies, therapeutic proteins or biologics (e.g., hormone therapies), and nucleic acid molecules (e.g., siRNAs).

In embodiments, the therapeutic agent is an agent that has been shown to have cytotoxic properties against tumor cells. In related embodiments, the therapeutic agent is an existing market-approved pharmaceutical drug or other market-approved composition for treating cancer using a conventional approach.

The "chemotherapeutic agent" includes chemical reagents that inhibit the growth of proliferating cells or tissues wherein the growth of such cells or tissues is undesirable. Chemotherapeutic agents are well known in the art, and any such agent is suitable for use in the present invention. See, e.g., *Anticancer Drugs: Design, Delivery and Pharmacology (Cancer Etiology, Diagnosis and Treatments)* (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); *Chemotherapy and Biotherapy Guidelines and Recommendations for Practice* (eds. Polovich, M. et al.) (Oncology Nursing Society, 2009); *Physicians' Cancer Chemotherapy Drug Manual* 2012 (eds. Chu, E. & DeVita, Jr., V. T.) (Jones & Bartlett Learning, 2011); *DeVita, Hellman, and Rosenberg's Cancer: Principles and Practice of Oncology* (eds. DeVita, Jr., V. T. et al.) (Lippincott Williams & Wilkins, 2011); and *Clinical Radiation Oncology* (eds. Gunderson, L. L. & Tepper, J. E.) (Saunders) (2011), the contents of which are hereby incorporated by references in their entirety.

In one embodiment, the pharmaceutical drug can be an alkylating agent. Alkylating agents directly damage DNA to prevent the cancer cell from reproducing. As a class of drugs, these agents are not phase-specific; in other words, they work in all phases of the cell cycle. Alkylating agents are used to treat many different cancers, including, but not limited to, leukemia, lymphoma, Hodgkin disease, multiple myeloma, sarcoma, as well as cancers of the lung, breast, and ovary. Examples of alkylating agents include, for example, nitrogen mustards (e.g., mechlorethamine, chlorambucil, cyclophosphamide (Cytoxan®), ifosfamide, and melphalan), alkyl sulfonates (e.g., busulfan), triazines (e.g., dacarbazine (DTIC), temozolomide (Temodar®)), Nitrosoureas (including streptozocin, carmustine (BCNU), and lomustine), and ethylenimines (e.g., thiotepa and altretamine). In addition, platinum drugs (e.g., cisplatin, carboplatin, and oxalaplatin) are often considered alkylating agents because they kill cancer cells in a similar way. The invention contemplates all of these drugs, or combinations thereof.

In another embodiment, the invention contemplates any antimetabolite drug. Antimetabolites are a class of drugs that interfere with DNA and RNA growth by substituting for the normal building blocks of RNA and DNA. These agents damage cells during the S phase. They are commonly used to treat leukemias, cancers of the breast, ovary, and the intestinal tract, as well as other types of cancer. Examples of antimetabolites, including, for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine.

The invention also contemplates the use of an anti-tumor antibiotic, such as anthracyclines. Anthracyclines are anti-tumor antibiotics that interfere with enzymes involved in DNA replication. These drugs work in all phases of the cell cycle. They are widely used for a variety of cancers. A major consideration when giving these drugs is that they can permanently damage the heart if given in high doses. For this reason, lifetime dose limits are often placed on these drugs. Examples include Daunorubicin, Doxorubicin (Adriamycin®), Epirubicin, and Idarubicin. Other anti-tumor antibiotics include, for example, Actinomycin-D, Bleomycin, and Mitomycin-C.

Also contemplated are topoisomerase inhibitors. These drugs interfere with enzymes called topoisomerases, which help separate the strands of DNA so they can be copied. They are used to treat certain leukemias, as well as lung, ovarian, gastrointestinal, and other cancers. Examples of topoisomerase I inhibitors include topotecan and irinotecan (CPT-11). Examples of topoisomerase II inhibitors include etoposide (VP-16) and teniposide. Mitoxantrone also inhibits topoisomerase II. Treatment with topoisomerase II inhibitors increases the risk of a second cancer—acute myelogenous leukemia (AML). With this type of drug, a secondary leukemia can be seen as early as 2 to 3 years after the drug is given.

The present invention also contemplates using therapeutic agents known as mitotic inhibitors. Mitotic inhibitors are often plant alkaloids and other compounds derived from natural products. They can stop mitosis or inhibit enzymes from making proteins needed for cell reproduction. These drugs work during the M phase of the cell cycle, but can damage cells in all phases. They are used to treat many different types of cancer including breast, lung, myelomas, lymphomas, and leukemias. These drugs are known for their potential to cause peripheral nerve damage, which can be a dose-limiting side effect. Examples of mitotic inhibitors include Taxanes (e.g., paclitaxel (Taxol®) and docetaxel (Taxotere®)), Epothilones (e.g., ixabepilone (Ixempra®)), Vinca alkaloids (e.g., vinblastine (Velban®), vincristine (Oncovin®), and vinorelbine (Navelbine®)), and Estramustine (Emcyt®).

The anti-cancer agents may also be corticosteroids. Steroids are natural hormones and hormone-like drugs that are useful in treating some types of cancer (lymphoma, leukemias, and multiple myeloma), as well as other illnesses. When these drugs are used to kill cancer cells or slow their growth, they are considered chemotherapy drugs. Corticosteroids are also commonly used as anti-emetics to help prevent nausea and vomiting caused by chemotherapy. They are used before chemotherapy to help prevent severe allergic reactions (hypersensitivity reactions), too. Examples include prednisone, methylprednisolone (e.g., Solumedrol®), and dexamethasone (e.g., Decadron®).

In certain embodiments, the pharmaceutical agent is selected from the group consisting of: Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, and their functionally effective derivatives, pegylated forms, salts, polymorphisms, chiral forms and combinations thereof.

The invention also contemplates any derivative form of the aforementioned pharmaceutical agents and therapeutic agents. Common derivatizations may include, for example, adding a chemical moiety to improve solubility and/or stability, or a targeting moiety, which allows more specific targeting of the molecule to a specific cell or region of the body. The pharmaceutical agents may also be formulated in any suitable combinations, wherein the drugs may either mixed in individual form or coupled together in a manner that retains the functionality of each drug. The drugs may also be derivatized to include a radioisotope or other cell-killing moiety to make the molecule even more effective at killing the cell. In addition, the drugs, or a portion thereof, may be modified with fluorescence compound or other detectable labels which may allow tracking of the drug or agent in the body or within the tumor. The pharmaceutical drug or otherwise any of the aforementioned therapeutic agents may be provided in a precursor form such that they the drug only gains its activity or function after it has been processed in some manner, e.g., metabolized by a cell.

Therapeutic antibodies contemplated by the present invention may include any isotype (IgA, IgG, IgE, IgM, or IgD) of an anti-cancer antibody or immune-active fragment or derivative thereof. Such fragments can include, for example, single-chain variable fragments (scFv), antigen-binding fragment (Fab), crystallizable fragment (Fc) modified to contain an antigen or epitope binding region, and domain antibodies. Derivatized versions of therapeutic antibodies may include, for example, diabodies, nanobodies, and virtually any antibody-derived structure which contains or is engineered to contain an appropriate and effective antigen binding site.

Examples of antibody-based anticancer therapies that may be utilized by the invention can include, for example, Abagovomab, Alacizumab pegol, Alemtuzumab, Altumomab pentetate (Hybri-ceaker), Amatuximab, Anatumomab mafenatox, anti-PD-1 antibodies, Apolizumab, Arcitumomab (CEA-Scan), Belimumab, Bevacizumab, Bivatuzumab mertansine, Blinatumomab, Brentuximab vedotin, Cantuzumab mertansine, Cantuzumab ravtansine, Capromab pendetide (Prostascint), Catumaxomab (Removab), Cetuximab (Erbitux), Citatuzumab bogatox, Cixutumumab, Clivatuzumab tetraxetan (hPAM4-Cide), Conatumumab, Dalotuzumab, Denosumab, Drozitumab, Edrecolomab (Panorex), Enavatuzumab, Gemtuzumab, Ibritumomab tiuxetan, Ipilimumab (MDX-101), Ofatumumab, Panitumumab, Rituximab, Tositumomab, and Trastuzumab.

The invention also contemplates any suitable biologic, e.g., hormone therapy, that can be used to treat cancer. In one non-limiting example, suitable biologics that may be used include hormone therapy. Drugs in this category can be sex hormones, or hormone-like drugs, that change the action or production of female or male hormones. They can be used to slow the growth of breast, prostate, and endometrial (uterine) cancers, which normally grow in response to natural hormones in the body. These cancer treatment hormones do not work in the same ways as standard chemotherapy drugs, but rather by preventing the cancer cell from using a hormone it requires for grow, or by preventing the body from making the hormones required for growth of the cancer. Such hormone therapies can include, for example, anti-estrogens (e.g., fulvestrant (Faslodex®), tamoxifen, and toremifene (Fareston®)), Aromatase inhibitors (e.g., anastrozole (Arimidex®), exemestane (Aromasin®), and letrozole (Femara®)), Progestins (e.g., megestrol acetate (Megace®)), Estrogens, Anti-androgens (e.g., bicalutamide (Casodex®), flutamide (Eulexin®), and nilutamde (Nilandron®)), and Gonadotropin-releasing hormone (GnRH) (aka luteinizing hormone-releasing hormone (LHRH) agonists or analogs, e.g., leuprolide (Lupron®) and goserelin (Zoladex®)).

The invention also contemplates that cancer treatment may be effectuated using a nucleic acid molecule that targets a specified "target gene" that has a role in cancer. The effect of the nucleic acid molecule on the target gene may include gene silencing, mRNA destruction, or inhibited transcription, or the like, such that the level of expression and/or conversion of the target gene to an operable encoded polypeptide are substantially affected (up or down) such that the cancer is inhibited and/or destroyed by the agent. The term "target gene" refers to nucleic acid sequences (e.g., genomic DNAs or mRNAs) encoding a target protein, peptide, or polypeptide, or that encode for or are regulatory nucleic acids (e.g., a "target gene" for purpose of the instant invention can also be a miRNA or miRNA-encoding gene sequence) which have a role in cancer. In certain embodiments, the term "target gene" is also meant to include isoforms, mutants, polymorphisms, and splice variants of target genes.

Any nucleic acid based agent well known in the art is suitable for use in the invention. Exemplary types of nucleic acid based agents include, but are not limited to, single stranded ribonucleic acid agents (e.g., microRNAs), anti-sense-type oligonucleotide agents, double-stranded ribonucleic acid agents, and the like.

Methods for constructing therapeutic nucleic acids are well known in the art. For example, interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof and the sense strand comprises nucleotide sequence corresponding to the target nucleic acid sequence or a portion thereof.

Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

Methods for administering/delivering therapeutic nucleic acids are well known in the art. For example, therapeutic nucleic acid molecules may be delivered in a delivery vehicle, such as a lipid vesicle or other polymer carrier material known in the art. Non-limiting examples of additional lipid-based carrier systems (which may be prepared with at least one modified cationic lipid of the invention) suitable for use in the present invention include lipoplexes (see, e.g., U.S. Patent Publication No. 20030203865; and Zhang et al., *J. Control Release,* 100: 165-180 (2004)), pH-sensitive lipoplexes (see, e.g., U.S. Patent Publication No. 2002/0192275), reversibly masked lipoplexes (see, e.g., U.S. Patent Publication Nos. 2003/0180950), cationic lipid-based compositions (see, e.g., U.S. Pat. No. 6,756,054; and U.S. Patent Publication No. 2005/0234232), cationic liposomes (see, e.g., U.S. Patent Publication Nos. 2003/0229040, 2002/0160038, and 2002/0012998; U.S. Pat. No. 5,908,635; and PCT Publication No. WO 01/72283), anionic liposomes (see, e.g., U.S. Patent Publication No. 2003/0026831), pH-sensitive liposomes (see, e.g., U.S. Patent Publication No. 2002/0192274; and AU 2003/210303), antibody-coated liposomes (see, e.g., U.S. Patent Publication No. 2003/0108597; and PCT Publication No. WO 00/50008), cell-type specific liposomes (see, e.g., U.S. Patent Publication No. 2003/0198664), liposomes containing nucleic acid and peptides (see, e.g., U.S. Pat. No. 6,207, 456), liposomes containing lipids derivatized with releasable hydrophilic polymers (see, e.g., U.S. Patent Publication No. 2003/0031704), lipid-entrapped nucleic acid (see, e.g., PCT Publication Nos. WO 03/057190 and WO 03/059322), lipid-encapsulated nucleic acid (see, e.g., U.S. Patent Publication No. 2003/0129221; and U.S. Pat. No. 5,756,122), other liposomal compositions (see, e.g., U.S. Patent Publication Nos. 2003/0035829 and 2003/0072794; and U.S. Pat. No. 6,200,599), stabilized mixtures of liposomes and emulsions (see, e.g., EP1304160), emulsion compositions (see, e.g., U.S. Pat. No. 6,747,014), and nucleic acid micro-emulsions (see, e.g., U.S. Patent Publication No. 2005/0037086).

If suitable, any of the agents of the invention, including pharmaceutical drugs, biologics, and therapeutic antibodies, may also be delivered via the above described carrier systems. All carrier systems may further be modified with a targeting moiety or the like in order to facilitate delivery of the composition to a target tumor of interest.

In an embodiment, the present invention utilizes platinum compounds as the therapeutic agent. Platinum containing compound have been used for several years as an effective treatment of several types of cancers. Platinum based compounds (e.g., carboplatin, cisplatin, oxaliplatin) are anti-neoplastic agents administered by physicians intravenously (IV) to treat various cancers. Intravenous administration is generally used because the oral bioavailability of carboplatin alone is low (approximately 4%) and highly variable. Platinum based products potently kill fast dividing cells. However, administration of carboplatin by intravenous infusion results in drug throughout the body, killing healthy fast dividing cells including and especially bone marrow cells. Intravenous administration of carboplatin results in a dilute blood concentration of the drug reaching the tumor site. In addition, because of the dilute drug concentration there is poor penetration into the tumor cells.

Upon entering the cancer cells these compounds damage the DNA and cause cross links in the strands, thereby preventing future DNA production, which ultimately results in cancer cell death. This effect is apparently cell-cycle nonspecific. When given intravenously, platinum can cause severe blood disorders (e.g., anemia bone marrow suppression) resulting in infection or bleeding problems. The major route of elimination of the two main platinum compounds is renal excretion. Cisplatin and carboplatin are generic, platinum-based chemotherapeutic agents and widely available. The chemical name for carboplatin is platinum, diammine [1,1-cyclobutane-dicarboxylato (2-)-0,0']-(SP-4-2). Carboplatin is a crystalline powder with the molecular formula of $C_6H_{12}N_2O_4Pt$ and a molecular weight of 371.25. It is soluble in water at a rate of approximately 14 mg/mL, and the pH of a 1% solution is 5-7, whereas Cisplatin is soluble at approximately 1-2 mg/ML. These compounds are virtually insoluble in ethanol, acetone, and dimethylacetamide. They are currently administered only by intravenous infusion.

In another embodiment, the present invention employs thymidalate synthesis inhibitors. These agents include the agent 5-FU (fluorouracil), which has been in use against cancer for about 40 years. The compound acts in several ways, but principally as a thymidylate synthase inhibitor, interrupting the action of an enzyme which is a critical factor in the synthesis of the pyrimidine thymine-which is important in DNA replication. 5-FU is not orally absorbed. Currently the best treatment therapy for pancreatic cancer is a course of therapy using Gemcitabine (Gemzar).

As a pyrimidine analogue, these compounds are transformed inside the cell into different cytotoxic metabolites which are then incorporated into DNA and RNA, finally inducing cell cycle arrest and apoptosis by inhibiting the cell's ability to synthesize DNA. These compounds are typically S-phase specific drug and only active during certain cell cycles. In addition to being incorporated in DNA and RNA, these drugs have been shown to inhibit the activity of the exosome complex, an exoribonuclease complex of which the activity is essential for cell survival.

Intracellular Penetration Enhancing Agents

The present invention is based, in part, on penetration agents, such as benzoate linked aliphatic acids, functionalized keto acids (e.g. oxo-6-phenylhexanoic acid), keto esters, modified acylated amino acids (e.g., sodium N-[8-2-(2-hyrodxybenzoyl)amino caprylate), to substantially enhance drug permeability or penetration into cancer cells to surprisingly increase and unexpectedly improve cancer cell killing. Thus, in one aspect, the present invention provides a method for treating cancer by locally or regionally coadministering a combination of a therapeutic agent, such as those described above, together with an intracellular penetration enhancing agent in amounts and in a manner that results in substantial tumor shrinkage and/or destruction.

The invention contemplates any suitable intracellular penetration enhancing agent, known or yet to be discovered or developed.

A number of drug delivery companies have developed such compounds to increase cell penetration for purposes of delivery charged or macromolecule compounds to the blood stream by non injection methods. Such companies include Emisphere Technologies, Acrux Pharma Pty, Ltd., Oramed Pharmaceuticals, Apollo Life Sciences, Diabetology, and Unigene. Generally, these platforms were developed to achieve systemic delivery of therapeutics via conventional routes, such as, oral, buccal, pulmonary or dermal; however, none contemplated the present usage of such penetration enhancing agents in the manner described in conjunction with the present invention.

It will be appreciated that conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers. In the delivery to animals of biologically active or chemically active pharmacological and therapeutic agents, physical and chemical barriers are imposed by the body. Examples of physical barriers are the skin and various organ membranes that are traversed before reaching a target, and examples of chemical barriers include, but are not limited to, variations in pH, lipid bilayers, and degrading enzymes. The cellular membrane also represents an important barrier having a significant effect on the effectiveness of drug delivery.

The present invention is based on combining the delivery of an anticancer therapeutic with an intracellular penetration enhancing agent administered locally using advanced imaging techniques to set the dose and guide the administration prior to or at or about the same time as the therapeutic agent to substantially enhance cellular membrane penetration of the locally-delivered anti-cancer agents.

Accordingly, in one aspect of the invention, the method described herein involves a "penetration enhancer" or carrier that imparts improved cell transport. These molecules facilitate or enable the penetration and/or transport of therapeutic molecules across biological membranes into cells. This specific use for such penetration compounds, such as those described in Emisphere Technologies' U.S. Pat. No. 5,650, 386 (which is incorporated by reference in its entirety), has not previously been contemplated. In other words, the combination of permeation enhancers capable of facilitating intracellular transport of locally delivered anticancer agents was not previously considered or contemplated in the art.

In one embodiment, the present invention comprises 6-oxo-6-phenyl hexanoic acid as the intracellular penetration enhancing compound or a salt or analog thereof,

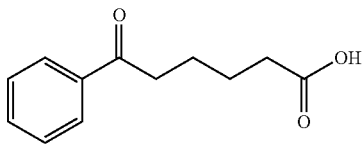 [SMILES: O=C(O)CCCCC(=O)c1ccccc1]

in a method for treating cancer, e.g., a solid tumor, comprising locally coadministering the above compound and an anticancer therapeutic agent in therapeutically effective amounts and in accordance with a regimen that is effective to cause substantial shrinkage of the tumor and/or destruction of the tumor.

In other embodiments, the intracellular penetration enhancing agent is modified amino acids, N-[8-(2-hydroxybenzoyl)aminooctanoic acid,

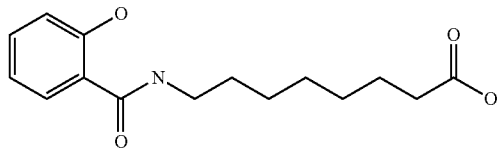 [SMILES: O=C(O)CCCCCCCNC(=O)c1ccccc1O]

N-[8-(2-hydroxybenzoyl)aminodecanoic acid, N-(5-chlorosalicyloyl)-8-aminocaprylic acid, N-[4-(4-chloro-2hydroxybenzoyl)amino1 butanoic acid, 8-(N-2-hydroxy-4-methoxybenzoyl)-aminocaprylic acid (4-MOAC), 8-Oxo-8-phenyloctanoic acid, 8-(2,5-Dichlorophenyl)-8-oxooctanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, 8-[(3-methylcyclohexyl)oxy]octanoic acid, 7-[(3-methylcyclohexyl)oxy]heptanoic acid, 6-[(3-methylcyclohexyl)oxy]hexanoic acid, 5-[(3-methylcyclohexyl)oxy]pentanoic acid, 4-[(3-methylcyclohexyl)oxy]butanoic acid, 3-[(3-methylcyclohexyl)oxy]propanoic acid and other pharmaceutically acceptable salts thereof, as well as octyl salicylate or, octisalate, Diketopiperazines, saponin, Acylcarnitines, Alkanoylcholines, taurodihydrofusidate, sulphoxides, Oxazolidinones, pyrrolidones, alcohols and alkanols, benzoic acid, glycols, surfactants, terpenes or their functionally effective salts, derivatives or combinations thereof.

In yet further embodiments, the intracellular penetration enhancing compound is selected from any one of the compounds described in U.S. Pat. Nos. 4,764,381; 4,783,450; 4,885,174; 4,983,396; 5,045,553; 5,118,845; 5,219,877; 5,401,516; 5,451,410; 5,540,939; 5,443,841; 5,541,155; 5,578,323; 5,601,839; 5,601,846; 5,627,270; 5,629,020; 5,643,957; 5,650,386; 5,693,338; 5,693,769; 5,709,861; 5,714,167; 5,773,647; 5,766,633; 5,776,888; 5,792,451; 5,804,688; 5,863,944; 5,866,536; 5,876,710; 5,879,681; 5,820,881; 5,834,010; 5,840,340; 5,935,601; 5,939,381; 5,955,503; 5,990,166; 5,958,457; 5,965,121; 5,972,387; 5,976,569; 5,989,539; 6,001,347; 6,051,258; 6,051,561; 6,060,513; 6,071,510; 6,090,958; 6,099,856; 6,100,298; 6,180,140; 6,221,367; 6,242,495; 6,245,359; 6,313,088; 6,331,318; 6,333,046; 6,344,213; 6,358,504; 6,395,774; 6,413,550; 6,428,780; 6,461,643; 6,525,020; 6,610,329; 6,623,731; 6,627,228; 6,642,411; 6,646,162; 6,663,887; 6,663,898; 6,693,208; 6,699,467; 6,673,574; 6,818,226; 6,846,844; 6,906,030; 6,916,489; 6,916,789; 6,960,355; 6,972,300; 6,991,798; 7,005,141; 7,067,119; 7,071,214; 7,084,279; 7,115,663; 7,125,910; 7,129,274; 7,138,546; 7,151,191; 7,186,414; 7,208,483; 7,217,703; 7,268,214; 7,276,534; 7,279,597; 7,297,794; 7,351,741; 7,384,982; 7,387,789; 7,390,834; 7,485,321; 7,491,796; 7,495,030; 7,553,872; 7,638,599; 7,670,626; 7,700,775; 7,727,558; 7,744,910; 7,820,722; 7,893,297; 7,951,971; 7,977,506; 8,003,697; 8,017,727; 8,026,392; 8,088,734; and RE35,862, each of which is hereby incorporated by reference.

Intracellular penetration enhancers in general have little to no known pharmacological activity themselves. These technologies, such as those described and shown above, make it possible to penetrate membranes to deliver a therapeutic agent without altering its chemical form or biological integrity. Such penetration enhancers have demonstrated significantly increased absorption of several different types of agents.

Immunotherapeutic Agents

In another aspect, the invention employs one or more immunotherapeutic agents to further enhance the tumor cell inhibitory and/or destructive effects imparted by the combination of the anticancer therapeutic agent with the intracellular penetration enhancing agent. For example, the immunotherapeutic agent is delivered after the effects of the first two agents have set in, but the invention is not limited to this concept. The invention contemplates any administration regimen involving all three agents so long as the therapeutic benefits attributable to the each of the agents may occur. It is also contemplated within the scope of the invention that administration of the one or more immunotherapeutic agents have immunostimulatory activity that provides prophylaxis against further recurrence of a cancer. This immunostimulatory effect can be achieved when the agent is given intratumorally or intraperitoneally either with or without an intracellular penetration enhancer.

Those skilled in the art will appreciate that an immunotherapeutic agent is a treatment that aims to use an individual's own immune system to fight cancer or disease. This may be accomplished by boosting the individual's own immune system or to provide supplemental pieces of an otherwise defective or deficient immune system.

Immunotherapy is a form of biological therapy which can be used in the present invention supplement and/or enhance the effects of treating with the therapeutic agent/penetration enhancing treatment. There are generally two recognized forms of immunotherapy, which are referred to as active immunotherapies and passive immunotherapies. Active immunotherapies stimulate the body's own immune system to fight a disease. Passive immunotherapies use immune system components, such as antibodies, prepared outside the body, to enhance the body's immune response level. Immunotherapies may also work by targeting certain types of cells or antigens (specific immunotherapies) or they may work by more generally stimulating the immune system (non-specific immunotherapies, or sometimes referred to as adjuvants). Some examples of immunotherapies contemplated by the invention include monoclonal antibody therapy (such as rituximab and alemtuzumab), non-specific immunotherapies and adjuvants (substances which boost the immune response such as interleukin-2 and interferon-alpha), immunomodulating drugs (such as thalidomide and lenalidomide), and cancer vaccines (e.g., NKT cell agonists, including but not limited to α-GalCer, βMannCer, or α-Gal glycolipids).

Accordingly, immunotherapeutic agents, which may also be referred to in same meaning as "immunomodulator" can include, for example, interleukins (e.g., IL-2, IL-7, or IL-12), certain other cytokines (e.g., interferons, growth colony stimulating factor (G-CSF), imiquimod), chemokines, and other types of agents, which can include antigens, epitopes, antibodies, monoclonal antibodies, or even a delivery vehicle to deliver one or more of these compounds, and may even also include recombinant immune system cells. Such immunotherapeutic agents can include recombinant forms, synthetic forms, and natural preparations (see D'Alessandro, N. et al., *Cancer Therapy: Differentiation, Immunomodulation and Angiogenesis*, New York: Springer-Verlag, 1993).

In certain embodiments, the immunotherapeutic agent of the invention is a cancer vaccine that may include, for example, Ovalabumin, Neuvenge®, Oncophage, CimaVax-EGF, Mobilan, α-Gal glycolipids, adenovirus delivered vaccines, Celldex's CDX1307 and CDX1401; GRNVAC1, viral based vaccines, MVA-BN, PRO STVAC®, Advaxis'; ADXS11-001, ADXS31-001, ADXS31-164, BiovaxID, folate binding protein (E39), Granulocyte macrophage colony stimulating factor (GM-CSF) with and without E75 (NeuVax) or OncoVEX, trastuzumab, Ae-37, IMA901, SC1B1, Stimuvax, peptides that can elicit cytotoxic lymphocyte response, peptide vaccines including telomerase peptide vaccine (GV1001), survivin peptide, MUC1 peptide, ras peptide, TARP29-37-9V Peptide epitope enhanced peptide, DNA Vector pPRA-PSM with synthetic peptides E-PRA and E-PSM; Ad.p53 DC vaccine, NY-ESO-1 Plasmid DNA (pPJV7611), genetically modified allogeneic (human) tumor cells for the expression of IL-1, IL-7, GM-CSF, CD80 or CD154, HyperAcute®-Pancreatic cancer vaccine (HAPa-1 and HAPa-2 components), Melaxin (autologous dendritoma vaccine) and BCG, GVAX (CG8123), CD40 ligand and IL-2 gene modified autologous skin fibroblasts and tumor cells, ALVAC-hB7.1, Vaximm Gmbh's VXM01, Immunovative Therapies' AlloStim-7, ProstAtak™ TG4023 (MVA-FCU1), Antigenic's HSPPC-96, Immunovaccine Technologies' DPX-0907 which consists of specific HLA-A2-restricted peptides, a universal T Helper peptide, a polynucleotide adjuvant, a liposome and Montanide (ISA51 VG), GSK2302032A, Memgen's ISF35, Avax's OVax: Autologous, DNP-Modified Ovarian vaccine, Theratope®, Ad100-gp96Ig-HLA A1, Bioven's recombinant Human rEGF-P64K/Montanide vaccine, TARP 29-37, or Dendreon's DN24-02.

In another embodiment, the immunotherapeutic agent takes advantage of the body's innate immune system and has the effect when introduced of triggering the innate immune response against the unwanted cancer or tumor. In one embodiment in particular, the present invention utilizes an immunotherapeutic agent that effectively converts the target tumor into a vaccine in situ (e.g., utilization of a NKT cell anti-tumor agent).

For example, this embodiment can involve generating autologous tumor-associated antigens (TAA) in treated patients. α-Gal glycolipids carry the carbohydrate α-gal epitope (Galα1-3β1-4GlcNac-R) which binds the most abundant naturally-occurring antibody in humans—the anti-Gal antibody. The anti-Gal antibody is present in high concentrations due to the continuous exposure to the α-Gal epitope due to its presence in bacteria. Human tissue does not contain natural α-Gal epitopes as that would cause an attack by the immune system on that tissue. Thus tumors are not vulnerable to attack by naturally occurring anti-α-Gal antibodies. The underlying inventive aspect is that α-Gal glycolipids injected as micelles insert into tumor cell membranes resulting in α-Gal epitope expression on tumor cells and thus the binding of the natural anti-Gal antibody. In this manner, the tumor itself becomes a vaccine in situ. The Ag-epitope/Gal Ab interaction activates complement and generates complement cleavage chemotactic factors that recruit antigen presenting cells (APC). The APC transport internalized TAA to regional lymph nodes, process and present the multiple TAA peptides for activation of tumor specific T cells. The T cells proliferate, leave the lymph nodes and circulate to seek and destroy the tumor and any micrometastases presenting the autologous TAA.

The technology has been demonstrated to be highly effective in vivo. Intratumoral injection of α-gal epitopes linked to lipids in a knock-out mouse model (i.e. α-gal epitope absent mice) with developed adenocarcinoma tumors of significant size have demonstrated regression of the tumors and prevention of distal metastasis. In addition, a dose ranging, human clinical study (ND filed) that administered GMP produced α-Gal lipids to 11 patients with late state adenocarcinomas demonstrated the safety of the system and an increased life expectancy for a number of patients including those with pancreatic adenocarcinoma. Additional descriptive support of this immunotherapeutic agent can be found in U.S. Pat. No. 7,820,628, which is incorporated by reference in its entirety.

In another embodiment, the invention involves use of β-mannosylceramide (β-ManCer) to treat patients. β-ManCer is an NKT agonist that promotes immunity against tumors and infectious agents through nitric oxide and TNFα dependent mechanisms. β-ManCer can also be used with α-GalCer to synergistically enhance the effects of α-GalCer. The β-ManCer can contain a sphingosine moiety and a fatty acid moiety having a linear or branched, saturated or unsaturated, aliphatic hydrocarbon group having from about 8 to about 49 carbon atoms, from about 18 to about 49 carbon atoms, from about 8 to about 15 carbon atoms, or from about 18 to about 30 carbon atoms. In related embodiments, β-ManCer has the following structure:

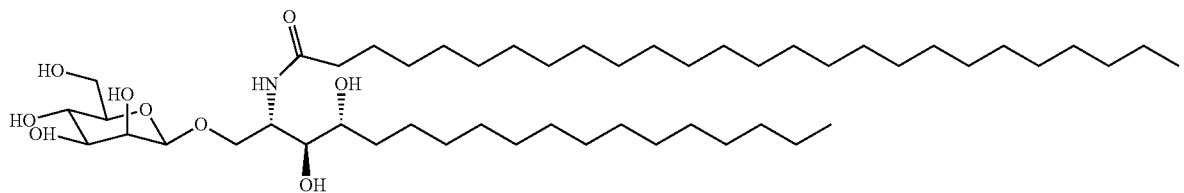 [SMILES: CCCCCCCCCCCCCCCCCCCCCCCCCC(=O)N[C@@H](COC1OC(CO)C(O)C(O)C1O)[C@H](O)[C@H](O)CCCCCCCCCCCCCC]

Additional descriptive support of this immunotherapeutic agent can be found in International Patent Application No. PCT/US2011/028024, which is incorporated by reference in its entirety.

Accordingly, in one aspect, the present invention comprises locally co-administering an anticancer therapeutic agent and an intracellular penetration enhancing agent in therapeutically effective amounts and in accordance with a regimen that results in substantial shrinkage and/or destruction of a target tumor. The method of the invention further comprises enhancing the effects of the therapeutic agent and the intracellular penetration enhancing agent by administering an immunotherapeutic agent. The treatment results in substantial shrinkage and/or destruction of tumor cells, any micrometastases or metastasized cells that have relocated to other parts of the body. In an embodiment, the immunotherapeutic agent is a cancer vaccine that causes the tumor to function as an in situ vaccine, e.g., introduction of the α-gal epitopes into the tumor.

Introduction of the immunotherapeutic agents of the invention, e.g., a cancer vaccine (e.g., T-cell agonists), may be achieved using any suitable approach, including by local or regional administration of the agent at, near, or within the tumor or micrometastases. The agent may also be delivered, where suitable, via gene therapy. For example, in the case of a cancer vaccine that involves introducing a particular antibody-inducing antigen in a tumor, the antibody-inducing antigen may be introduced by injecting or otherwise directly administering a genetic vector or otherwise nucleic acid molecule capable of expressing the desired antigen in the tumor. The antigens themselves may also be directly administered into the target tissue.

Target Cancers

The present invention contemplates treating a broad range of diseases, including tumors of all types, locations, sizes, and characteristics. For example, the method of the invention is suitable for treating, for example, pancreatic cancer and colon cancer.

In other embodiments, virtually any type of cancer may be treatable by the present invention, including the following cancers:

Acute myeloid leukemia
Adrenocortical carcinoma
AIDS-related cancers
AIDS-related lymphoma
Anal cancer
Appendix cancer
Astrocytoma, childhood cerebellar or cerebra
Basal cell carcinoma
Bile duct cancer, extrahepatic
Bladder cancer
Bone cancer, Osteosarcoma/Malignant fibrous histiocytoma
Brainstem glioma
Brain tumor
Brain tumor, cerebellar astrocytoma
Brain tumor, cerebral astrocytoma/malignant glioma
Brain tumor, ependymoma
Brain tumor, medulloblastoma
Brain tumor, supratentorial primitive neuroectodermal tumors
Brain tumor, visual pathway and hypothalamic glioma
Breast cancer
Bronchial adenomas/carcinoids
Burkitt lymphoma
Carcinoid tumor, childhood
Carcinoid tumor, gastrointestinal
Carcinoma of unknown primary
Central nervous system lymphoma, primary
Cerebellar astrocytoma, childhood
Cerebral astrocytoma/Malignantglioma, childhood
Cervical cancer
Childhood cancers
Chronic lymphocytic leukemia
Chronic myelogenous leukemia
Chronic myeloproliferative disorders
Colon Cancer
Cutaneous T-cell lymphoma
Desmoplastic small round cell tumor
Endometrial cancer
Ependymoma
Esophageal cancer
Ewing's sarcoma in the Ewing family of tumors
Extracranial germ cell tumor, Childhood
Extragonadal Germ cell tumor
Extrahepatic bile duct cancer
Eye Cancer, Intraocular melanoma
Eye Cancer, Retinoblastoma
Gallbladder cancer
Gastric (Stomach) cancer
Gastrointestinal Carcinoid Tumor
Gastrointestinal stromal tumor (GIST)
Germ cell tumor: extracranial, extragonadal, or ovarian
Gestational trophoblastic tumor
Glioma of the brain stem
Glioma, Childhood Cerebral Astrocytoma
Glioma, Childhood Visual Pathway and Hypothalamic
Gastric carcinoid
Hairy cell leukemia
Head and neck cancer
Heart cancer
Hepatocellular (liver) cancer
Hodgkin lymphoma
Hypopharyngeal cancer
Hypothalamic and visual pathway glioma, childhood
Intraocular Melanoma
Islet Cell Carcinoma (Endocrine Pancreas)
Kaposi sarcoma
Kidney cancer (renal cell cancer)
Laryngeal Cancer
Leukemias Leukemia, acute lymphoblastic (also called acute lymphocytic leukemia)
Leukemia, acute myeloid (also called acute myelogenous leukemia)
Leukemia, chronic lymphocytic (also called chronic lymphocytic leukemia)
Leukemia, chronic myelogenous (also called chronic myeloid leukemia)
Leukemia, hairy cell
Lip and Oral Cavity Cancer
Liposarcoma
Liver Cancer (Primary)
Lung Cancer, Non-Small Cell
Lung Cancer, Small Cell
Lymphomas
Lymphoma, AIDS-related
Lymphoma, Burkitt
Lymphoma, cutaneous T-Cell
Lymphoma, Hodgkin
Lymphomas, Non-Hodgkin (an old classification of all lymphomas except Hodgkin's)
Lymphoma, Primary Central Nervous System
Macroglobulinemia, Waldenstrom
MalignantFibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Mouth Cancer
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple (Cancer of the Bone-Marrow)
Myeloproliferative Disorders, Chronic
Nasal cavity and paranasal sinus cancer
Nasopharyngeal carcinoma
Neuroblastoma
Non-Hodgkin lymphoma
Non-small cell lung cancer
Oral Cancer
Oropharyngeal cancer
Osteosarcoma/malignant fibrous histiocytoma of bone
Ovarian cancer
Ovarian epithelial cancer (Surface epithelial-stromal tumor)
Ovarian germ cell tumor
Ovarian low malignant potential tumor
Pancreatic cancer
Pancreatic cancer, islet cell
Paranasal sinus and nasal cavity cancer
Parathyroid cancer
Penile cancer
Pharyngeal cancer
Pheochromocytoma
Pineal astrocytoma
Pineal germinoma
Pineoblastoma and supratentorial primitive neuroectodermal tumors, childhood
Pituitary adenoma
Plasma cell neoplasia/Multiple myeloma
Pleuropulmonary blastoma
Primary central nervous system lymphoma
Prostate cancer
Rectal cancer
Renal cell carcinoma (kidney cancer)
Renal pelvis and ureter, transitional cell cancer
Retinoblastoma
Rhabdomyosarcoma, childhood
Salivary gland cancer
Sarcoma, Ewing family of tumors
Sarcoma, Kaposi
Sarcoma, soft tissue
Sarcoma, uterine
Sézary syndrome
Skin cancer (nonmelanoma)
Skin cancer (melanoma)
Skin carcinoma, Merkel cell
Small cell lung cancer
Small intestine cancer
Soft tissue sarcoma
Squamous cell carcinoma—see Skin cancer (nonmelanoma)
Squamous neck cancer with occult primary, metastatic
Stomach cancer
Supratentorial primitive neuroectodermal tumor, childhood
T-Cell lymphoma, cutaneous—see Mycosis Fungoides and Sezary syndrome
Testicular cancer
Throat cancer
Thymoma, childhood
Thymoma and Thymic carcinoma
Thyroid cancer
Thyroid cancer, childhood
Transitional cell cancer of the renal pelvis and ureter
Trophoblastic tumor, gestational
Unknown primary site, carcinoma of, adult
Unknown primary site, cancer of, childhood
Ureter and renal pelvis, transitional cell cancer
Urethral cancer
Uterine cancer, endometrial
Uterine sarcoma
Vaginal cancer
Visual pathway and hypothalamic glioma, childhood
Vulvar cancer
Waldenstrom macroglobulinemi
Wilms tumor (kidney cancer), childhood Those of ordinary skill in the art will appreciate how cancers are classified. Typically, cancers are classified by the type of cell that the tumor cell resembles and is therefore presumed to be the origin of the tumor. These types include:

Carcinoma: Cancers derived from epithelial cells. This group includes many of the most common cancers, particularly in the aged, and include nearly all those developing in the breast, prostate, lung, pancreas, and colon.

Sarcoma: Cancers arising from connective tissue (i.e. bone, cartilage, fat, nerve), each of which develop from cells originating in mesenchymal cells outside the bone marrow.

Lymphoma and leukemia: These two classes of cancer arise from hematopoietic (blood-forming) cells that leave the marrow and tend to mature in the lymph nodes and blood, respectively.

Germ cell tumor: Cancers derived from pluripotent cells, most often presenting in the testicle or the ovary (seminoma and dysgerminoma, respectively).

Blastoma: Cancers derived from immature "precursor" cells or embryonic tissue. These are also most common in children.

Moreover, it will be appreciated that cancers are usually named using -carcinoma, -sarcoma or -blastoma as a suffix, with the Latin or Greek word for the organ or tissue of origin as the root. For example, cancers of the liver parenchyma arising from malignant epithelial cells is called hepatocarcinoma, while a malignancy arising from primitive liver precursor cells is called a hepatoblastoma, and a cancer arising from fat cells is called a liposarcoma. For some common cancers, the English organ name is used. For example, the most common type of breast cancer is called ductal carcinoma of the breast. Here, the adjective ductal refers to the appearance of the cancer under the microscope, which suggests that it has originated in the milk ducts.

Benign tumors (which are not cancers) are named using -oma as a suffix with the organ name as the root. For example, a benign tumor of smooth muscle cells is called a leiomyoma (the common name of this frequently occurring benign tumor in the uterus is fibroid). Confusingly, some types of cancer also use the -oma suffix, examples including melanoma and seminoma.

Some types of cancer are named for the size and shape of the cells under a microscope, such as giant cell carcinoma, spindle cell carcinoma, and small cell carcinoma.

The present invention generally can treat all forms of the above cancers. For example, the method of the invention advantageously may treat solid tumors arising in any tissue of the body including, but not limited to, the skin, bone, muscle, breast, organ, kidney, liver, lung, gallbladder, pancreas, brain, esophagus, bladder, large intestine, small intestine, spleen, stomach, prostate, testes, ovaries, or uterus.

The present invention generally also may treat all forms of the above cancers and where the cancer is at any stage. The skilled person will appreciate that cancer severity is staged (I to IV) with survival prognosis in stage III and IV often being low for several cancer types.

The present invention also may be effective against tumors that arise from metastasis of another source or primary tumor. The metastasized sites may be visible tumors, or may also be at the level of single cells, or micrometastases.

In an embodiment, the present invention is directed to a method for treating a pancreatic tumor or metastasized pancreatic tumor.

In an exemplary embodiment, the present invention is directed to a method for treating a colon tumor or metastasized colon tumor.

Reduction of tumor growth means a measurable decrease in growth of the tumor of at least about 0.01-fold (for example 0.01, 0.1, 1, 3, 4, 5, 10, 100, 1000-fold or more) or decrease by at least about 0.01% (for example 0.01, 0.1, 1, 3, 4, 5, 10, 20, 30, 40, 50, 60, 70, 80, 90, 95, 99 or 100%) as compared to the growth measured over time prior to treatment as defined herein.

Full eradication of the tumor may also be achieved through methods of the invention. Eradication refers elimination of the tumor. The tumor is considered to be eliminated when it is no longer detectable using detection methods known in the art (e.g., imaging).

Pharmaceutical Compositions

The invention provides pharmaceutical compositions for use in any of the methods described herein. The pharmaceutical compositions contain a therapeutic agent, an intracellular permeation enhancing agent, and/or an immunotherapeutic agent.

In embodiments, the pharmaceutical compositions include a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil, olive oil, gel (e.g., hydrogel), and the like. Saline is a preferred carrier when the pharmaceutical composition is administered intravenously. Saline solutions and aqueous dextrose and glycerol solutions can also be employed as liquid carriers particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin, the contents of which are hereby incorporated by reference in its entirety. Such compositions will generally contain a therapeutically effective amount of the therapeutic agent, the intracellular permeation enhancing agent, and/or the immunotherapeutic agent, in purified form, together with a suitable amount of carrier so as to provide the form for proper administration to the patient. The formulation should suit the mode of administration.

In embodiments, the therapeutic agent, the intracellular permeation enhancing agent or their combination, and/or the immunotherapeutic agent are administered locally as an immediate release or controlled release composition, for example by controlled dissolution and/or the diffusion of the active substance. Dissolution or diffusion controlled release can be achieved by incorporating the active substance into an appropriate matrix. A controlled release matrix may include one or more of shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

In related embodiments, the controlled release matrix is a hydrogel. A hydrogel is a three-dimensional, hydrophilic or amphiphilic polymeric network capable of taking up large quantities of water. The networks are composed of homopolymers or copolymers, which are insoluble due to the presence of covalent chemical or physical (e.g., ionic, hydrophobic interactions, entanglements) crosslinks. The crosslinks provide the network structure and physical integrity. Hydrogels exhibit a thermodynamic compatibility with water that allows them to swell in aqueous media. The chains of the network are connected in such a fashion that pores exist and that a substantial fraction of these pores are of dimensions between 1 nm and 1000 nm.

The hydrogels can be prepared by crosslinking hydrophilic biopolymers or synthetic polymers. Examples of the hydrogels formed from physical or chemical crosslinking of hydrophilic biopolymers, include but are not limited to, hyaluronans, chitosans, alginates, collagen, dextran, pectin, carrageenan, polylysine, gelatin, agarose, (meth)acrylate-oligolactide-PEO-oligolactide-(meth)acrylate, poly(ethylene glycol) (PEO), poly(propyleneglycol) (PPO), PEO-PPO-PEO copolymers (Pluronics), poly(phosphazene), poly(methacrylates), poly(N-vinylpyrrolidone), PL(G)A-PEO-PL(G)A copolymers, poly(ethylene imine), and the like. See Hennink and van Nostrum, Adv. Drug Del. Rev. 54:13-36 (2002); Hoffman, Adv. Drug Del. Rev. 43:3-12 (2002); Cadee et al., J Control. Release 78:1-13 (2002); Surini et al., J. Control. Release 90:291-301 (2003); and U.S. Pat. No. 7,968,085, each of which is incorporated by reference in its entirety. These materials consist of high-molecular weight backbone chains made of linear or branched polysaccharides or polypeptides.

The amount of the pharmaceutical composition of the invention which will be effective in the treatment or prevention of a solid tumor may depend on the nature of the tumor and can be determined by standard clinical techniques, including imaging techniques. In addition, in vitro assays may optionally be employed to help identify optimal dosage ranges. The precise dose to be employed in the formulation may also depend on the route of administration, and the seriousness of the tumor, and should be decided according to the judgment of the practitioner and each patient's circumstances. Effective doses may be extrapolated from dose-response curves derived from in vitro or animal model test systems.

Dosages and Administration Regimens

The therapeutic agents, intracellular permeation enhancing agents, immunotherapeutic agents, or compositions containing these agents are administered in a manner compatible with the dosage formulation, and in such amount as may be therapeutically affective, protective and immunogenic. The agents and/or compositions may be administered through different routes, including, but not limited to, oral, parenteral, buccal and sublingual, rectal, aerosol, nasal, intramuscular, subcutaneous, intradermal, and topical. The term parenteral as used herein includes, for example, intraocular, subcutaneous, intraperitoneal, intracutaneous, intravenous, intramuscular, intraarticular, intraarterial, intrasynovial, intrasternal, intrathecal, intralesional, and intracranial injection, or other infusion techniques.

In embodiments, administration of the therapeutic agents and/or the intracellular permeation enhancing agent is delivered locally or regionally (e.g., intratumorally).

In embodiments, the agents and/or compositions formulated according to the present invention are formulated and delivered in a manner to evoke a systemic immune response. Thus, in embodiments, the formulations are prepared by uniformly and intimately bringing into association the active ingredient with liquid carriers. Formulations suitable for administration include aqueous and non-aqueous sterile solutions, which may contain anti-oxidants, buffers, bacteriostats and solutes which render the formulation isotonic with the blood of the intended recipient, and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water, immediately prior to use. Extemporaneous solutions and suspensions may be prepared from sterile powders, granules and tablets commonly used by one of ordinary skill in the art.

The agents and/or compositions may be administered in different forms, including, but not limited to, solutions, emulsions and suspensions, microspheres, particles, microparticles, nanoparticles, liposomes, and the like.

The agents and/or compositions are administered in a manner compatible with the dosage formulation, and in such amount as may be therapeutically effective, immunogenic and protective. The quantity to be administered depends on the subject to be treated, including, for example, the size of the tumor, the stage of the disease, and the capacity of the individual's immune system to synthesize antibodies and/or to produce a cell-mediated immune response. Precise amounts of active ingredients required to be administered depend on the judgment of the practitioner. However, suitable dosage ranges are readily determinable by one skilled in the art and may be of the order of micrograms to milligrams of the active ingredient(s) per dose. The dosage may also depend on the route of administration and may vary according to the size of the host.

The agents and/or compositions should be administered to a subject in an amount effective to stimulate a protective immune response in the subject. Specific dosage and treatment regimens for any particular subject may depend upon a variety of factors, including the activity of the specific compound employed, the age, body weight, general health status, sex, diet, time of administration, rate of excretion, drug combination, the severity and course of the disease (including tumor size), condition or symptoms, the subject's disposition to the disease, condition or symptoms, method of administration, and the judgment of the treating physician. Actual dosages can be readily determined by one of ordinary skill in the art.

Exemplary unit dosage formulations are those containing a dose or unit, or an appropriate fraction thereof, of the administered ingredient. It should be understood that in addition to the ingredients mentioned herein, the formulations of the present invention may include other agents commonly used by one of ordinary skill in the art.

Typically in conventional systemically administered treatments, a therapeutically effective dosage should produce a serum concentration of compound of from about 0.1 ng/ml to about 50-100 µg/ml. The pharmaceutical compositions typically provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

In general, a therapeutically effective amount of the present compounds in dosage form usually ranges from slightly less than about 0.025 mg/kg/day to about 2.5 g/kg/day, preferably about 0.1 mg/kg/day to about 100 mg/kg/day of the patient or considerably more, depending upon the compound used, the condition or infection treated and the route of administration, although exceptions to this dosage range may be contemplated by the present invention. In an exemplary embodiment, intracellular permeation compounds according to the present invention may be administered intratumorally in amounts ranging from about 0.5 mg/ml of dosing solution to about 50 mg/ml. In another exemplary embodiment, intracellular permeation compounds according to the present invention may be administered intratumorally in amounts ranging from about 10 mg/ml to about 30 mg/ml. The dosage of the intracellular permeation compound(s) may depend on the type of cancer being treated, the particular compound used, the therapeutic agent, and other clinical factors and conditions of the patient and the route of administration. It is to be understood that the present invention has application for both human and veterinary use.

The agents and/or compositions are administered in one or more doses as required to achieve the desired effect. Thus, the agents and/or compositions may be administered in 1, 2, 3, 4, 5, or more doses. Further, the doses may be separated by any period of time, for example hours, days, weeks, months, and years.

The agents and/or compositions can be formulated as liquids or dry powders, or in the form of microspheres.

The agents and/or compositions may be stored at temperatures of from about −100° C. to about 25° C. depending on the duration of storage. The agents and/or compositions may also be stored in a lyophilized state at different temperatures including room temperature. The agents and/or compositions may be sterilized through conventional means known to one of ordinary skill in the art. Such means include, but are not limited to, filtration. The composition may also be combined with bacteriostatic agents to inhibit bacterial growth.

The amount of active ingredient that may be combined with carrier materials to produce a single dosage form may vary depending upon the host treated and the particular mode of administration. In embodiments, a preparation may contain from about 0.1% to about 95% active compound (w/w), from about 20% to about 80% active compound, or from any percentage therebetween.

In embodiments, the pH of the formulation may be adjusted with pharmaceutically acceptable acids, bases, or buffers to enhance the stability of the formulated compound or its delivery form.

In embodiments, the pharmaceutical carriers may be in the form of a sterile liquid preparation, for example, as a sterile aqueous or oleaginous suspension. Among the acceptable vehicles and solvents that may be employed are mannitol, water, Ringer's solution and isotonic sodium chloride solution.

In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

Other commonly used surfactants such as TWEEN® or SPAN® and/or other similar emulsifying agents or bioavailability enhancers which are commonly used in the manufacture of pharmaceutically acceptable solid, liquid, or other dosage forms may also be used for the purposes of formulation.

In embodiments, the agents and/or compositions can be delivered in an exosomal delivery system. Exosomes are small membrane vesicles that are released into the extracellular environment during fusion of multivesicular bodies with plasma membrane. Exosomes are secreted by various cell types including hematopoietic cells, normal epithelial cells and even some tumor cells. Exosomes are known to carry MHC class I, various costimulatory molecules and some tetraspanins. Recent studies have shown the potential of using native exosomes as immunologic stimulants.

Also contemplated by the invention is delivery of the agents and/or compositions using nanoparticles. For example, the agents and/or compositions provided herein can contain nanoparticles having at least one or more agents linked thereto, e.g., linked to the surface of the nanoparticle. A composition typically includes many nanoparticles with each nanoparticle having at least one or more agents linked thereto. Nanoparticles can be colloidal metals. A colloidal metal includes any water-insoluble metal particle or metallic compound dispersed in liquid water. Typically, a colloid metal is a suspension of metal particles in aqueous solution. Any metal that can be made in colloidal form can be used, including gold, silver, copper, nickel, aluminum, zinc, calcium, platinum, palladium, and iron. In some cases, gold nanoparticles are used, e.g., prepared from $HAuCl_4$. Nanoparticles can be any shape and can range in size from about 1 nm to about 10 nm in size, e.g., about 2 nm to about 8 nm, about 4 to about 6 nm, or about 5 nm in size. Methods for making colloidal metal nanoparticles, including gold colloidal nanoparticles from $HAuCl_4$, are known to those having ordinary skill in the art. For example, the methods described herein as well as those described elsewhere (e.g., US Pat. Publication Nos. 2001/005581; 2003/0118657; and 2003/0053983, which are hereby incorporated by reference) are useful guidance to make nanoparticles.

In certain cases, a nanoparticle can have two, three, four, five, six, or more active agents linked to its surface. Typically, many molecules of active agents are linked to the surface of the nanoparticle at many locations. Accordingly, when a nanoparticle is described as having, for example, two active agents linked to it, the nanoparticle has two active agents, each having its own unique molecular structure, linked to its surface. In some cases, one molecule of an active agent can be linked to the nanoparticle via a single attachment site or via multiple attachment sites.

An active agent can be linked directly or indirectly to a nanoparticle surface. For example, the active agent can be linked directly to the surface of a nanoparticle or indirectly through an intervening linker.

Any type of molecule can be used as a linker. For example, a linker can be an aliphatic chain including at least two carbon atoms (e.g., 3, 4, 5, 6, 7, 8, 9, 10 or more carbon atoms), and can be substituted with one or more functional groups including ketone, ether, ester, amide, alcohol, amine, urea, thiourea, sulfoxide, sulfone, sulfonamide, and disulfide functionalities. In cases where the nanoparticle includes gold, a linker can be any thiol-containing molecule. Reaction of a thiol group with the gold results in a covalent sulfide (—S—) bond. Linker design and synthesis are well known in the art.

In embodiments, the nanoparticle is linked to a targeting agent/moiety. A targeting functionality can allow nanoparticles to accumulate at the target at higher concentrations than in other tissues. In general, a targeting molecule can be one member of a binding pair that exhibits affinity and specificity for a second member of a binding pair. For example, an antibody or antibody fragment therapeutic agent can target a nanoparticle to a particular region or molecule of the body (e.g., the region or molecule for which the antibody is specific) while also performing a therapeutic function. In some cases, a receptor or receptor fragment can target a nanoparticle to a particular region of the body, e.g., the location of its binding pair member. Other therapeutic agents such as small molecules can similarly target a nanoparticle to a receptor, protein, or other binding site having affinity for the therapeutic agent.

When the compositions of this invention comprise one or more additional therapeutic or prophylactic agents, the therapeutic/enhancing/immunotherapy agent and the additional agent should be present at dosage levels of between about 0.1 to 100%, or between about 5 to 95% of the dosage normally administered in a monotherapy regimen. The additional agents may be administered separately, as part of a multiple dose regimen, from the agents of this invention. Alternatively, those additional agents may be part of a single dosage form, mixed together with the agents of this invention in a single composition.

The administration of the agents and/or compositions of the invention elicits an immune response against an immunogen, e.g., a cancer antigen. Typically, the dose can be adjusted within this range based on, e.g., the subject's age, the subject's health and physical condition, the capacity of the subject's immune system to produce an immune response, the subject's body weight, the subject's sex, diet, time of administration, the degree of protection desired, and other clinical factors. Those in the art can also readily address parameters such as biological half-life, bioavailability, route of administration, and toxicity when formulating the agents and/or compositions of the invention.

The following examples further demonstrate several embodiments of this invention. While the examples illustrate the invention, they are not intended to limit it.

EXAMPLES

The structures, materials, compositions, and methods described herein are intended to be representative examples of the invention, and it will be understood that the scope of the invention is not limited by the scope of the examples. Those skilled in the art will recognize that the invention may be practiced with variations on the disclosed structures, materials, compositions and methods, and such variations are regarded as within the ambit of the invention.

Example 1

Preparation of dosing solution 1: 167 mg of NaOH were dissolved into 20 ML of de-ionized water to create a sodium hydroxide solution of 0.21 molar. Eighty (80) mgs of 6-Oxo-6-phenylhexanoic acid (obtained from Rieke Metals, Lincoln Nebr.) were weighed out and dissolved into 2 ML of the 0.21 Normal sodium hydroxide solution. In a separate container 6.2 mg of cis-Diaminodichloroplatinum (obtained from Tocris Bioscience, Elisville Mo.) were dissolved into 2.5 ML of de-ionized water. Each material was vortexed for 1 minute and sonicated for 15 minutes. 1.25 ML of the 6-Oxo-6-phenylhexanoic solution were mixed with the 2.5 ML cis-Diaminodichloroplatinum solution and vortexed for 1 minute. The pH of the resulting clear solution was measured and found to be approximately 5.5. Twenty (20) microliters of 1N sodium hydroxide was added to the combined solution. The pH was measured and found to be approximately 6.8. The volume was adjusted to 5 ML by the addition of approximately 1.2 ML of deionized water.

Example 2

Preparation of dosing solution 2: Eighty (80) mgs of 6-Oxo-6-phenylhexanoic acid (obtained from Rieke Metals, Lincoln Nebr.) were weighed out and dissolved into 2 ML of the 0.21 Normal sodium hydroxide solution as described in example 1. In a separate container 20 mg cis-Diammine (1,1-cyclobutanedicarboxylato) platinum (Sigma Aldrich C2538) were dissolved into 2.5 ML of de-ionized water. Each material was vortexed for 1 minute and sonicated for 15 minutes. 1.25 MLs of the 6-Oxo-6-phenylhexanoic solution were mixed with the 2.5 ML cis-Diammine(1,1-cyclobutanedicarboxylato) platinum solution and vortexed for 1 minute. The pH of the resulting clear combined solution was measured and found to be approximately 6.0. Ten (10) microliters of 1N sodium hydroxide was added to the combined solution. The pH was measured and found to be approximately 6.9. The volume was adjusted to 5 ML by the addition of approximately 1.2 ML of deionized water.

Example 3

Preparation of dosing solution 3: 137 mg of NaOH were dissolved into 20 ML of de-ionized water to create a sodium hydroxide solution of 0.16 molar. Eighty (80) microliters of 2-ethylhexyl 2-hydroxybenzoate (obtained from ChemPacific, Baltimore Md.) were weighed out and mixed with 2 ML of the 0.16 Normal sodium hydroxide solution. In a separate container 6.2 mg of cis-Diaminodichloroplatinum (obtained from Tocris Bioscience, Elisville Mo.) were dissolved into 2.5 ML of de-ionized water. Each material was vortexed for 1 minute and sonicated for 15 minutes. 1.25 ML of the 2-ethylhexyl 2-hydroxybenzoate solution were mixed with the 2.5 ML cis-Diaminodichloroplatinum solution and vortexed for 1 minute. The pH of the resulting clear solution was measured and found to be approximately 11. Several titrations using 50% HCl solution and 2N sodium hydroxide solution were added to the combined solution. After several titrations the pH was measured and found to be approximately 6.8.

Example 4

Preparation of dosing solution 4: Eighty (80) microliters of 2-ethylhexyl 2-hydroxybenzoate (obtained from ChemPacific, Baltimore Md.) were weighed out and mixed with 2 ML of the 0.16 Normal sodium hydroxide solution as described in example 3. In a separate container 20 mg cis-Diammine(1,1-cyclobutanedicarboxylato) platinum (Sigma Aldrich C2538) were dissolved into 2.5 ML of de-ionized water. Each material was vortexed for 1 minute and sonicated for 15 minutes. 1.25 MLs of the 2-ethylhexyl 2-hydroxybenzoate salt solution were mixed with the 2.5 ML cis-Diammine(1,1-cyclobutanedicarboxylato) platinum solution and vortexed for 1 minute. The pH of the resulting clear solution was measured and found to be approximately 11. Several titrations using 50% HCl solution and 2N sodium hydroxide solution were added to the combined solution. After several titrations the pH was measured and found to be approximately 6.8.

Example 5

Figure 2:
FIG. 2 is a photo of excised BxPC tumor tissue showing penetration by 50 microliters of enhancer with dye. 50 microliters of enhancer India ink solution was distributed in 2 minutes using a programmable syringe into a BxPc s.c.i.d. mouse tumor of approximately 500 mm$^3$.

30 mg of 6-oxo-6 phenylhexanoic acid was added to 1.5 ml of 0.1 molar sodium hydroxide, and the pH was adjusted to approximately 7.0. A few drops of India black ink was added to the 7.0 penetration enhancer ink solution. $2 \times 10^6$ BxPC-3-luc2 cells were inoculated into the right flank of 9 female C.B-17 scid mice. Tumor growth was monitored once or twice weekly by caliper measurements until tumor size reached ~500 mm$^3$. In vivo bioluminescent imaging was performed on the day of ink chemical solution delivery as shown in FIG. 1. 50 microliters of the enhancer solution were injected into the BxPC subcutaneous tumors of two severely compromised immunodeficient (scid) mice using a programmable syringe pump with a butterfly needle. The needle remained in the tumors for approximately 2 additional minutes. Upon removal of the needle the tumors were immediately excised and examined; the resulting ink dispersion efficacy was observed and is shown in FIG. 2.

Example 6

Figure 3:
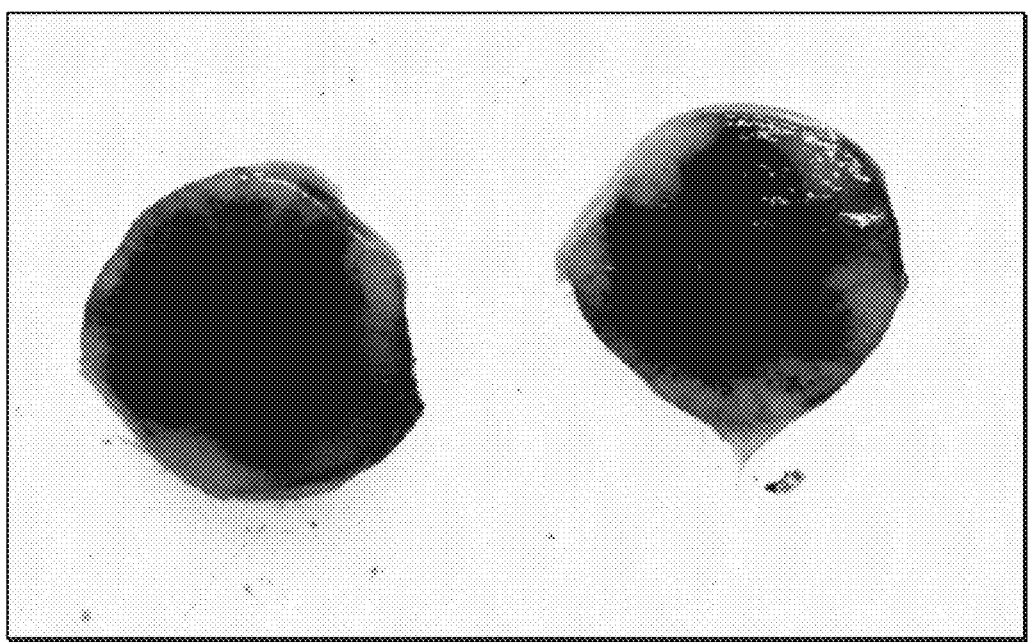
FIG. 3 is a photo of excised BxPC tumor tissue with penetration by 100 microliters of enhancer with dye. 100 microliters of the enhancer India ink solution was distributed in 2 minutes using a programmable syringe pump into a BxPc-3 s.c.i.d. mouse tumor of approximately 500 mm$^3$.

Two scid mice with subcutaneous BxPC tumors were administered intratumorally 100 microliters of the India ink enhancer solution prepared in Example 5 in two minutes using the programmable syringe pump. The needle remained in the tumors for approximately 2 additional minutes. Upon removal of the needle the tumors were immediately excised and examined; the resulting ink dispersion efficacy was observed and is shown in FIG. 3.

Example 7

$2 \times 10^6$ BxPC-3-luc2 cells were inoculated into the right flank of 32 female C.B-17 scid mice. Tumor growth was monitored once or twice weekly by caliper measurements until tumor size reached ~500 mm$^3$. Twenty-four mice with tumors of the appropriate size were selected for dosing. Each selected animal was numbered on their tail and ear tagged with the same number. The final groupings are noted in Table 1.

TABLE 1

| Group | Treatment | Animal ID |
|---|---|---|
| 1 | Enhancer inVehicle | 69 |
| 1 | Enhancer inVehicle | 70 |
| 1 | Enhancer inVehicle | 78 |
| 1 | Enhancer inVehicle | 82 |
| 1 | Enhancer inVehicle | 85 |
| 1 | Enhancer inVehicle | 87 |
| 2 | CisplatinIV | 71 |
| 2 | CisplatinIV | 73 |
| 2 | CisplatinIV | 76 |
| 2 | CisplatinIV | 77 |
| 2 | CisplatinIV | 84 |
| 2 | CisplatinIV | 92 |
| 3 | Cisplatin Intratumor | 72 |
| 3 | Cisplatin Intratumor | 75 |
| 3 | Cisplatin Intratumor | 80 |
| 3 | Cisplatin Intratumor | 86 |
| 3 | Cisplatin Intratumor | 89 |
| 3 | Cisplatin Intratumor | 94 |
| 4 | Cisplatin + Enhancer | 67 |
| 4 | Cisplatin + Enhancer | 83 |
| 4 | Cisplatin + Enhancer | 91 |
| 4 | Cisplatin + Enhancer | 96 |
| 4 | Cisplatin + Enhancer | 97 |
| 4 | Cisplatin + Enhancer | 98 |

The tumor size of each animal was measured by caliper and the animals divided into four groups such that the average tumor volume (using the caliper measure) for each group was similar. The groupings are shown in Table 2.

TABLE 2

| Animal ID | length (mm) | Width (mm) | Volume (mm$^3$) |
|---|---|---|---|
| 69 | 17.08 | 10.06 | 864.28 |
| 70 | 11.54 | 9.55 | 526.24 |
| 78 | 11.17 | 8.98 | 450.38 |
| 82 | 10.62 | 10.07 | 538.46 |
| 85 | 12.48 | 9.98 | 621.51 |
| 87 | 12.28 | 9.73 | 581.29 |
| Group 1 | | Average | 597.03 |
| 71 | 13.70 | 8.26 | 467.36 |
| 73 | 11.57 | 9.57 | 529.82 |
| 76 | 17.39 | 9.03 | 709.00 |
| 77 | 11.58 | 11.08 | 710.82 |
| 84 | 11.66 | 9.94 | 576.02 |
| 92 | 11.29 | 9.97 | 561.12 |
| Group 2 | | Average | 592.36 |
| 72 | 15.60 | 9.14 | 651.61 |
| 75 | 11.25 | 8.94 | 449.57 |
| 80 | 13.32 | 9.61 | 615.06 |
| 86 | 15.72 | 10.36 | 843.61 |
| 89 | 12.04 | 9.75 | 572.28 |
| 94 | 10.16 | 9.26 | 435.60 |
| Group 3 | | Average | 594.62 |
| 67 | 9.85 | 9.54 | 448.23 |
| 83 | 12.30 | 9.65 | 572.70 |
| 91 | 11.41 | 10.74 | 658.06 |
| 96 | 14.53 | 10.26 | 764.77 |
| 97 | 10.04 | 9.61 | 463.61 |
| 98 | 14.37 | 9.69 | 674.64 |
| Group 4 | | Average | 597.00 |

The animals were then injected with luciferase 3 to obtain a tumor bioluminescence measurement (BLI) using a Xenogen photonic instrument (Xenogen became a division of Caliper Life Sciences). The four groups were then assigned to a treatment regimen. Group one was treated intratumorally with 100 microliters of enhancer 6-oxo-6 phenylhexanoic acid prepared as a sodium salt at pH approximately 7.0 and concentration of 13.3 mg/ML. Group two was treated with 100 microliters of cisplatin administered intravenously into the tail artery in a buffered solution at concentration of 1.2 mg/ml. Group three was treated intratumorally with 100 microliters of cisplatin in a buffered solution at a dose of approximately 0.45 mg/ml. Group 4 was administered intratumorally 100 microliters of the sodium salt form of enhancer 6-oxo-6 phenylhexanoic acid prepared with a final concentration of 13.3 mg/ml combined with cisplatin at a final concentration of 0.45 mg/ml.

Example 8

Figure 4:
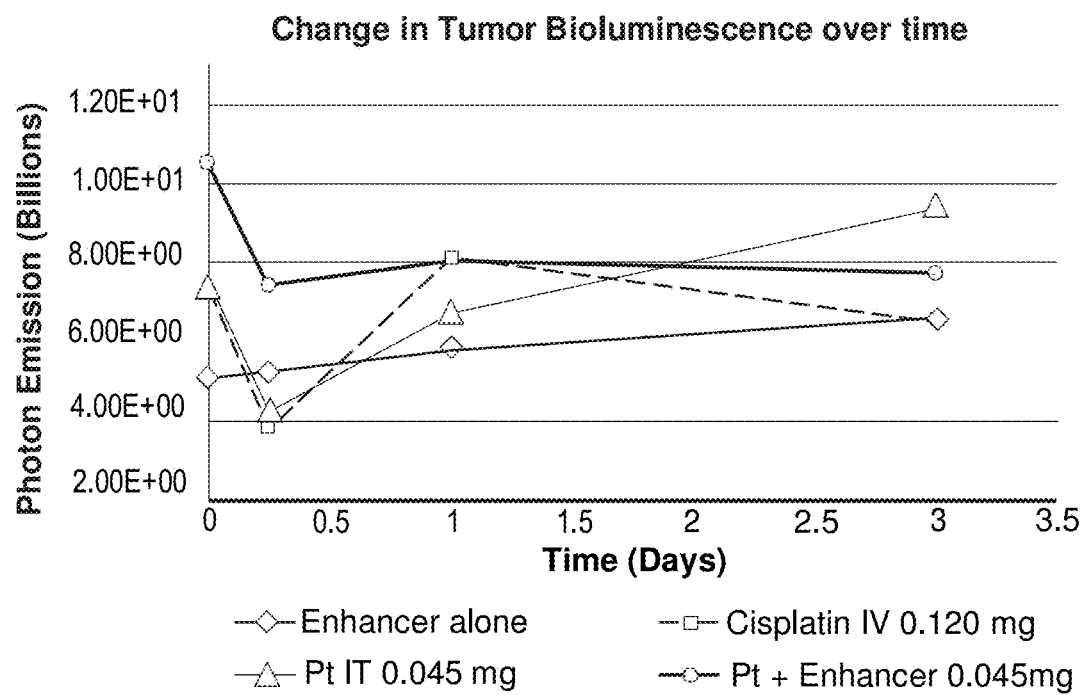
FIG. 4 is a graph showing the bioluminescence (BLI) readings for dosing groups in Example 8 from baseline to 72 hrs.

BLI readings for the animals administered from Example 7 were taken at six hours post dosing, 24 hours post dosing, and 72 hours post dosing. Caliper measurements of the tumors for the animals in all groups were taken pre-dose and 72 hours post dose. Results comparing baseline, 6 hour, 24 hour and 72 hour BLI time-points for the animals are shown in FIG. 4.

Example 9

Figure 5:
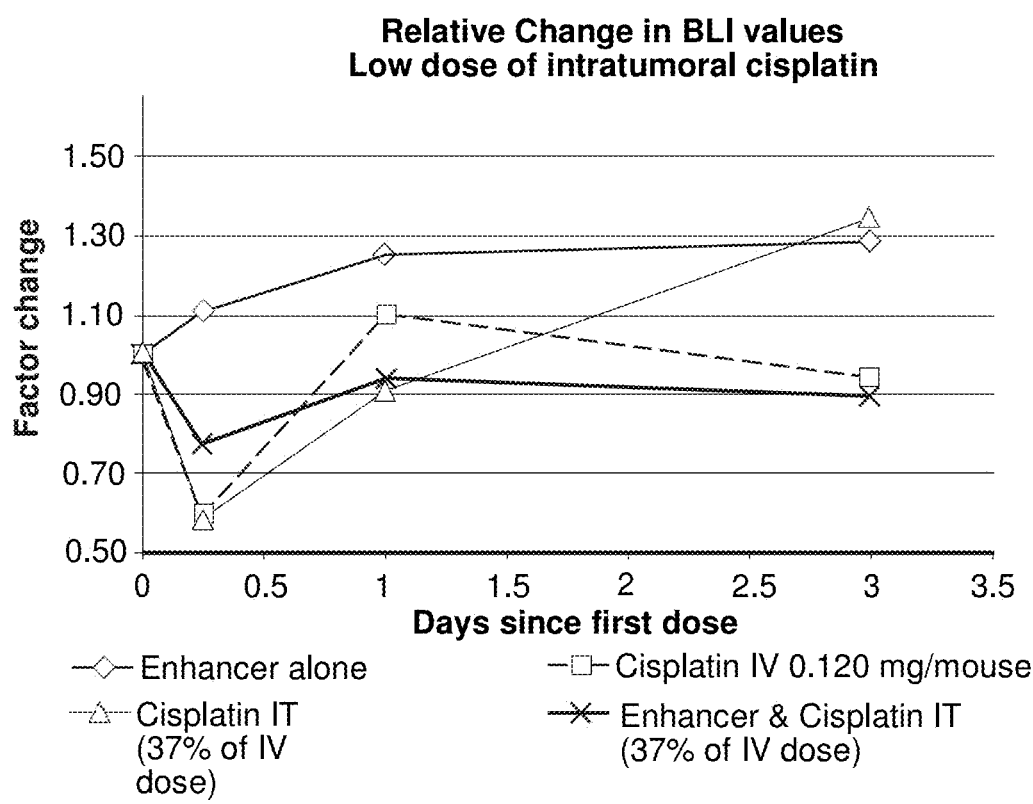
FIG. 5 is a graph showing the relative change in bioluminescence (BLI) from baseline to 72 hours.

The animals described in example 7 were administered a second set of treatments following a measurement of their tumor bioluminescence at 72 hours. Group one was treated intratumorally with 100 microliters of enhancer 6-oxo-6 phenylhexanoic acid prepared as a sodium salt at pH approximately 7.0 and concentration of 13.3 mg/ML. Group two was treated with 100 microliters cisplatin administered intravenously into the tail artery as a buffered solution at concentration of 1.2 mg/ml. Group three was treated intratumorally with 100 microliters of cisplatin in a buffered solution at a dose of approximately 1.2 mg/ml. Group 4 was administered intratumorally 100 microliters of the sodium salt form of enhancer 6-oxo-6 phenylhexanoic acid prepared with a final concentration of 13.3 mg/ml combined with cisplatin at a final concentration of 1.2 mg/ml. BLI values of these cisplatin intratumoral doses were evaluated through day 3 of the study. Relative values of BLI results through day 3 are shown in FIG. 5.

Example 10

Figure 6:
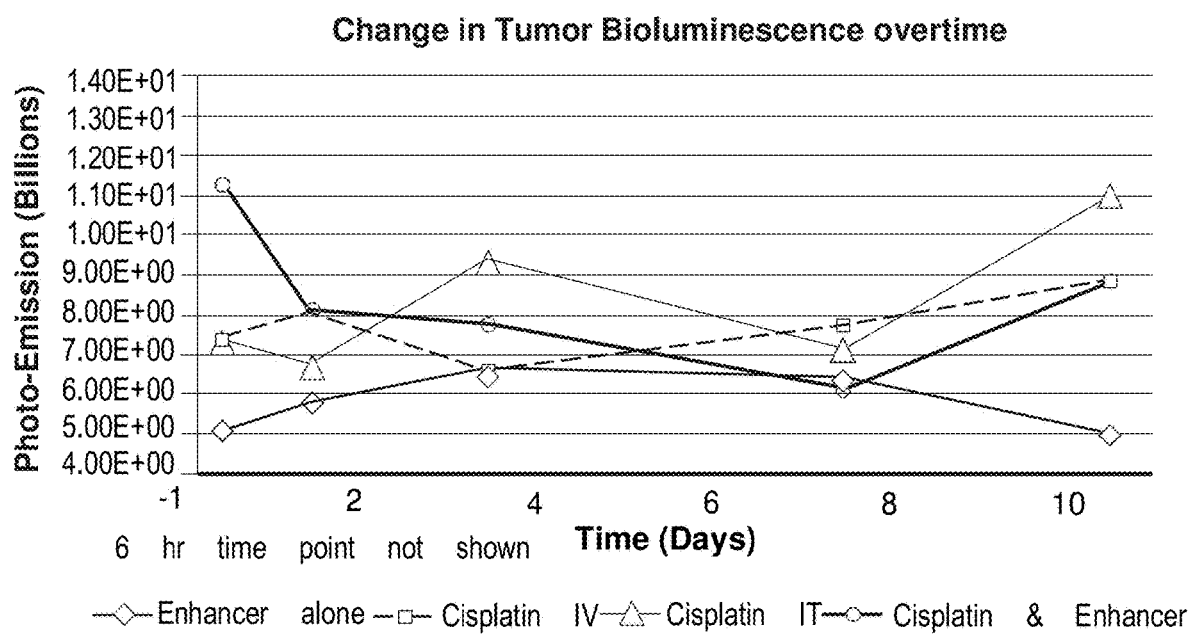
FIG. 6 is a graph showing the bioluminescence (BLI) values from baseline to day 10 from Example 10.
Figure 7:
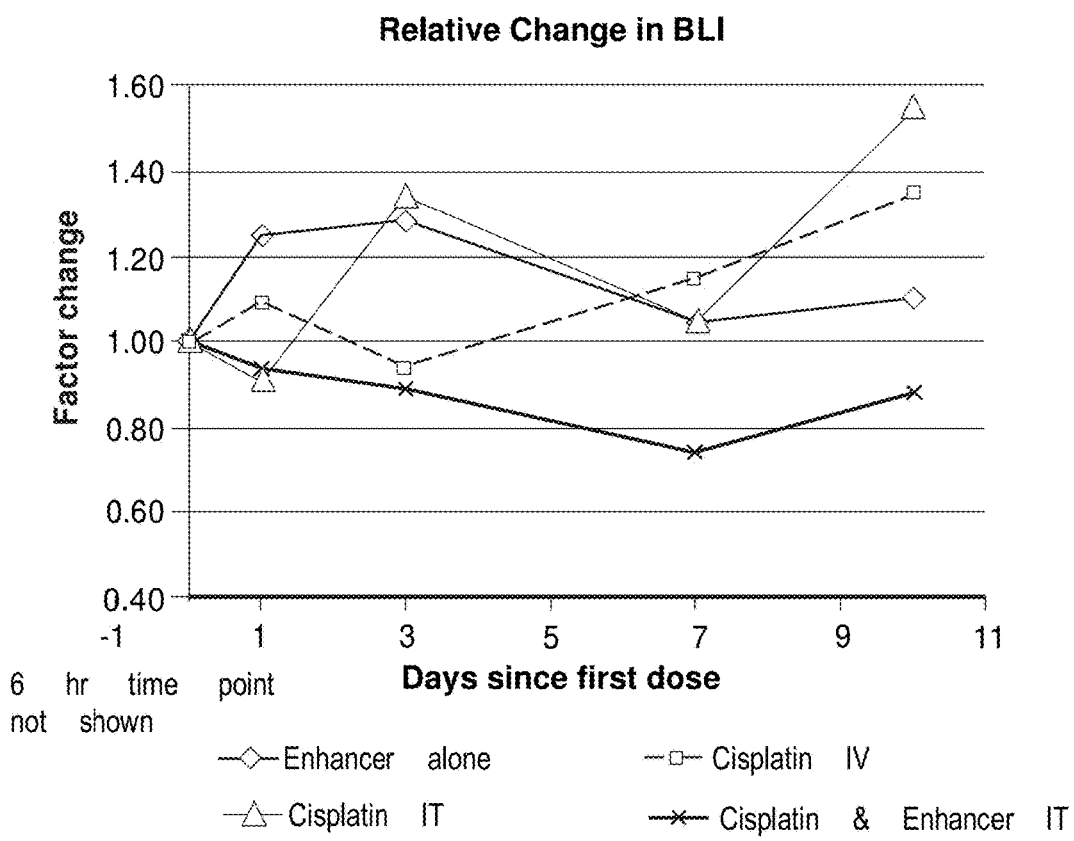
FIG. 7 is a graph showing the relative bioluminescence (BLI) values from baseline to day 10 from Example 10.
Figure 8:
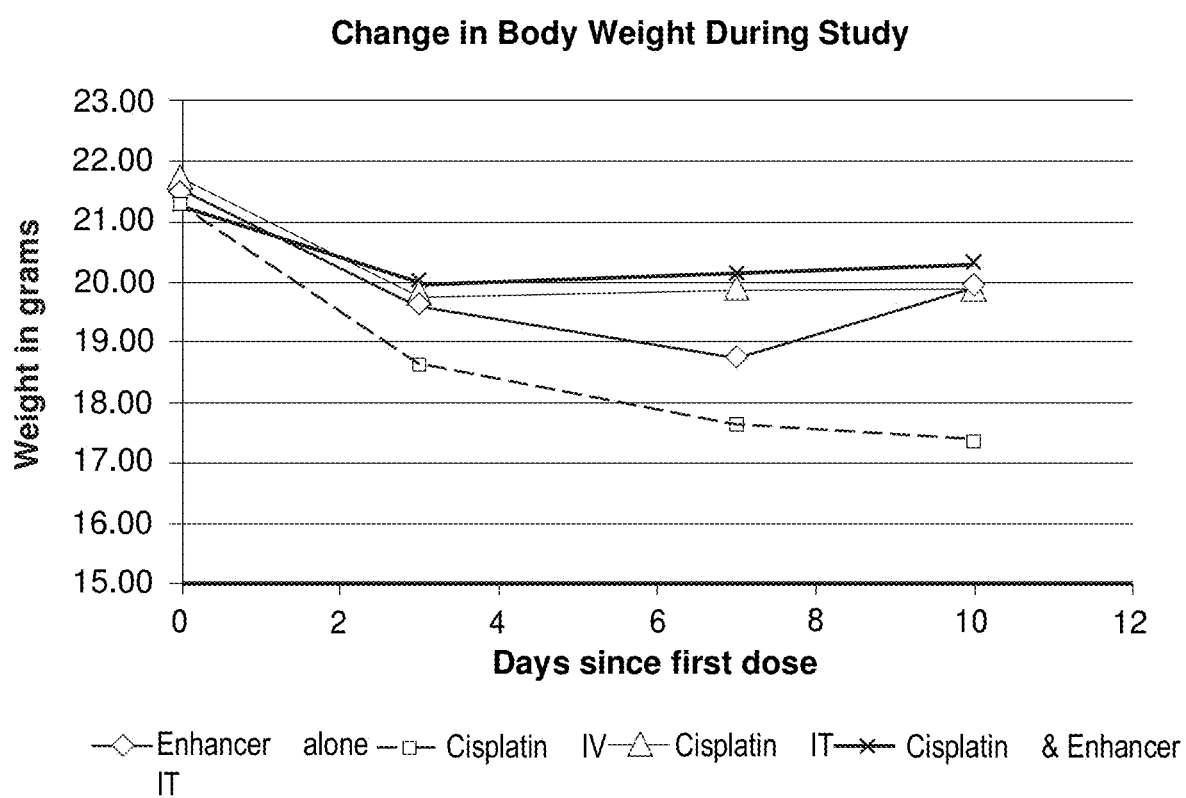
FIG. 8 is a graph showing the body weights changes from baseline to day 10 from Example 10

The animals described in example 7 were administered a third set of treatments following a measurement of their tumor bioluminescence at 7 and 10 days post baseline. The doses administered for the third treatment to each group (1 to 4) were identical to those administered in in the second treatment described in Example 9. BLI values over the entire study are shown in FIG. 6. Relative change in BLI values over the entire study are shown in FIG. 7. FIG. 8 shows the changes in body weight from baseline to day 10.

Example 11

Formulations were prepared for dosing. An example is that of group 7 which is as follows: 11.8 mgs of sodium hydroxide pellets were dissolved in 6.0 mls of water. The solution was sonicated for 2 to 3 minutes. 80 mgs of 8-[(2-hydroxybenzoyl)amino] octanoic acid was added to the 6.0 mls of sodium hydroxide solution prepared above, and sonicated for 2 minutes. 2.0 ml of a solution of Tween 80 from a prepared stock solution (0.8 mgs of Tween 80/ml) was added to the 6 mls of enhancer salt solution. To the 8.0 ml of enhancer salt solution from above, 12.0 mgs of cisplatin powder obtained from Tocris Bioscience was added and the entire solution was sonicated as needed to assure complete dissolution of all components. The pH was adjusted to between 6.8 and 7.2 using a weak HCL or 1 N sodium hydroxide solution. Once the pH was correct, the solution was filtered using a 0.45 micron sieve. This material was prepared for dosing as noted in example 12.

Example 12

$1 \times 10^6$ Colon CT26 cells were inoculated into the flank of over 120 female balb/c immune competent mice. Tumor growth was monitored once or twice weekly by caliper measurements until the largest tumor reached ~500 mm³. After sixteen days 120 mice with tumors were selected for inclusion in the study. Each selected animal was numbered and tagged with the corresponding number. The animals were then matched by tumor volume and placed into 12 groups with a mean tumor volume per animal per group ranging from 341 mm³ to 349 mm³. Animals were treated with 1 of 12 different regimens and classified as Group 1-12, respectively, based on the identifying characteristics enumerated in Table 3.

TABLE 3

| Group | n | Enhancer Agent | Vehicle | mg/animal | Route | Schedule | Agent | Vehicle | mg/animal | Route | Schedule |
|---|---|---|---|---|---|---|---|---|---|---|---|
| 1# | 10 | No Treatment | — | — | — | — | No Treatment | — | — | — | — |
| 2 | 10 | Sodium 8 cyclohexyl-8oxo-octanoate | | 0.3 | it | 2/1/3 | Cisplatin | | 0.05 | it | 2/1/3 |
| 3 | 10 | Sodium 8 cyclohexyl-8oxo-octanoate | | 1 | it | 2/1/3 | Cisplatin | | 0.15 | it | 2/1/3 |
| 4* | 10 | Sodium 8 cyclohexyl-8oxo-octanoate | | 1 | it | 2/1/3 | Cisplatin | | 0.05 | it | 2/1/3 |
| 5 | 10 | Sodium 8 cyclohexyl-8oxo-octanoate | | 3 | it | 2/1/3 | Cisplatin | | 0.15 | it | 2/1/3 |
| 6 | 10 | Sodium 8-[(2-hydroxy-benzoyl)amino] octanoate | | 0.3 | it | 2/1/3 | Cisplatin | | 0.05 | it | 2/1/3 |
| 7 | 10 | Sodium 8-[(2-hydroxy-benzoyl)amino] octanoate | | 1 | it | 2/1/3 | Cisplatin | | 0.15 | it | 2/1/3 |
| 8* | 10 | Sodium 8-[(2-hydroxy-benzoyl)amino] octanoate | | 1 | it | 2/1/3 | Cisplatin | | 0.05 | it | 2/1/3 |
| 9 | 10 | None | saline | — | — | — | Cisplatin | | 0.15 | it | 2/1/3 |
| 10 | 10 | Sodium 6-Oxo-6-phenylhexanoate | | 1 | it | 2/1/3 | Cisplatin | | 0.15 | it | 2/1/3 |
| 11 | 10 | Sodium 6-Oxo-6-phenylhexanoate | | 3 | it | 2/1/3 | Cisplatin | | 0.15 | it | 2/1/3 |
| 12 | 10 | cisplatin | saline | 2.7* | ip | 2/1/3 | — | — | — | — | — |

Figure 9:
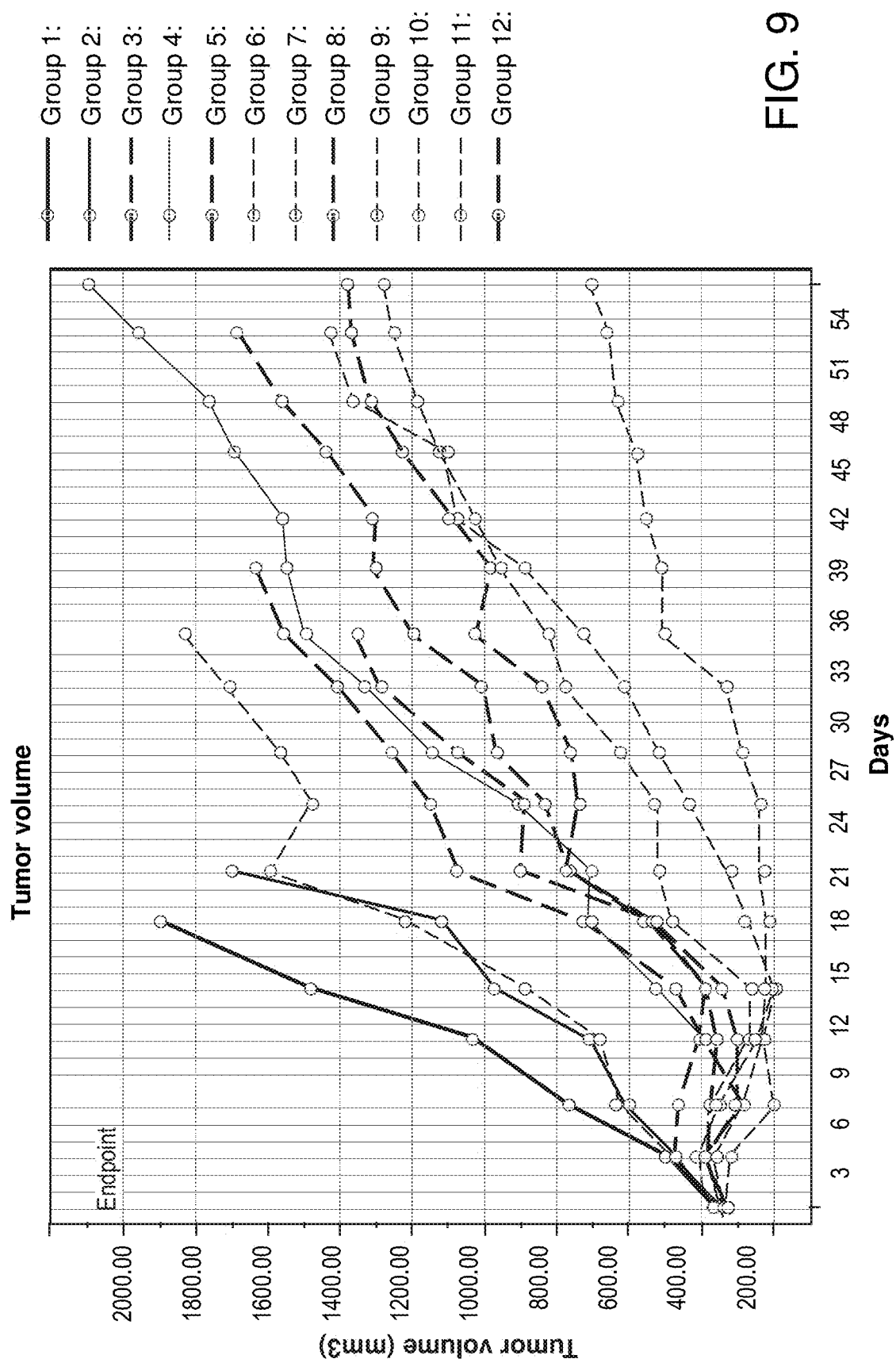
FIG. 9 is a graph showing progression of tumor volume for 120 animals that were matched by tumor volume and placed into 12 groups with an initial, predose mean tumor volume per animal per group ranging from 341 mm$^3$ to 349 mm$^3$. The line representing each group is referenced in the legend.
Figure 10:
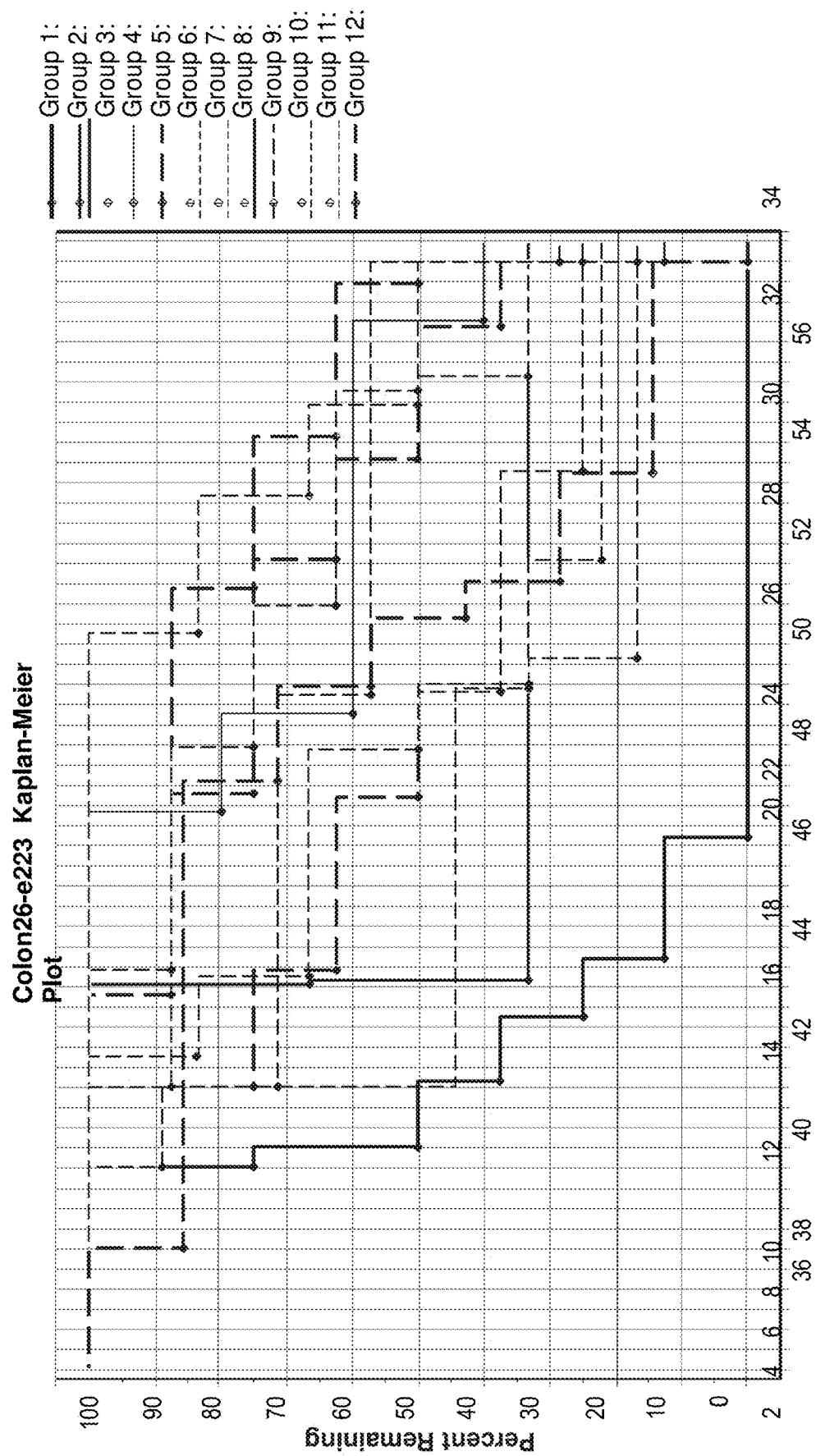
FIG. 10 is a Kaplan-Meier plot showing the ability of exemplary intracellular formulations of the invention to extend animal life.

Control Group
*Dosed per 400 mm3 of tumor volume measured
Schedule 2/1/3 means 2 days of dosing, one no dose day followed by 3 days of dosing
it means intratumoral,
ip means intraperitoneal The results of this study are shown in FIG. 9, which depicts tumor volume over time for each of the 12 Groups analyzed by the study. In addition, as shown in FIG. 10, several intracellular formulations were able to show a significant extension of animal life versus control groups, and an overall survival benefit versus no treatment and also versus animals given drug alone systemically. Exemplary formulations according to an illustrative embodiment of the invention are shown in Table 4.

TABLE 4

| Group | Enhancer | Vehicle | Enhancer Concentration mgs/ML | Cisplatin Concentration mgs/ML | Surfactant |
|---|---|---|---|---|---|
| 2 | Sodium cyclohexyl-8-oxo-octanoate | Water | 3 | 0.5 | None |
| 3 | Sodium cyclohexyl-8-oxo-octanoate | Water | 10 | 1.5 | None |
| 4 | Sodium cyclohexyl-8-oxo-octanoate | Water | 10 | 0.5 | ~1% Tween |
| 5 | Sodium cyclohexyl-8-oxo-octanoate | Water | 30 | 1.5 | None |
| 6 | Sodium 8-[(2-hydroxybenzoyl)amino]octanoate | Water | 3 | 0.5 | None |
| 7 | Sodium 8-[(2-hydroxybenzoyl)amino]octanoate | Water | 10 | 1.5 | None |
| 8 | Sodium 8-[(2-hydroxybenzoyl)amino]octanoate | Water | 10 | 0.5 | ~1% Tween |
| 9 | None | Saline | 0 | 1.5 | None |
| 10 | Sodium 6-Oxo-6 phenylhexanoate | Water | 10 | 1.5 | None |
| 11 | Sodium 6-Oxo-6 phenylhexanoate | Water | 30 | 1.5 | None |

The pH was adjusted to between 6.8 and 7.2

Example 13

Figure 11A:
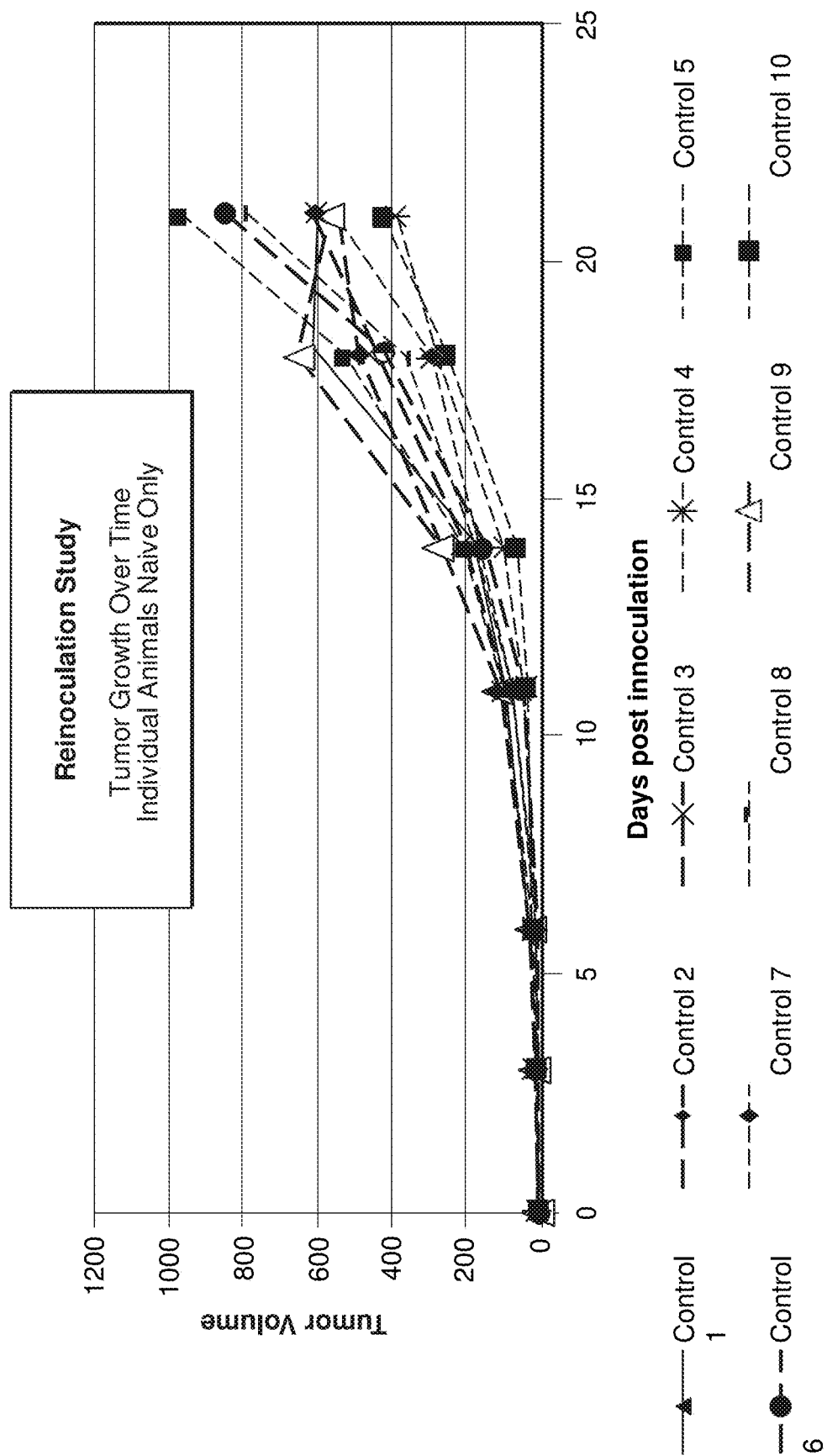
FIGS. 11A-11C are plots depicting results of an exemplary study in which mice whose tumors regressed to less than 18 mm$^3$ were reinoculated with 1×10$^6$ CT26 mouse colon cancer cells.
Figure 11B:
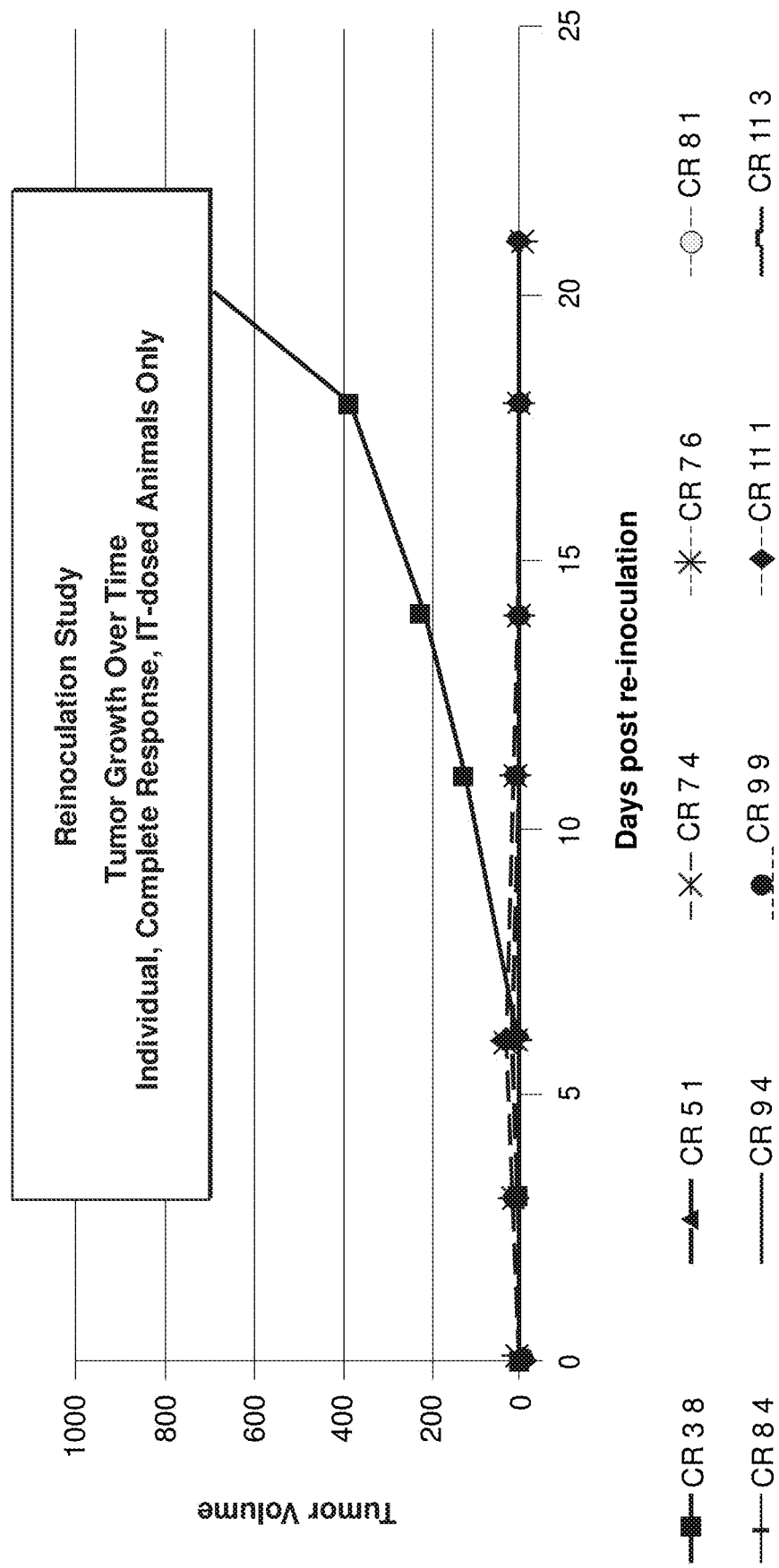
Figure 11C:
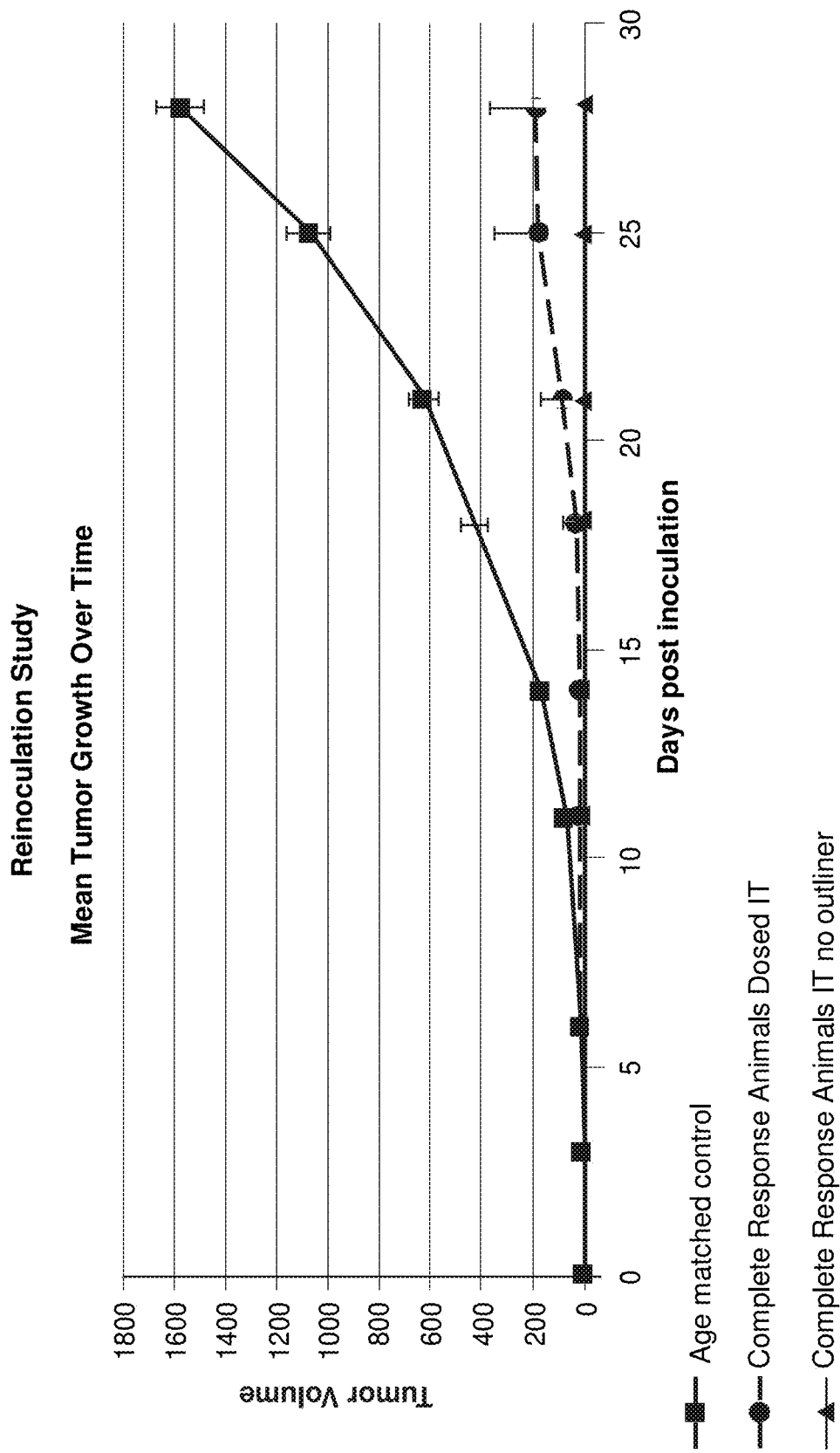

Ten animals from the study described in example 12, which had received intratumorally administered drug, had their tumors regress to sizes below 18 mm$^3$. These animals were placed in a new study and along with a control group of age matched naïve animals. Both groups were then inoculated with 1×10$^6$ Colon CT26 cells into their flank. The animals previously inoculated were re-inoculated in the opposite flank. No drug treatment was provided to either group. Tumor growth was inhibited in the animals that have previously demonstrated a regression whereas naïve animals showed significant tumor growth. FIGS. 11A-C show that 90% of the animals that had a complete response were fully immunized against recurrence of the cancer. The top figure (a) is the 10 animals from the control group. The second figure (b) are the animals that had shown a complete response in the study describe in example 12. The bottom figure (c) are the mean values and standard error of the means for the two groups.

Having thus described in detail preferred embodiments of the present invention, it is to be understood that the invention defined by the above paragraphs is not to be limited to particular details set forth in the above description as many apparent variations thereof are possible without departing from the spirit or scope of the present invention. All documents cited or referenced herein and all documents cited or referenced in the herein cited documents, together with any manufacturer's instructions, descriptions, product specifications, and product sheets for any products mentioned herein or in any document incorporated by reference herein, are hereby incorporated by reference, and may be employed in the practice of the invention.

I claim:

1. A method of treating cancer in a subject in need thereof comprising intratumorally administering a pharmaceutical composition comprising an aqueous solution, the aqueous solution comprising a therapeutically effective amount of a therapeutic agent and an intracellular permeation enhancing agent, wherein the therapeutic agent is a chemotherapeutic agent, an interfering RNA, a therapeutic protein or a therapeutic antibody, wherein the therapeutic agent is mixed with and not covalently bound to the intracellular permeation enhancing agent, and wherein the intracellular permeation enhancing agent is 6-Oxo-6-phenylhexanoic acid, 8-Oxo-8-phenyloctanoic acid, 8-(2,5-Dichlorophenyl)-8-oxooctanoic acid, N-[8-(2-hydroxybenzoyl)aminooctanoic acid, N-[8-(2-hydroxybenzoyl)aminodecanoic acid, N-(5-chlorosalicyloyl)-8-aminocaprylic acid, N-[4-(4-chloro-2hydroxybenzoyl)amino1 butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, a functionally effective salt of any of the foregoing, or any combination thereof.

2. The method of claim 1, wherein the intracellular permeation enhancing agent is N-[8-(2-hydroxybenzoyl) aminooctanoic acid.

3. The method of claim 1, wherein the intracellular permeation enhancing agent is 6-Oxo-6-phenylhexanoic acid.

4. The method of claim 1, wherein the intracellular permeation enhancing agent is 8-Cyclohexyl-8-oxooctanoic acid.

5. The method of claim 1, wherein the intracellular permeation enhancing agent is 8-(2,5-Dichlorophenyl)-8-oxooctanoic acid.

6. The method of claim 1, wherein the intracellular permeation enhancing agent is 7-Cyclohexyl-7-oxoheptanoic acid.

7. The method of claim 1, wherein the therapeutic agent is a platinum agent.

8. The method of claim 1, wherein the therapeutic agent is cisplatin.

9. The method of claim 1, wherein the therapeutic agent is a *vinca* alkaloid agent.

10. The method of claim 1, wherein the therapeutic agent is vinblastine.

11. The method of claim 1, wherein the therapeutic agent is cisplatin and vinblastine.

12. A method of treating cancer in a subject in need thereof comprising intratumorally administering a pharmaceutical composition comprising an aqueous solution, the aqueous solution comprising a therapeutically effective amount of a therapeutic agent and an intracellular permeation enhancing agent, wherein the therapeutic agent is a chemotherapeutic agent, an interfering RNA, a therapeutic protein or a therapeutic antibody, and wherein the therapeutic agent is mixed with and not covalently bound to the intracellular permeation enhancing agent, wherein the intracellular permeation enhancing agent is 6-Oxo-6-phenylhexanoic acid, 8-Oxo-8-phenyloctanoic acid, 8-(2,5-Dichlorophenyl)-8-oxooctanoic acid, N-[8-(2-hydroxybenzoyl) aminooctanoic acid, N-[8-(2-hydroxybenzoyl) aminodecanoic acid, N-(5-chlorosalicyloyl)-8-aminocaprylic acid, N-[4-(4-chloro-2hydroxybenzoyl) amino1 butanoic acid, 2-ethylhexyl 2-hydroxybenzoate, 5-Cyclohexyl-5-oxovaleric acid, 6-Cyclohexyl-6-oxohexanoic acid, 7-Cyclohexyl-7-oxoheptanoic acid, 8-Cyclohexyl-8-oxooctanoic acid, 4-Cyclopentyl-4-oxobutyric acid, 5-Cyclopentyl-5-oxovaleric acid, 6-Cyclopentyl-6-oxohexanoic acid, 7-Cyclopentyl-7-oxoheptanoic acid, 8-Cyclopentyl-8-oxooctanoic acid, 4-Cyclobutyl-4-oxobutyric acid, 5-Cyclobutyl-5-oxovaleric acid, 6-Cyclobutyl-6-oxohexanoic acid, 7-Cyclobutyl-7-oxoheptanoic acid, 8-Cyclobutyl-8-oxooctanoic acid, 4-Cyclopropyl-4-oxobutyric acid, 5-Cyclopropyl-5-oxovaleric acid, 6-Cyclopropyl-6-oxohexanoic acid, 7-Cyclopropyl-7-oxoheptanoic acid, 8-Cyclopropyl-8-oxooctanoic acid, a functionally effective salt of any of the foregoing, or any combination thereof, and further comprising administering a therapeutically effective amount of an immunotherapeutic agent.

13. The method of claim 12, wherein the intracellular permeation enhancing agent is N-[8-(2-hydroxybenzoyl) aminooctanoic acid.

14. The method of claim 12, wherein the intracellular permeation enhancing agent is 6-Oxo-6-phenylhexanoic acid.

15. The method of claim 12, wherein the intracellular permeation enhancing agent is 8-Cyclohexyl-8-oxooctanoic acid.

16. The method of claim 12, wherein the intracellular permeation enhancing agent is 8-(2,5-Dichlorophenyl)-8-oxooctanoic acid.

17. The method of claim 12, wherein the intracellular permeation enhancing agent is 7-Cyclohexyl-7-oxoheptanoic acid.

18. The method of claim 12, wherein the therapeutic agent is a platinum agent.

19. The method of claim 12, wherein the therapeutic agent is cisplatin.

20. The method of claim 12, wherein the therapeutic agent is a vinca alkaloid agent.

21. The method of claim 12, wherein the therapeutic agent is vinblastine.

22. The method of claim 12, wherein the therapeutic agent is cisplatin and vinblastine.

* * * * *

UNITED STATES PATENT AND TRADEMARK OFFICE
CERTIFICATE OF CORRECTION

PATENT NO. : 10,888,618 B2
APPLICATION NO. : 15/441907
DATED : January 12, 2021
INVENTOR(S) : Lewis H. Bender It is certified that error appears in the above-identified patent and that said Letters Patent is hereby corrected as shown below:

On the Title Page

On page 2, in Item (56), under "Other Publications", in Column 2, Line 73, delete "protransfenome" and insert --protransfersome--;

On page 3, in Item (56), under "Other Publications", in Column 1, Line 9, delete "85" and insert --65--;

On page 3, in Item (56), under "Other Publications", in Column 1, Line 24, delete "SPIRIS" and insert --SPIRITS--;

On page 3, in Item (56), under "Other Publications", in Column 1, Line 67, delete "Dendrimier" and insert --Dendrimer--.

Signed and Sealed this
Twenty-first Day of February, 2023

Katherine Kelly Vidal
*Director of the United States Patent and Trademark Office*